US008168402B2

(12) United States Patent
Tabakoff et al.

(10) Patent No.: US 8,168,402 B2
(45) Date of Patent: May 1, 2012

(54) DIAGNOSTIC TESTS OF SUBSTANCE USE DISORDERS

(75) Inventors: Boris Tabakoff, Denver, CO (US); Lawrence Snell, Aurora, CO (US)

(73) Assignee: Lohocla Research Corporation, Aurora, CO (US)

( * ) Notice: Subject to any disclaimer, the term of this patent is extended or adjusted under 35 U.S.C. 154(b) by 503 days.

(21) Appl. No.: 12/084,306

(22) PCT Filed: Nov. 3, 2006

(86) PCT No.: PCT/US2006/043098
§ 371 (c)(1),
(2), (4) Date: Mar. 2, 2009

(87) PCT Pub. No.: WO2007/056223
PCT Pub. Date: May 18, 2007

(65) Prior Publication Data
US 2009/0305318 A1    Dec. 10, 2009

Related U.S. Application Data

(60) Provisional application No. 60/733,386, filed on Nov. 3, 2005.

(51) Int. Cl.
G01N 33/567  (2006.01)
G01N 31/00   (2006.01)
G01N 33/53   (2006.01)
A61K 49/00   (2006.01)

(52) U.S. Cl. ......... 435/7.21; 435/7.1; 435/7.24; 436/10; 436/15; 436/63; 436/811; 436/901; 424/9.2

(58) Field of Classification Search .................. 435/7.1, 435/7.21, 7.24, 7.72; 436/10, 15, 63, 811, 436/901; 424/9.2
See application file for complete search history.

(56) References Cited

U.S. PATENT DOCUMENTS

| 4,770,996 A | 9/1988 | Tabakoff |
| 5,475,096 A | 12/1995 | Gold et al. |
| 5,958,785 A * | 9/1999 | Pullarkat et al. ............ 436/94 |
| 2004/0180370 A1 | 9/2004 | Tabakoff et al. |

OTHER PUBLICATIONS

Snell et al. Relationships between effects of smoking, gender, and alcohol dependence on platelet monoamine oxidase-B: Activity, affinity labeling, and protein measurements, Alcoholism, Clinical and Experimental Research 26 (7):1105-1113.*

Coccini et al. Platelet monoamine oxidase B activity as a state marker for alcoholism: trend over time during withdrawal and influence of smoking and gender, Alcohol and alcoholism (Nov.-Dec. 2002) vol. 37, No. 6, pp. 566-572.*

Hoffman et al., Identification of state markers of alcohol consumption using proteomic techniques, Alcoholism, Clinical and Experimental Research 28 (8), suppl. 3): 53A (2004).*

(Continued)

Primary Examiner — Gail R Gabel
(74) Attorney, Agent, or Firm — Morrison & Foerster LLP

(57) ABSTRACT

The present invention relates to compositions and methods for identifying and quantifying platelet proteins that relate to various bodily states. The present invention further provides methods and compositions for determining whether an individual is using alcohol or other licit or illicit drugs at levels hazardous or harmful to their health. The invention also provides methods for identifying individuals who would benefit from or who may be harmed by specific medications or therapies.

15 Claims, 26 Drawing Sheets

OTHER PUBLICATIONS

Fluck et al. (The influence of alcoholism and cirrhosis on benzodiazepine receptor function, Pharmacology, biochemistry, and behavior, (Apr. 1998) vol. 59, No. 4, pp. 949-954.*

European Search Report and Written Opinion mailed Mar. 3, 2010, for EP 06836939.6 filed May 7, 2008, 6 pages.

Hoffman et al. (2004). "Identification of state markers of alcohol consumption using proteomic techniques" *Alcoholism, Clinical and Experimental Research* 28(8, suppl. 3):53A.

International Search Report mailed Jun. 11, 2008, for PCT/US06/43098 filed Nov. 3, 2006, 2 pages.

Liu et al. (2004). "A model for random sampling and estimation of relative protein abundance in shotgun proteomics," Anal Chem, 76:4193-4201.

Rommelspacher (1994). "Longitudinal observations of monoamine oxidase-B in alcoholics: differentiation of marker characteristics," *Alcoholism, Clinical and Experimental Research* 18(6):1322-1329.

Snell et al. (2002). "Relationships between effects of smoking, gender, and alcohol dependence on platelet monoamine oxidase-B: Activity, affinity labeling, and protein measurements," *Alcoholism, Clinical and Experimental Research* 26(7):1105-1113.

Washburn (2004). "Utilisation of proteomics datasets generated via multidimensional protein identification technology (MudPIT)" *Briefings in Functional Genomics & Proteomics* 3(3):280-286.

Yu (1994). "Pharmacological and Clinical Implications of MAO-B Inhibitors," *General Pharmacology* 25(8):1527-1539.

Snell et al. (Sep. 6, 2011). "The Biometric Measurement of Alcohol Consumption," *Alcohol Clin Exp Res.*, Epub ahead of print, 10 pages.

\* cited by examiner

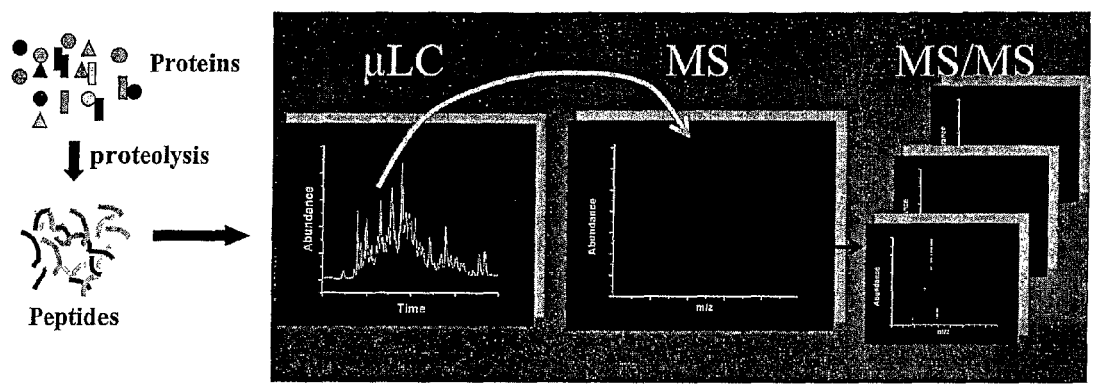
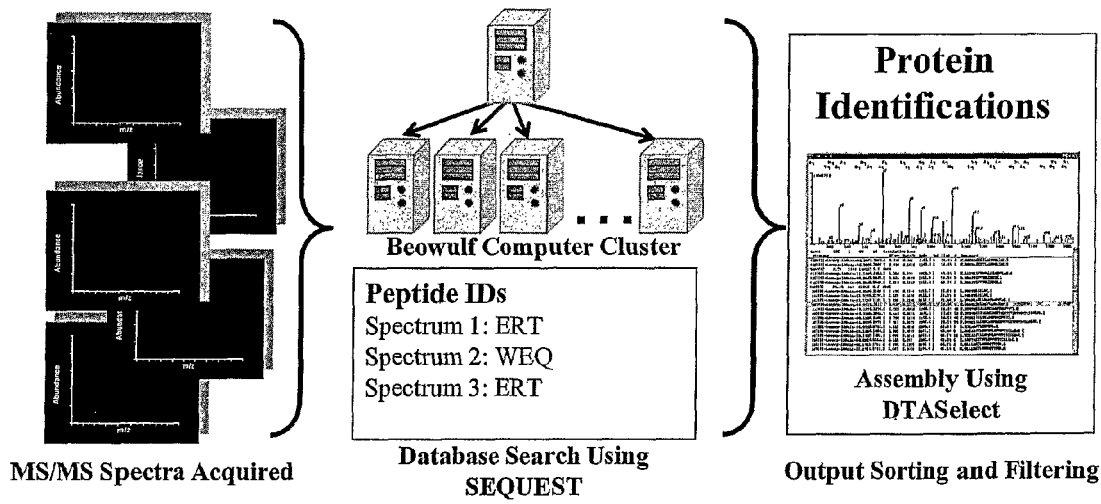
FIG. 1 gi|38202207|ref|NP_000889.3| amine oxidase (flavin-containing); MAO, platelet [Homo sapiens]

```
 1   MSNKCDVVVV GGGISGMAAA KLLHDSGLNV VVLEARDRVG GRTYTLRNQK VKYVDLGGSY VGPTQNRILR LAKELGLETY -
 1   -KVNEVERLIH HVKGKSYPFR GPFPPVWNPI TYLDHNNFWR TMDDMGREIP SDAPWKAPLA EEWDNMTMKE LLDKLCWTES -
 2              GKSYPFR GPFPPVWNPI TY         DDMGREIP SDAPWKAPL                                7
 3                SYPFR GPFPPVWNPI TY         DDMGREIP SDAPWKAPLA E                             8
 3                SYPFR GPFPPVWNPI TY
 4                SYPFR GPFPPVWNPI TYL
 5                    R GPFPPVWNPI TY
 5                    R GPFPPVWNPI TY
 6                    R GPFPPVWNPI TYL
 1   -AKQLATLFVN LCVTAETHEV SALWFLWYVK QCGGTTRIIS TTNGGQERKF VGGSGQVSER IMDLLGDRVK LERPVIYIDQ -
 1   -TRENVLVETL NHEMYEAKYV ISAIPPTLGM KIHFNPPLPM MRNQMITRVP LGSVIKCIVY YKEPFWRKKD YCGTMIIDGE -
 9                                   IHFNPPLPM
 9                                   IHFNPPLPM
10                                   IHFNPPLPM M
 1   -EAPVAYTLDD TKPEGNYAAI MGFILAHKAR KLARLTKEER LKKLCELYAK VLGSLEALEP VHYEEKNWCE EQYSGGCYTT -
 1   -YFPPGILTQY GRVLRQPVDR IYFAGTETAT HWSGYMEGAV EAGERAAREI LHAMGKIPED EIWQSEPESV DVPAQPITTT -
11              RQPVDR IYFA                                                      SV DVPAQPITTT  12
13                                                                                          T-
 1   -FLERHLPSVP GLLRLIGLTT IFSATALGFL AHKRGLLVRV
13  -FLERHLPSVP GLL                                                                    SEQ ID
14   FLERHLPSVP GLL                                                                      NO
14   FLERHLPSVP GLL
15     LERHLPSVP GLL
15     LERHLPSVP GLL
15     LERHLPSVP GLL
16       RHLPSVP GLL
16       RHLPSVP GLL
```

SEQ ID
NO

FIG. 2

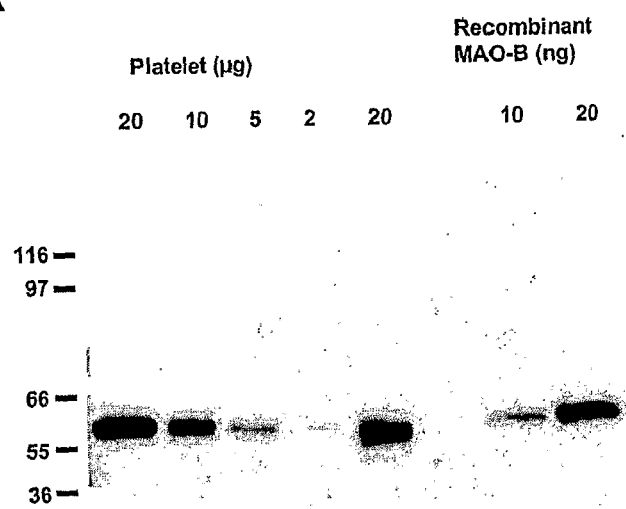
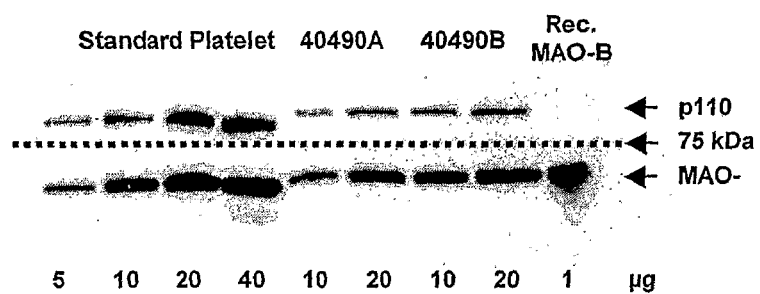
FIG. 3

FIG. 9A Alphabetically Sorted List of Platelet Proteins

| Locus | Spectrum Count | Sequence Coverage | Descriptive Name |
|---|---|---|---|
| gi|7656867|ref|NP_055059.1| | 3 | 1.1% | a disintegrin and metalloprotease with thrombospondin motifs-2 isoform 1; procollagen I N-proteinase; Procollagen N-endopeptidase [Homo sapiens] |
| gi|4501887|ref|NP_001605.1| | 121 | 46.7% | actin, gamma 1 propeptide; cytoskeletal gamma-actin; actin, cytoplasmic 2 [Homo sapiens] |
| gi|4501891|ref|NP_001093.1| | 16 | 1.5% | actinin, alpha 1 [Homo sapiens] |
| gi|10181096|ref|NP_056085.1| | 4 | 1.7% | adenylate cyclase 6 isoform a [Homo sapiens] |
| gi|4502027|ref|NP_000468.1| | 10 | 11.5% | albumin precursor; PRO0883 protein [Homo sapiens] |
| gi|4557225|ref|NP_000005.1| | 6 | 1.4% | alpha 2 macroglobulin precursor [Homo sapiens] |
| gi|4758028|ref|NP_004360.1| | 9 | 1.3% | alpha 3 type VI collagen isoform 1 precursor; collagen VI, alpha-3 polypeptide [Homo sapiens] |
| gi|39573713|ref|NP_945183.1| | 5 | 1.1% | ALS2CR17; beach [Homo sapiens] |
| gi|27370154|ref|NP_766366.1| | 13 | 6.2% | amine oxidase (flavin-containing) [Mus musculus] |
| gi|38202207|ref|NP_000889.3| | 44 | 8.1% | amine oxidase (flavin-containing); MAO, platelet; MAO, brain; tyramine oxidase, adrenalin oxidase [Homo sapiens] |
| gi|41406055|ref|NP_958816.1| | 4 | 5.2% | amyloid beta A4 protein precursor isoform b; protease nexin-II; amyloid beta-peptide; amyloid of aging and Alzheimer disease; Alzheimer disease 1; cerebral vascular amyloid peptide [Homo sapiens] |
| gi|29029632|ref|NP_004295.2| | 3 | 0.8% | anaplastic lymphoma kinase Ki-1; ALK (tyrosine kinase receptor precursor; CD246 antigen [Homo sapiens] |
| gi|10947052|ref|NP_001139.2| | 4 | 0.5% | ankyrin 2 isoform 1; ankyrin-2, nonerythrocytic; ankyrin-B; ankyrin, brain; ankyrin, neuronal; ankyrin, nonerythroid; Long QT syndrome-4; long (electrocardiographic) QT syndrome 4 [Homo sapiens] |
| gi|4502107|ref|NP_001145.1| | 7 | 5.9% | annexin 5; endonexin II, anchorin CII; lipocortin V; placental anticoagulant protein I [Homo sapiens] |
| gi|4502111|ref|NP_001147.1| | 3 | 3.0% | annexin VII isoform 1; annexin VII (synexin); synexin [Homo sapiens] |
| gi|4557321|ref|NP_000030.1| | 5 | 6.0% | apolipoprotein A-I precursor [Homo sapiens] |
| gi|4502153|ref|NP_000375.1| | 24 | 2.7% | apolipoprotein B precursor; apoB-100; apoB-48 [Homo sapiens] |
| gi|4502051|ref|NP_000688.1| | 7 | 8.1% | arachidonate 12-lipoxygenase; 12(S)-lipoxygenase [Homo sapiens] |
| gi|5031573|ref|NP_005712.1| | 19 | 16.5% | ARP3 actin-related protein 3 homolog; ARP3 (actin-related protein 3, yeast) homolog [Homo sapiens] |
| gi|14589866|ref|NP_004309.2| | 9 | 2.4% | aspartate beta-hydroxylase isoform a; junctin isoform 1; junctate; aspartyl/asparaginyl-beta-hydroxylase; peptide-aspartate beta-dioxygenase; humbug [Homo sapiens] |
| gi|40068464|ref|NP_065783.2| | 6 | 1.4% | AT rich interactive domain 1B (SWI1-like) isoform 2; BRG1-binding protein ELD/OSA1; Eld (eyelid)/Osa protein [Homo sapiens] |

FIG. 9B Alphabetically Sorted List of Platelet Proteins

| Locus | Count | Coverage | Descriptive Name |
|---|---|---|---|
| gi\|20336203\|ref\|NP_000042.2\| | 3 | 0.6% | ataxia telangiectasia mutated protein isoform 1; AT protein; AT mutated; human phosphatidylinositol 3-kinase homolog; serine-protein kinase ATM; AT complementation group A; AT complementation group C; AT complementation group D; AT complementation group E |
| gi\|19923445\|ref\|NP_056999.2\| | 3 | 2.7% | atlastin; guanylate-binding protein 3 [Homo sapiens] |
| gi\|21361565\|ref\|NP_001679.2\| | 5 | 7.4% | ATP synthase, H+ transporting, mitochondrial F0 complex, subunit b, isoform 1 [Homo sapiens] |
| gi\|5453559\|ref\|NP_006347.1\| | 20 | 8.1% | ATP synthase, H+ transporting, mitochondrial F0 complex, subunit d [Homo sapiens] |
| gi\|4757810\|ref\|NP_004037.1\| | 32 | 14.3% | ATP synthase, H+ transporting, mitochondrial F1 complex, alpha subunit, isoform 1, cardiac muscle; ATP synthase, H+ transporting, mitochondrial F1 complex, alpha subunit, isoform 2, non-cardiac muscle-like 2 [Homo sapiens] |
| gi\|32189394\|ref\|NP_001677.2\| | 22 | 10.0% | ATP synthase, H+ transporting, mitochondrial F1 complex, beta polypeptide [Homo sapiens] |
| gi\|40254456\|ref\|NP_001675.2\| | 3 | 3.8% | ATPase, Ca++ transporting, plasma membrane 4 [Homo sapiens] |
| gi\|4557876\|ref\|NP_000341.1\| | 12 | 1.3% | ATP-binding cassette, sub-family A member 4; ATP binding cassette transporter; ATP-binding transporter, retina-specific; rim protein [Homo sapiens] |
| gi\|27502429\|ref\|NP_525021.2\| | 3 | 0.8% | ATP-binding cassette, sub-family A, member 10; ATP-binding cassette A10 [Homo sapiens] |
| gi\|45446740\|ref\|NP_001597.2\| | 4 | 0.7% | ATP-binding cassette, sub-family A, member 2 [Homo sapiens] |
| gi\|27477115\|ref\|NP_525022.2\| | 4 | 0.7% | ATP-binding cassette, sub-family A, member 9 isoform a; ATP-binding cassette A9 [Homo sapiens] |
| gi\|4557481\|ref\|NP_000383.1\| | 3 | 0.9% | ATP-binding cassette, sub-family C (CFTR/MRP), member 2; canalicular multispecific organic anion transporter [Homo sapiens] |
| gi\|6715561\|ref\|NP_011162.2\| | 5 | 1.3% | ATP-binding cassette, sub-family C, member 6; anthracycline resistance-associated [Homo sapiens] |
| gi\|20336307\|ref\|NP_060484.2\| | 3 | 6.1% | B-cell CLL/lymphoma 11A isoform 2; ecotropic viral integration site 9 homolog; C2H2-type zinc finger protein [Homo sapiens] |
| gi\|4502839\|ref\|NP_000072.1\| | 10 | 0.9% | beige protein homolog; Lysosomal trafficking regulator [Homo sapiens] |
| gi\|13562114\|ref\|NP_110400.1\| | 10 | 17.7% | beta tubulin 1, class VI [Homo sapiens] |
| gi\|4557327\|ref\|NP_000033.1\| | 34 | 18.0% | beta-2-glycoprotein I precursor [Homo sapiens] |
| gi\|40255055\|ref\|NP_079225.3\| | 3 | 1.5% | BH3-only member B protein [Homo sapiens] |
| gi\|4502451\|ref\|NP_000050.1\| | 4 | 0.5% | breast cancer 2, early onset; Fanconi anemia, complementation group D1 [Homo sapiens] |
| gi\|4557377\|ref\|NP_000052.1\| | 3 | 3.0% | Bruton agammaglobulinemia tyrosine kinase [Homo sapiens] |

FIG. 9C Alphabetically Sorted List of Platelet Proteins

| Locus | Count | Coverage | Descriptive Name |
|---|---|---|---|
| gi\|4502443\|ref\|NP_001714.1\| | 4 | 0.8% | bullous pemphigoid antigen 1 isoform 1e precursor; bullous pemphigoid antigen 1 (230/240kD); dystonin; hemidesmosomal plaque protein |
| gi\|34577049\|ref\|NP_056363.2\| | 3 | 0.7% | bullous pemphigoid antigen 1 isoform 1eA precursor; bullous pemphigoid antigen 1 (230/240kD); dystonin; hemidesmosomal plaque protein [Homo sapiens] |
| gi\|4757956\|ref\|NP_004053.1\| | 4 | 1.9% | cadherin 16 precursor; KSP-cadherin; kidney-specific cadherin [Homo sapiens] |
| gi\|16507962\|ref\|NP_071407.2\| | 8 | 1.4% | cadherin related 23 isoform 1 precursor; cadherin-23; otocadherin [Homo sapiens] |
| gi\|13386500\|ref\|NP_000059.2\| | 7 | 1.2% | calcium channel, alpha 1A subunit isoform 1; calcium channel, L type, alpha-1 polypeptide, isoform 4; brain calcium channel 1 [Homo sapiens] |
| gi\|4885103\|ref\|NP_005174.1\| | 3 | 0.7% | calcium channel, voltage-dependent, alpha 1F subunit; Cav1.4alpha1 [Homo sapiens] |
| gi\|4557401\|ref\|NP_000060.1\| | 4 | 1.1% | calcium channel, voltage-dependent, L type, alpha 1S subunit; HypoPP; calcium channel, L type, alpha 1 polypeptide, isoform 3 (skeletal muscle; hypokalemic periodic paralysis) [Homo sapiens] |
| gi\|33598954\|ref\|NP_037518.2\| | 4 | 2.7% | calcium-binding transporter [Homo sapiens] |
| gi\|10716563\|ref\|NP_001737.1\| | 35 | 9.1% | calnexin [Homo sapiens] |
| gi\|12408656\|ref\|NP_005177.2\| | 28 | 14.6% | calpain 1, large subunit; calpain, large polypeptide L1; calcium-activated neutral proteinase [Homo sapiens] |
| gi\|18105007\|ref\|NP_004332.2\| | 5 | 1.6% | carbamoyl-phosphate synthetase 2/aspartate transcarbamylase/dihydroorotase; CAD trifunctional protein; multifunctional protein CAD [Homo sapiens] |
| gi\|4885049\|ref\|NP_005150.1\| | 83 | 34.5% | cardiac muscle alpha actin proprotein; smooth muscle actin [Homo sapiens] |
| gi\|21618331\|ref\|NP_000746.2\| | 4 | 2.6% | carnitine acetyltransferase isoform 1 precursor [Homo sapiens] |
| gi\|27804309\|ref\|NP_038523.1\| | 6 | 4.8% | carnitine palmitoyltransferase 1a, liver; carnitine palmitoyltransferase 1, liver; L-CPT I [Mus musculus] |
| gi\|4503021\|ref\|NP_001867.1\| | 6 | 5.6% | carnitine palmitoyltransferase 1A; carnitine palmitoyltransferase I, liver [Homo sapiens] |
| gi\|4557014\|ref\|NP_001743.1\| | 3 | 7.8% | catalase [Homo sapiens] |
| gi\|4502687\|ref\|NP_003865.1\| | 4 | 8.5% | CD84 antigen (leukocyte antigen); leukocyte antigen CD84 [Homo sapiens] |
| gi\|5729770\|ref\|NP_000382.3\| | 3 | 3.2% | ceroid-lipofuscinosis, neuronal 2, late infantile (Jansky-Bielschowsky disease) [Homo sapiens] |
| gi\|31542301\|ref\|NP_056195.2\| | 13 | 7.0% | CGI-51 protein [Homo sapiens] |
| Contaminant_gi\|14278658\|pdb\|1IC6\|A | 10 | 23.3% | Chain A, Structure Of A Serine Protease Proteinase K From Tritirachium Album Limber At 0.98 A Resolution |
| gi\|21361116\|ref\|NP_004376.2\| | 3 | 1.2% | chondroitin sulfate proteoglycan 2 (versican) [Homo sapiens] |
| gi\|40255045\|ref\|NP_060506.4\| | 3 | 1.3% | chromosome 14 open reading frame 103 [Homo sapiens] |
| gi\|42660378\|ref\|XP_290629.4\| | 7 | 0.4% | chromosome 14 open reading frame 78 [Homo sapiens] |
| gi\|4758012\|ref\|NP_004850.1\| | 4 | 2.5% | clathrin heavy chain 1; clathrin, heavy polypeptide-like 2 [Homo sapiens] |
| gi\|42716297\|ref\|NP_001822.2\| | 13 | 8.4% | clusterin isoform 1; complement-associated protein SP-40 [Homo sapiens] |

FIG. 9D  Alphabetically Sorted List of Platelet Proteins

| Locus | Count | Coverage | Descriptive Name |
|---|---|---|---|
| gi\|4503631\|ref\|NP_000120.1\| | 9 | 3.0% | coagulation factor XIII A1 subunit precursor; Coagulation factor XIII, A polypeptide; TGase [Homo sapiens] |
| gi\|11067435\|ref\|NP_067730.1\| | 6 | 2.9% | coagulation factor XIIIa [Rattus norvegicus] |
| gi\|15011913\|ref\|NP_001839.1\| | 3 | 3.6% | collagen, type VI, alpha 1 precursor; collagen VI, alpha-1 polypeptide [Homo sapiens] |
| gi\|10834974\|ref\|NP_000564.1\| | 4 | 0.7% | complement component (3b/4b) receptor-1 isoform F precursor; complement component (3b/4b) receptor-1; C3-binding protein; CD35 antigen [Homo sapiens] |
| gi\|4557385\|ref\|NP_000055.1\| | 12 | 1.1% | complement component 3 precursor; acylation-stimulating protein cleavage product [Homo sapiens] |
| gi\|14577919\|ref\|NP_009224.1\| | 10 | 3.2% | complement component 4A preproprotein; acidic C4, Rodgers form of C4; C4A anaphylatoxin [Homo sapiens] |
| gi\|4502397\|ref\|NP_001701.1\| | 8 | 3.0% | complement factor B preproprotein; C3 proactivator; C3 proaccelerator; glycine-rich beta-glycoprotein; C3/C5 convertase [Homo sapiens] |
| gi\|4504001\|ref\|NP_000156.1\| | 3 | 3.4% | connexin 43; oculodentodigital dysplasia (syndactyly type III) [Homo sapiens] |
| gi\|41393595\|ref\|NP_150094.3\| | 4 | 0.5% | CUB and Sushi multiple domains 1 [Homo sapiens] |
| gi\|4503327\|ref\|NP_000389.1\| | 46 | 37.2% | cytochrome b5 reductase membrane-bound isoform [Homo sapiens] |
| gi\|17981856\|ref\|NP_536846.1\| | 19 | 16.3% | cytochrome c oxidase subunit II [Homo sapiens] |
| gi\|17981859\|ref\|NP_536849.1\| | 23 | 18.1% | cytochrome c oxidase subunit III [Homo sapiens] |
| gi\|17999528\|ref\|NP_004364.2\| | 8 | 29.4% | cytochrome c oxidase subunit VIa polypeptide 1 precursor; cytochrome C oxidase subunit VIa homolog [Homo sapiens] |
| gi\|6005737\|ref\|NP_009184.1\| | 3 | 2.5% | cytochrome P450, family 4, subfamily F, polypeptide 8; cytochrome P450, subfamily IVF, polypeptide 8; microsomal monooxygenase; flavoprotein-linked monooxygenase [Homo sapiens] |
| gi\|27881482\|ref\|NP_055129.2\| | 4 | 1.3% | DEAD/H (Asp-Glu-Ala-Asp/His) box polypeptide RIG-I; RNA helicase [Homo sapiens] |
| gi\|31415870\|ref\|NP_004938.1\| | 4 | 1.0% | dedicator of cytokinesis 3; presenilin-binding protein; dedicator of cyto-kinesis 3; modifier of cell adhesion [Homo sapiens] |
| gi\|44889960\|ref\|NP_982272.1\| | 6 | 0.7% | dedicator of cytokinesis 8; 1200017A24Rik [Homo sapiens] |
| gi\|47587796\|ref\|NP_004138.1\| | 3 | 3.0% | developmentally regulated GTP binding protein 1; neural precursor cell expressed, developmentally down-regulated 3; developmentally regulated GTP-binding protein 1 [Homo sapiens] |
| gi\|4503373\|ref\|NP_000101.1\| | 3 | 1.5% | dihydropyrimidine dehydrogenase [Homo sapiens] |
| gi\|18765696\|ref\|NP_001927.2\| | 4 | 1.6% | dipeptidylpeptidase VI isoform 2; dipeptidylpeptidase VI; dipeptidyl aminopeptidase IV-related protein [Homo sapiens] |
| gi\|4505939\|ref\|NP_000928.1\| | 11 | 0.7% | DNA directed RNA polymerase II polypeptide A; polymerase (RNA) II (DNA directed) polypeptide A (220kD); DNA-directed RNA polymerase II largest subunit, RNA polymerase II 220 kd subunit [Homo sapiens] |

FIG. 9E Alphabetically Sorted List of Platelet Proteins

| Locus | Count | Coverage | Descriptive Name |
|---|---|---|---|
| gi\|17388799\|ref\|NP_490647.1\| | 5 | 8.0% | DnaJ (Hsp40) homolog, subfamily B, member 6 isoform a; heat shock protein J2 [Homo sapiens] |
| gi\|20070197\|ref\|NP_005207.2\| | 3 | 6.6% | dolichyl-diphosphooligosaccharide-protein glycosyltransferase [Homo sapiens] |
| gi\|13876382\|ref\|NP_001363.1\| | 3 | 0.3% | dynein, axonemal, heavy polypeptide 9 isoform 2; dynein, axonemal, light intermediate chain 1; dynein, axonemal, heavy polypeptide 17-like; ciliary dynein heavy chain [Homo sapiens] |
| gi\|42659582\|ref\|XP_370652.2\| | 3 | 0.4% | dynein, cytoplasmic, heavy polypeptide 2 [Homo sapiens] |
| gi\|40255035\|ref\|NP_004424.2\| | 3 | 3.5% | E74-like factor 3 (ets domain transcription factor, epithelial-specific); E74-like factor 3 (ets domain transcription factor); ets domain transcription factor, serine box (epithelial-specific); E74-like factor 3 (ETS domain transcription factor, serine b |
| gi\|30240932\|ref\|NP_006786.2\| | 15 | 13.3% | EH-domain containing 1; testilin [Homo sapiens] |
| gi\|7657056\|ref\|NP_055415.1\| | 21 | 12.9% | EH-domain containing 3 [Homo sapiens] |
| gi\|20452464\|ref\|NP_620411.1\| | 10 | 7.2% | endothelial cell adhesion molecule; HUEL (C4orf1)-interacting protein; 2310008D05Rik [Homo sapiens] |
| gi\|4758232\|ref\|NP_004817.1\| | 3 | 2.3% | endothelin converting enzyme-like 1; X converting enzyme [Homo sapiens] |
| gi\|4758256\|ref\|NP_004085.1\| | 4 | 6.3% | eukaryotic translation initiation factor 2, subunit 1 (alpha, 35kDa; eukaryotic translation initiation factor 2, subunit 1 (alpha, 35kD ); eukaryotic translation initiation factor 2A, elF-2-alpha [Homo sapiens] |
| gi\|4503529\|ref\|NP_001407.1\| | 3 | 3.9% | eukaryotic translation initiation factor 4A, isoform 1 [Homo sapiens] |
| gi\|4885225\|ref\|NP_005234.1\| | 3 | 2.1% | Ewing sarcoma breakpoint region 1 isoform EWS [Homo sapiens] |
| gi\|4885229\|ref\|NP_005236.1\| | 4 | 0.4% | FAT gene product [Homo sapiens] |
| gi\|13435350\|ref\|NP_077728.1\| | 4 | 4.5% | ferredoxin reductase isoform 1 precursor; adrenodoxin reductase [Homo sapiens] |
| gi\|11761629\|ref\|NP_068857.1\| | 43 | 32.8% | fibrinogen, alpha chain isoform alpha preproprotein [Homo sapiens] |
| gi\|11761631\|ref\|NP_005132.1\| | 41 | 21.2% | fibrinogen, beta chain preproprotein [Homo sapiens] |
| gi\|29789106\|ref\|NP_064456.1\| | 5 | 7.3% | fibrinogen, beta polypeptide; Fibrinogen, B beta polypeptide; Fibrinogen B beta polypeptide [Rattus norvegicus] |
| gi\|11761633\|ref\|NP_068656.1\| | 19 | 29.1% | fibrinogen, gamma chain isoform gamma-B precursor [Homo sapiens] |
| gi\|16933540\|ref\|NP_004451.2\| | 4 | 2.2% | fibroblast activation protein, alpha subunit; integral membrane serine protease; seprase [Homo sapiens] |
| gi\|28479106\|ref\|XP_129845.3\| | 22 | 2.7% | fibronectin 1 [Mus musculus] |
| gi\|16933542\|ref\|NP_002017.1\| | 47 | 5.7% | fibronectin 1 isoform 1 preproprotein; cold-insoluble globulin [Homo sapiens] |
| gi\|4503745\|ref\|NP_001447.1\| | 125 | 11.7% | filamin 1 (actin-binding protein-280); filamin 1; filamin A, alpha (actin-binding protein-280), actin-binding protein-280 [Homo sapiens] |
| gi\|38086405\|ref\|XP_207130.3\| | 122 | 9.6% | filamin, alpha [Mus musculus] |

FIG. 9F  Alphabetically Sorted List of Platelet Proteins

| Locus | Count | Coverage | Descriptive Name |
|---|---|---|---|
| gi|7019375|ref|NP_037373.1| | 3 | 1.1% | formin homology 2 domain containing 1; FH1/FH2 domain-containing protein [Homo sapiens] |
| gi|21614513|ref|NP_036322.2| | 4 | 3.3% | formyltetrahydrofolate dehydrogenase isoform a [Homo sapiens] |
| gi|30410722|ref|NP_004471.3| | 13 | 4.3% | fucosyltransferase 8 isoform b; glycoprotein 6-alpha-L-fucosyltransferase; GDP-fucose--glycoprotein fucosyltransferase; GDP-L-Fuc:N-acetyl-beta-D-glucosaminide alpha1,6-fucosyltransferase; alpha1-6FucT [Homo sapiens] |
| gi|19913373|ref|NP_079536.2| | 10 | 11.0% | G6B protein isoform G6b-A precursor; G6B protein; immunoglobulin receptor [Homo sapiens] |
| gi|10834966|ref|NP_000395.1| | 7 | 3.4% | galactosidase, beta 1 [Homo sapiens] |
| gi|38044288|ref|NP_937895.1| | 13 | 10.5% | gelsolin isoform b [Homo sapiens] |
| gi|4885279|ref|NP_005260.1| | 3 | 1.3% | glioma-associated oncogene homolog [Homo sapiens] |
| gi|4504135|ref|NP_000829.1| | 4 | 1.0% | glutamate receptor, metabotropic 1 [Homo sapiens] |
| gi|4504145|ref|NP_000834.1| | 3 | 1.6% | glutamate receptor, metabotropic 6 precursor [Homo sapiens] |
| gi|4504149|ref|NP_000836.1| | 3 | 1.4% | glutamate receptor, metabotropic 8 precursor [Homo sapiens] |
| gi|5031707|ref|NP_005503.1| | 6 | 6.6% | glycoprotein A repetitions predominant precursor; garpin [Homo sapiens] |
| gi|4504073|ref|NP_000398.1| | 7 | 13.1% | glycoprotein Ib beta polypeptide precursor [Homo sapiens] |
| gi|4758460|ref|NP_004479.1| | 6 | 12.5% | glycoprotein V (platelet) [Homo sapiens] |
| gi|37574620|ref|NP_057447.3| | 8 | 4.4% | glycoprotein VI (platelet); platelet glycoprotein VI [Homo sapiens] |
| gi|6996010|ref|NP_002038.1| | 3 | 1.8% | glycyl-tRNA synthetase; GlyRS; glycine tRNA ligase; Charcot-Marie-Tooth neuropathy, neuronal type, D [Homo sapiens] |
| gi|4504143|ref|NP_000833.1| | 4 | 1.4% | GRM5 gene product [Homo sapiens] |
| gi|4503991|ref|NP_002050.1| | 3 | 4.1% | growth hormone 2 isoform 1; hGH-V; placental-specific growth hormone; placenta-specific growth hormone [Homo sapiens] |
| gi|4504041|ref|NP_002061.1| | 5 | 9.6% | guanine nucleotide binding protein (G protein), alpha inhibiting activity polypeptide 2; Guanine nucleotide-binding protein (G protein), q polypeptide [Homo sapiens] |
| gi|40254462|ref|NP_002063.2| | 9 | 10.3% | guanine nucleotide binding protein (G protein), alpha-inhibiting [Homo sapiens] |
| gi|4557026|ref|NP_003913.1| | 4 | 0.3% | guanine nucleotide exchange factor p532 [Homo sapiens] |
| gi|4504517|ref|NP_001531.1| | 18 | 22.9% | heat shock 27kDa protein 1; heat shock 27kD protein 1 [Homo sapiens] |
| gi|41148814|ref|XP_175125.4| | 3 | 0.5% | hemicentin-2 [Homo sapiens] |
| gi|40254952|ref|NP_068600.2| | 5 | 1.9% | heparanase 2; heparanase-like protein; heparanase 3 [Homo sapiens] |
| gi|5729873|ref|NP_006656.1| | 17 | 9.6% | heparanase; heparanase-1 [Homo sapiens] |
| gi|15991827|ref|NP_277031.1| | 3 | 4.1% | hexokinase 1 isoform HKI-R; brain form hexokinase [Homo sapiens] |
| gi|24497526|ref|NP_002135.2| | 3 | 3.7% | homeo box B1; homeobox protein Hox-B1; homeo box 2I [Homo sapiens] |

FIG. 9G Alphabetically Sorted List of Platelet Proteins

| Locus | Count | Coverage | Descriptive Name |
|---|---|---|---|
| gi\|4504389\|ref\|NP_002105.1\| | 3 | 0.6% | human immunodeficiency virus type I enhancer binding protein 1; human immunodeficiency virus type I enhancer-binding protein 1; major histocompatibility complex binding protein 1; positive regulatory domain II binding factor 1; zinc finger protein 40 [Homo sapiens] |
| gi\|30410779\|ref\|NP_054878.3\| | 6 | 0.7% | huntingtin interacting protein B isoform 1; huntingtin interacting protein HYPB; huntingtin interacting protein 1; HSPC069 [Homo sapiens] |
| gi\|30410777\|ref\|NP_036403.1\| | 6 | 0.9% | huntingtin interacting protein B isoform 2; huntingtin interacting protein HYPB; huntingtin interacting protein 1; HSPC069 [Homo sapiens] |
| gi\|4758504\|ref\|NP_004484.1\| | 6 | 15.7% | hydroxyacyl-Coenzyme A dehydrogenase, type II; type 10 17b-HSD; type 10 17beta-hydroxysteroid dehydrogenase [Homo sapiens] |
| gi\|8923001\|ref\|NP_060864.1\| | 16 | 4.6% | hypothetical protein FLJ11342 [Homo sapiens] |
| gi\|31542673\|ref\|NP_078867.2\| | 14 | 23.4% | hypothetical protein FLJ11749 [Homo sapiens] |
| gi\|40255247\|ref\|NP_078856.3\| | 4 | 1.8% | hypothetical protein FLJ13119 [Homo sapiens] |
| gi\|41191427\|ref\|XP_371586.1\| | 3 | 1.0% | hypothetical protein FLJ25415 [Homo sapiens] |
| gi\|21389359\|ref\|NP_653185.1\| | 3 | 3.8% | hypothetical protein FLJ30525 [Homo sapiens] |
| gi\|40255223\|ref\|NP_848599.2\| | 3 | 0.9% | hypothetical protein FLJ40427 [Homo sapiens] |
| gi\|41190466\|ref\|XP_371501.1\| | 3 | 0.9% | hypothetical protein MGC22014 [Homo sapiens] |
| gi\|31543181\|ref\|NP_076933.2\| | 13 | 2.4% | hypothetical protein MGC3265 [Homo sapiens] |
| gi\|10835023\|ref\|NP_002213.1\| | 7 | 1.3% | inositol 1,4,5-triphosphate receptor, type 1 [Homo sapiens] |
| gi\|4504745\|ref\|NP_000410.1\| | 214 | 23.3% | integrin alpha 2b precursor; platelet fibrinogen receptor, alpha subunit; platelet-specific antigen BAK [Homo sapiens] |
| gi\|4557675\|ref\|NP_000201.1\| | 7 | 2.5% | integrin alpha chain, alpha 6 [Homo sapiens] |
| gi\|4557677\|ref\|NP_000203.1\| | 9 | 7.5% | integrin beta chain, beta 3 precursor; platelet glycoprotein IIIa precursor [Homo sapiens] |
| gi\|6007851\|ref\|NP_002199.2\| | 6 | 1.0% | integrin, alpha E (antigen CD103, human mucosal lymphocyte antigen 1; alpha polypeptide); antigen CD103, human mucosal lymphocyte antigen 1, alpha polypeptide [Homo sapiens] |
| gi\|4758606\|ref\|NP_004508.1\| | 30 | 13.9% | integrin-linked kinase [Homo sapiens] |
| gi\|24308115\|ref\|NP_056464.1\| | 3 | 5.1% | interferon regulatory factor 2 binding protein 1 [Homo sapiens] |
| gi\|4504643\|ref\|NP_001550.1\| | 4 | 2.2% | interleukin 12 receptor, beta 2 precursor; IL-12 receptor beta 2; interleukin-12 receptor beta-2 chain [Homo sapiens] |
| gi\|28178832\|ref\|NP_002159.2\| | 12 | 11.3% | isocitrate dehydrogenase 2 (NADP+), mitochondrial precursor; isocitrate dehydrogenase, mitochondrial; oxalosuccinate decarboxylase; NADP+-specific ICDH [Homo sapiens] |
| gi\|14149680\|ref\|NP_056107.1\| | 9 | 2.8% | KIAA0747 protein [Homo sapiens] |
| gi\|42655919\|ref\|XP_375848.1\| | 7 | 2.7% | KIAA0792 gene product [Homo sapiens] |

FIG. 9H Alphabetically Sorted List of Platelet Proteins

| Locus | Count | Coverage | Descriptive Name |
|---|---|---|---|
| gi|42655960|ref|XP_375825.1| | 5 | 0.9% | kinesin family member 14 [Homo sapiens] |
| gi|31077094|ref|NP_071358.1| | 3 | 3.2% | LAG1 longevity assurance homolog 2 isoform 1; L3 pigment; tumor metastasis-suppressor [Homo sapiens] |
| gi|38788416|ref|NP_005550.2| | 5 | 0.7% | laminin, alpha 1 precursor [Homo sapiens] |
| gi|9845496|ref|NP_002283.2| | 8 | 1.3% | laminin, beta 2 precursor; laminin S [Homo sapiens] |
| gi|11024664|ref|NP_067598.1| | 5 | 1.6% | LanC (bacterial lantibiotic synthetase component C)-like 1; transforming growth factor-beta (TGF-beta) masking protein large subunit; latent transforming growth factor beta binding protein 1 [Rattus norvegicus] |
| gi|46249412|ref|NP_000618.2| | 7 | 3.8% | latent transforming growth factor beta binding protein 1 LTBP-1S; TGF-beta1-BP-1 [Homo sapiens] |
| gi|4505017|ref|NP_002327.1| | 3 | 2.9% | low density lipoprotein receptor-related protein 6; low density lipoprotein-related protein 6 [Homo sapiens] |
| gi|6678718|ref|NP_032540.1| | 3 | 1.7% | low density lipoprotein receptor-related protein 6; low density lipoprotein-related protein 6 [Mus musculus] |
| gi|6806919|ref|NP_004516.1| | 5 | 0.5% | low density lipoprotein-related protein 2; megalin; calcium sensor protein; Heymann nephritis antigen homolog [Homo sapiens] |
| gi|16904381|ref|NP_006717.1| | 5 | 1.2% | LPS-responsive vesicle trafficking, beach and anchor containing; vesicle trafficking, beach and anchor containing; cell division cycle 4-like [Homo sapiens] |
| gi|4504957|ref|NP_002285.1| | 6 | 4.4% | lysosomal-associated membrane protein 2 precursor; Lysosome-associated membrane protein-2 [Homo sapiens] |
| Contaminant_gi|7463016|pir||S77957 | 18 | 23.4% | lysyl endopeptidase (EC 3.4.21.50) - Lysobacter enzymogenes |
| gi|32307144|ref|NP_000293.2| | 4 | 1.7% | lysyl hydroxylase precursor; lysine hydroxylase [Homo sapiens] |
| gi|6677765|ref|NP_033100.1| | 4 | 1.5% | macrophage stimulating 1 receptor (c-met-related tyrosine kinase); friend virus susceptibility 2; receptor protein tyrosine kinase, c-met-related [Mus musculus] |
| gi|4759060|ref|NP_004790.1| | 6 | 1.3% | MAD, mothers against decapentaplegic homolog (Drosophila) interacting protein; receptor activation anchor isoform 3; Smad anchor for receptor activation; MAD (mothers against decapentaplegic, Drosophila) homolog interacting protein, receptor activation an |
| gi|24797067|ref|NP_002107.3| | 4 | 14.0% | major histocompatibility complex, class I, A precursor; HLA-A1 class I antigen [Homo sapiens] |
| gi|19913412|ref|NP_005106.2| | 3 | 2.5% | major vault protein [Homo sapiens] |
| gi|4505245|ref|NP_002429.1| | 6 | 1.2% | mannose receptor C type 1 precursor; mannose receptor; macrophage mannose receptor [Homo sapiens] |

FIG. 9I  Alphabetically Sorted List of Platelet Proteins

| Locus | Count | Coverage | Descriptive Name |
|---|---|---|---|
| gi\|33188445\|ref\|NP_036222.3\| | 4 | 0.6% | microfilament and actin filament cross-linker protein isoform a; 620 kDa actin binding protein; actin cross-linking factor; macrophin 1; trabeculin-alpha; actin cross-linking family protein 7 [Homo sapiens] |
| gi\|21735621\|ref\|NP_005909.2\| | 4 | 6.2% | mitochondrial malate dehydrogenase precursor [Homo sapiens] |
| gi\|4505257\|ref\|NP_002435.1\| | 7 | 10.1% | moesin [Homo sapiens] |
| gi\|4505197\|ref\|NP_003473.1\| | 3 | 0.3% | myeloid/lymphoid or mixed-lineage leukemia 2; ALL1-related gene [Homo sapiens] |
| gi\|20891813\|ref\|XP_147228.1\| | 44 | 4.8% | myosin heavy chain 11, smooth muscle [Mus musculus] |
| gi\|33356170\|ref\|NP_004136.2\| | 4 | 0.6% | myosin IXB [Homo sapiens] |
| gi\|16950611\|ref\|NP_444253.1\| | 6 | 1.9% | myosin light chain kinase isoform 1; myosin light chain kinase [Homo sapiens] |
| gi\|7669506\|ref\|NP_005954.2\| | 14 | 1.5% | myosin, heavy polypeptide 1, skeletal muscle, adult; myosin heavy chain IIx/d [Homo sapiens] |
| gi\|41406064\|ref\|NP_005955.1\| | 42 | 4.4% | myosin, heavy polypeptide 10, non-muscle; myosin heavy chain, nonmuscle type B; cellular myosin heavy chain, type B [Homo sapiens] |
| gi\|4557773\|ref\|NP_000248.1\| | 10 | 1.2% | myosin, heavy polypeptide 7, cardiac muscle, beta [Homo sapiens] |
| gi\|12667788\|ref\|NP_002464.1\| | 364 | 24.9% | myosin, heavy polypeptide 9, non-muscle [Homo sapiens] |
| gi\|6681764\|ref\|NP_004993.1\| | 4 | 8.5% | NADH dehydrogenase (ubiquinone) 1 alpha subcomplex, 9, 39kDa; NADH dehydrogenase (ubiquinone) 1 alpha subcomplex, 9 (39kD); NADH dehydrogenase (ubiquinone) Fe-S protein 2-like (NADH-coenzyme Q reductase) [Homo sapiens] |
| gi\|4758786\|ref\|NP_004541.1\| | 3 | 5.4% | NADH dehydrogenase (ubiquinone) Fe-S protein 2, 49kDa (NADH-coenzyme Q reductase); NADH-ubiquinone oxidoreductase Fe-S protein 2; NADH dehydrogenase (ubiquinone) Fe-S protein 2 (49kD) (NADH-coenzyme Q reductase) [Homo sapiens] |
| gi\|17981863\|ref\|NP_536853.1\| | 4 | 3.8% | NADH dehydrogenase subunit 5 [Homo sapiens] |
| gi\|4758794\|ref\|NP_004534.1\| | 6 | 0.4% | nebulin [Homo sapiens] |
| gi\|23097308\|ref\|NP_149062.1\| | 4 | 0.2% | nesprin 1 isoform longer; synaptic nuclei expressed gene 1; nesprin 1; enaptin [Homo sapiens] |
| gi\|41393547\|ref\|NP_056993.2\| | 3 | 2.6% | neuroblastoma-amplified protein [Homo sapiens] |
| gi\|22267436\|ref\|NP_056284.1\| | 12 | 27.9% | nipsnap homolog 3A [Homo sapiens] |
| gi\|4504131\|ref\|NP_000827.1\| | 3 | 1.0% | N-methyl-D-aspartate receptor subunit 2D precursor; estrogen receptor binding CpG island [Homo sapiens] |
| gi\|25777608\|ref\|NP_078894.2\| | 5 | 5.1% | NOD9 protein isoform 1 [Homo sapiens] |
| gi\|33946327\|ref\|NP_005076.3\| | 3 | 0.8% | nucleoporin 214kDa; nuclear pore complex protein Nup214, CAN protein, putative oncogene; p250 [Homo sapiens] |
| gi\|40255314\|ref\|NP_443075.1\| | 7 | 0.3% | obscurin, cytoskeletal calmodulin and titin-interacting RhoGEF [Homo sapiens] |
| Contaminant_NRL_1MCOH | 13 | 17.3% | owl\|\| Immunoglobulin g1 (igg1) (mcg) with a hinge deletion, chain H |

FIG. 9J Alphabetically Sorted List of Platelet Proteins

| Locus | Count | Coverage | Descriptive Name |
|---|---|---|---|
| gi\|20143480\|ref\|NP_003809.1\| | 6 | 5.6% | phosphatidate cytidylyltransferase 2; CDP-diglyceride synthetase 2; CDP-diglyceride pyrophosphorylase 2; CDP-diglyceride diphosphorylase 2; CDP-DAG synthase 2; CDP-DG synthetase 2; CTP:phosphatidate cytidylyltransferase 2; CDP-diacylglycerol synthase 2 [Homo sapiens] |
| gi\|4505799\|ref\|NP_002636.1\| | 3 | 0.8% | phosphoinositide-3-kinase, class 2, alpha polypeptide; C2-containing phosphatidylinositol kinase; PI3K-C2alpha [Homo sapiens] |
| gi\|4505779\|ref\|NP_002628.1\| | 3 | 1.1% | phosphorylase kinase, alpha 1 (muscle); Phosphorylase kinase, muscle, alpha polypeptide; phosphorylase kinase, alpha 1 (muscle), muscle glycogenosis [Homo sapiens] |
| gi\|42476166\|ref\|NP_002854.2\| | 6 | 3.5% | phosphorylase, glycogen; liver (Hers disease, glycogen storage disease type VI); Phosphorylase, glycogen, liver [Homo sapiens] |
| gi\|4505881\|ref\|NP_000292.1\| | 3 | 3.0% | plasminogen [Homo sapiens] |
| gi\|24307907\|ref\|NP_006207.1\| | 11 | 18.6% | plasminogen activator inhibitor type 1, member 2; protease inhibitor 7 (protease nexin I); glial-derived nexin 1; glial-derived neurite promoting factor [Homo sapiens] |
| gi\|45269135\|ref\|NP_000164.2\| | 23 | 4.7% | platelet glycoprotein Ib alpha polypeptide precursor [Homo sapiens] |
| gi\|4505879\|ref\|NP_002655.1\| | 4 | 7.1% | pleckstrin; p47 [Homo sapiens] |
| gi\|28933451\|ref\|NP_055918.1\| | 3 | 0.7% | plexin D1 [Homo sapiens] |
| gi\|33359213\|ref\|NP_000287.2\| | 4 | 0.3% | polycystin 1 precursor [Homo sapiens] |
| gi\|7305389\|ref\|NP_038658.1\| | 3 | 0.4% | polycystin-1 [Mus musculus] |
| gi\|5729875\|ref\|NP_006658.1\| | 5 | 14.9% | progesterone receptor membrane component 1; progesterone binding protein [Homo sapiens] |
| gi\|4505981\|ref\|NP_002695.1\| | 16 | 11.7% | pro-platelet basic protein precursor; pro-platelet basic protein; connective tissue-activating peptide III; beta-thromboglobulin; neutrophil-activating peptide-2; CXC chemokine ligand 7; small inducible cytokine subfamily B, member 7; thromboglobulin, bet |
| gi\|181049067\|ref\|NP_000953.2\| | 51 | 12.5% | prostaglandin-endoperoxide synthase 1 isoform 1 precursor; prostaglandin G/H synthase and cyclooxygenase [Homo sapiens] |
| gi\|5031973\|ref\|NP_005733.1\| | 25 | 12.7% | protein disulfide isomerase-related protein [Homo sapiens] |
| gi\|5453976\|ref\|NP_006248.1\| | 3 | 2.0% | protein kinase C, theta [Homo sapiens] |
| gi\|18860904\|ref\|NP_002836.2\| | 3 | 0.8% | protein tyrosine phosphatase, receptor type, M precursor; protein tyrosine phosphatase, receptor type, mu polypeptide; protein tyrosine phosphatase mu precursor [Homo sapiens] |
| gi\|19743931\|ref\|NP_573438.1\| | 3 | 0.9% | protein tyrosine phosphatase, receptor type, U isoform 2 precursor; protein tyrosine phosphatase J; protein tyrosine phosphatase receptor omicron; pi R-PTP-Psi [Homo sapiens] |

FIG. 9K Alphabetically Sorted List of Platelet Proteins

| Locus | Count | Coverage | Descriptive Name |
|---|---|---|---|
| gi\|19743935\|ref\|NP_005695.2\| | 5 | 1.4% | protein tyrosine phosphatase, receptor type, U isoform 3 precursor; protein tyrosine phosphatase J; protein tyrosine phosphatase receptor omicron; pi R-PTP-Psi [Homo sapiens] |
| gi\|8393916\|ref\|NP_059074.1\| | 3 | 1.3% | protocadherin 12; protocadherin 14; VE-cadherin-2; vascular endothelial cadherin-2 [Mus musculus] |
| gi\|16933557\|ref\|NP_003728.1\| | 4 | 1.5% | protocadherin 16 precursor; fibroblast cadherin FIB1; fibroblast cadherin 1; dachsous homologue [Homo sapiens] |
| gi\|11128043\|ref\|NP_061744.1\| | 3 | 3.3% | protocadherin gamma subfamily A, 9 isoform 1 precursor [Homo sapiens] |
| gi\|13491166\|ref\|NP_055491.1\| | 3 | 1.3% | pumilio homolog 1 [Homo sapiens] |
| gi\|4505545\|ref\|NP_002549.1\| | 5 | 7.3% | purinergic receptor P2X1, P2X1 receptor; P2X purinoceptor 1; ATP receptor, P2X receptor, subunit 1 [Homo sapiens] |
| gi\|33286418\|ref\|NP_002645.3\| | 27 | 9.8% | pyruvate kinase 3 isoform 1; thyroid hormone-binding protein, cytosolic; PK, muscle type; OPA-interacting protein 3 [Homo sapiens] |
| gi\|45387955\|ref\|NP_991330.1\| | 30 | 17.8% | QIL1 protein [Homo sapiens] |
| gi\|4506467\|ref\|NP_002897.1\| | 6 | 4.3% | radixin [Homo sapiens] |
| gi\|6382079\|ref\|NP_006258.2\| | 3 | 0.4% | RAN binding protein 2; nucleoporin 358; nuclear pore complex protein Nup358; P270 [Homo sapiens] |
| gi\|7661678\|ref\|NP_056461.1\| | 13 | 17.9% | RAP1B, member of RAS oncogene family; K-REV; RAS-related protein RAP1B [Homo sapiens] |
| gi\|38201692\|ref\|NP_031394.2\| | 7 | 4.9% | RAS p21 protein activator 3; GTPase activating protein III; Ins(1,3,4,5)P4-binding protein; inositol 1,3,4,5-tetrakisphosphate-binding protein [Homo sapiens] |
| gi\|6912638\|ref\|NP_036557.1\| | 42 | 18.4% | ras suppressor protein 1 isoform 1 [Homo sapiens] |
| gi\|9845511\|ref\|NP_008839.2\| | 7 | 12.5% | ras-related C3 botulinum toxin substrate 1 isoform Rac1; rho family, small GTP binding protein Rac1 [Homo sapiens] |
| gi\|6005854\|ref\|NP_009204.1\| | 13 | 5.0% | repressor of estrogen receptor activity; B-cell associated protein [Homo sapiens] |
| gi\|24431933\|ref\|NP_722550.1\| | 40 | 16.1% | reticulon 4; neuroendocrine-specific protein C homolog; neurite outgrowth inhibitor; foocen; nogo protein; reticulon 5; My043 protein; neurite growth inhibitor 220 [Homo sapiens] |
| gi\|4506675\|ref\|NP_002941.1\| | 11 | 5.4% | ribophorin I [Homo sapiens] |
| gi\|35493916\|ref\|NP_002942.2\| | 6 | 2.9% | ribophorin II precursor; dolichyl-diphosphooligosaccharide--protein glycosyltransferase 63 kDa subunit [Homo sapiens] |
| gi\|30425250\|ref\|NP_780706.1\| | 28 | 27.4% | RIKEN cDNA 4732495G21 gene [Mus musculus] |
| gi\|5730023\|ref\|NP_006657.1\| | 3 | 4.3% | RuvB-like 2; erythrocyte cytosolic protein, 51-KD; TBP-interacting protein, 48-KD; Reptin52 [Homo sapiens] |
| gi\|37704386\|ref\|NP_001027.2\| | 4 | 0.3% | ryanodine receptor 3 [Homo sapiens] |

FIG. 9L. Alphabetically Sorted List of Platelet Proteins

| Locus | Count | Coverage | Descriptive Name |
|---|---|---|---|
| gi|28373103|ref|NP_005164.2| | 6 | 6.8% | sarco/endoplasmic reticulum Ca2+ -ATPase isoform a; ATPase, Ca(2+)-transporting, ubiquitous; sarcoplasmic/endoplasmic reticulum calcium ATPase 3; SR Ca(2+)-ATPase 3; calcium pump 3; adenosine triphosphatase, calcium; sarco/endoplasmic reticulum Ca2+ -ATPa |
| gi|4502133|ref|NP_001630.1| | 4 | 8.5% | serum amyloid P component precursor; pentaxin-related; 9.5S alpha-1-glycoprotein [Homo sapiens] |
| gi|34881683|ref|XP_228661.2| | 3 | 5.1% | similar to butyrate response factor 2; EGF-response factor 2; zinc finger protein, C3H type, 36-like 2 [Rattus norvegicus] |
| gi|34881882|ref|XP_238167.2| | 121 | 10.0% | similar to FLJ00343 protein [Rattus norvegicus] |
| gi|34868486|ref|XP_237706.2| | 3 | 3.7% | similar to Heat shock cognate 71 kDa protein [Rattus norvegicus] |
| gi|20664524|ref|XP_146397.1| | 7 | 0.6% | similar to hypothetical protein [Mus musculus] |
| gi|41203848|ref|XP_370781.1| | 11 | 4.7% | similar to Ig alpha-2 chain C region [Homo sapiens] |
| gi|34877017|ref|XP_214261.2| | 20 | 1.4% | similar to KIAA1290 protein [Rattus norvegicus] |
| gi|42656626|ref|XP_290985.4| | 5 | 3.3% | similar to LIM and senescent cell antigen-like domains 1 [Homo sapiens] |
| gi|34857644|ref|XP_230493.2| | 3 | 1.5% | similar to mKIAA1300 protein [Rattus norvegicus] |
| gi|34854180|ref|XP_227084.2| | 3 | 5.5% | similar to nicotinamide nucleotide transhydrogenase [Rattus norvegicus] |
| gi|42659647|ref|XP_377240.1| | 3 | 6.8% | similar to peptidylprolyl isomerase A (cyclophilin A) [Homo sapiens] |
| gi|29736622|ref|XP_293924.1| | 42 | 22.3% | similar to RIKEN cDNA 4732495G21 gene [Homo sapiens] |
| gi|30581135|ref|NP_006297.2| | 4 | 1.2% | SMC1 structural maintenance of chromosomes 1-like 1; segregation of mitotic chromosomes 1 [Homo sapiens] |
| gi|13124875|ref|NP_074035.1| | 44 | 4.7% | smooth muscle myosin heavy chain 11 isoform SM2 [Homo sapiens] |
| gi|5730067|ref|NP_006653.1| | 5 | 0.9% | Snf2-related CBP activator protein [Homo sapiens] |
| gi|5902090|ref|NP_008862.1| | 21 | 8.7% | solute carrier family 2 (facilitated glucose transporter), member 3; GLUCOSE TRANSPORTER TYPE 3, BRAIN [Homo sapiens] |
| gi|27764863|ref|NP_001627.1| | 3 | 8.1% | solute carrier family 25, member A6; adenine nucleotide translocator 3; ADP,ATP carrier protein, liver isoform T2; ADP/ATP translocase 3; ADP/ATP translocator of liver [Homo sapiens] |
| gi|13236579|ref|NP_077306.1| | 4 | 3.8% | solute carrier family 27 member 3; fatty acid transport protein 3 [Homo sapiens] |
| gi|4507021|ref|NP_000333.1| | 12 | 4.5% | solute carrier family 4, anion exchanger, member 1 (erythrocyte membrane protein band 3, Diego blood group); anion exchange protein 1; Waldner blood group [Homo sapiens] |
| gi|12225240|ref|NP_055951.1| | 4 | 0.9% | stabilin 1 [Homo sapiens] |
| gi|38016911|ref|NP_004090.4| | 84 | 41.3% | stomatin isoform a; erythrocyte membrane protein band 7.2 (stomatin) [Homo sapiens] |
| gi|10864011|ref|NP_067022.1| | 9 | 4.2% | sulfide dehydrogenase like; sulfide dehydrogenase like (yeast) [Homo sapiens] |
| gi|10835187|ref|NP_000627.1| | 162 | 24.3% | superoxide dismutase 2, mitochondrial [Homo sapiens] |
| gi|5902128|ref|NP_008880.1| | 8 | 5.1% | syntaxin binding protein 2; Hunc18b [Homo sapiens] |

FIG. 9M  Alphabetically Sorted List of Platelet Proteins

| Locus | Count | Coverage | Descriptive Name |
|---|---|---|---|
| gi\|16753233\|ref\|NP_006280.2\| | 65 | 7.6% | talin 1 [Homo sapiens] |
| gi\|21536371\|ref\|NP_009041.2\| | 4 | 0.6% | telomerase-associated protein 1; telomerase protein component 1 [Homo sapiens] |
| gi\|7110725\|ref\|NP_035710.1\| | 72 | 12.4% | thrombospondin 1 [Mus musculus] |
| gi\|40317626\|ref\|NP_003237.2\| | 98 | 20.0% | thrombospondin 1 precursor [Homo sapiens] |
| gi\|4507383\|ref\|NP_001052.1\| | 24 | 7.5% | thromboxane A synthase 1 (platelet, cytochrome P450, family 5, subfamily A) isoform TXS-I; thromboxane A synthase 1 (platelet, cytochrome P450, subfamily V); TXA synthase [Homo sapiens] |
| gi\|19747267\|ref\|NP_596869.1\| | 12 | 0.1% | titin isoform N2-A; connectin; CMH9, included; cardiomyopathy, dilated 1G (autosomal dominant) [Homo sapiens] |
| gi\|20143918\|ref\|NP_597676.1\| | 11 | 0.1% | titin isoform novex-1; connectin; CMH9, included; cardiomyopathy, dilated 1G (autosomal dominant) [Homo sapiens] |
| gi\|10863873\|ref\|NP_000651.1\| | 9 | 10.0% | transforming growth factor, beta 1 (Camurati-Engelmann disease); diaphyseal dysplasia 1, progressive (Camurati-Engelmann disease) [Homo sapiens] |
| gi\|40255041\|ref\|NP_006818.2\| | 4 | 10.0% | transmembrane trafficking protein [Homo sapiens] |
| gi\|4507411\|ref\|NP_000347.1\| | 3 | 1.3% | treacle; Treacher Collins-Franceschetti syndrome protein 1 [Homo sapiens] |
| gi\|30794266\|ref\|NP_835468.1\| | 7 | 7.7% | triggering receptor expressed on myeloid cells-like 1; TREM-like transcript 1 [Homo sapiens] |
| gi\|21702733\|ref\|NP_065898.1\| | 8 | 1.0% | trinucleotide repeat containing 6; EDIE; GW182 autoantigen [Homo sapiens] |
| gi\|14192925\|ref\|NP_062004.1\| | 5 | 19.1% | tropomyosin 1 (alpha) [Homo sapiens] |
| gi\|24119203\|ref\|NP_705935.1\| | 8 | 25.0% | tropomyosin 3 [Homo sapiens] |
| gi\|4507651\|ref\|NP_003281.1\| | 6 | 27.4% | tropomyosin 4 [Homo sapiens] |
| gi\|34147630\|ref\|NP_003312.3\| | 9 | 16.3% | Tu translation elongation factor, mitochondrial [Homo sapiens] |
| gi\|6715610\|ref\|NP_003313.2\| | 3 | 2.8% | tubby like protein 1; Tubby-like protein-1 [Homo sapiens] |
| gi\|10938008\|ref\|NP_066399.1\| | 3 | 0.8% | tuberous sclerosis 2 isoform 2; tuberin; tuberin isoform 1; tuberin isoform 2; tuberin isoform 3 [Homo sapiens] |
| gi\|14389309\|ref\|NP_116093.1\| | 130 | 24.9% | tubulin alpha 6 [Homo sapiens] |
| gi\|17921989\|ref\|NP_005991.1\| | 138 | 18.3% | tubulin, alpha 1; testis-specific alpha tubulin; tubulin alpha-1 chain [Homo sapiens] |
| gi\|17986283\|ref\|NP_006000.2\| | 59 | 24.8% | tubulin, alpha 3; tubulin, alpha, brain-specific; hum-a-tub1; hum-a-tub2 [Homo sapiens] |
| gi\|13376539\|ref\|NP_079295.1\| | 77 | 21.6% | tubulin, alpha 4 [Homo sapiens] |
| gi\|9507215\|ref\|NP_061816.1\| | 124 | 15.8% | tubulin, alpha 8; tubulin, alpha-like 2 [Homo sapiens] |
| gi\|5174735\|ref\|NP_006079.1\| | 40 | 16.9% | tubulin, beta, 2 [Homo sapiens] |
| gi\|21735625\|ref\|NP_663723.1\| | 15 | 13.9% | tyrosine 3/tryptophan 5-monooxygenase activation protein, zeta polypeptide; protein kinase C inhibitor protein-1; phospholipase A2; 14-3-3 zeta [Homo sapiens] |
| gi\|17999537\|ref\|NP_006436.2\| | 3 | 0.6% | U5 snRNP-specific protein; U5 snRNP-specific protein (220 kD), ortholog of S. cerevisiae Prp8p; precursor mRNA processing protein; splicing factor Prp8 [Homo sapiens] |

FIG. 9N Alphabetically Sorted List of Platelet Proteins

| Locus | Count | Coverage | Descriptive Name |
|---|---|---|---|
| gi|15277421|ref|NP_057420.2| | 5 | 4.4% | ubiquitin-conjugating enzyme E2, J1; non-canonical ubiquitin conjugating enzyme 1 [Homo sapiens] |
| gi|28626504|ref|NP_113659.3| | 30 | 25.3% | UNC-112 related protein 2 short form; kindlin 3 [Homo sapiens] |
| gi|16933525|ref|NP_003719.2| | 4 | 2.3% | unc5C; homolog of C. elegans transmembrane receptor Unc5; unc5 (C.elegans homolog) c [Homo sapiens] |
| gi|8923712|ref|NP_060947.1| | 4 | 3.6% | uncharacterized hypothalamus protein HARP11 [Homo sapiens] |
| gi|42544121|ref|NP_060154.3| | 7 | 0.9% | vacuolar protein sorting 13C protein [Homo sapiens] |
| gi|4502023|ref|NP_001617.1| | 3 | 2.7% | v-akt murine thymoma viral oncogene homolog 2; Murine thymoma viral (v-akt) homolog-2; rac protein kinase beta [Homo sapiens] |
| gi|6005942|ref|NP_009057.1| | 9 | 7.8% | valosin-containing protein; yeast Cdc48p homolog, transitional endoplasmic reticulum ATPase [Homo sapiens] |
| gi|4507877|ref|NP_003364.1| | 4 | 2.0% | vinculin isoform VCL [Homo sapiens] |
| gi|4507907|ref|NP_000543.1| | 10 | 1.5% | von Willebrand factor precursor; Coagulation factor VIII VWF (von Willebrand factor) [Homo sapiens] |
| gi|4827056|ref|NP_005103.1| | 3 | 2.6% | WD repeat-containing protein 1 isoform 2 [Homo sapiens] |
| gi|7662244|ref|NP_055463.1| | 3 | 1.1% | zinc finger DAZ interacting protein 3 [Homo sapiens] |
| gi|41147345|ref|XP_048070.3| | 4 | 0.5% | zinc finger protein 292 [Homo sapiens] |

FIG. 10

A) MAO-B (flavin-containing amine oxidase, SEQ ID NO:1)
```
   1 MSNKCDVVVV GGGISGMAAA KLLHDSGLNV VVLEARDRVG GRTYTLRNQK VKYVDLGGSY
  61 VGPTQNRILR LAKELGLETY KVNEVERLIH HVKGKSYPFR GPFPPVWNPI TYLDHNNFWR
 121 TMDDMGREIP SDAPWKAPLA EEWDNMTMKE LLDKLCWTES AKQLATLFVN LCVTAETHEV
 181 SALWFLWYVK QCGGTTRIIS TTNGGQERKF VGGSGQVSER IMDLLGDRVK LERPVIYIDQ
 241 TRENVLVETL NHEMYEAKYV ISAIPPTLGM KIHFNPPLPM MRNQMITRVP LGSVIKCIVY
 301 YKEPFWRKKD YCGTMIIDGE EAPVAYTLDD TKPEGNYAAI MGFILAHKAR KLARLTKEER
 361 LKKLCELYAK VLGSLEALEP VHYEEKNWCE EQYSGGCYTT YFPPGILTQY GRVLRQPVDR
 421 IYFAGTETAT HWSGYMEGAV EAGERAAREI LHAMGKIPED EIWQSEPESV DVPAQPITTT
 481 FLERHLPSVP GLLRLIGLTT IFSATALGFL AHKRGLLVRV
```

B) CGI-51 (sorting and assembly machinery 50kDa protein, SEQ ID NO:18)
```
   1 MGTVHARSLE PLPSSGPDFG GLGEEAEFVE VEPEAKQEIL ENKDVVVQHV HFDGLGRTKD
  61 DIIICEIGDV FKAKNLIEVM RKSHEAREKL LRLGIFRQVD VLIDTCQGDD ALPNGLDVTF
 121 EVTELRRLTG SYNTMVGNNE GSMVLGLKLP NLLGRAEKVT FQFSYGTKET SYGLSFFKPR
 181 PGNFERNFSV NLYKVTGQFP WSSLRETDRG MSAEYSFPIW KTSHTVKWEG VWRELGCLSR
 241 TASFAVRKES GHSLKSSLSH AMVIDSRNSS ILPRRGALLK VNQELAGYTG GDVSFIKEDF
 301 ELQLNKQLIF DSVFSASFWG GMLVPIGDKP SSIADRFYLG GPTSVRGFSM HSIGPQSEGD
 361 YLGGEAYWAG GLHLYTPLPF RPGQGGFGEL FRTHFFLNAG NLCNLNYGEG PKAHIRKLAE
 421 CIRWSYGAGI VLRLGNIARL ELNYCVPMGV QTGDRICDGV QFGAGIRFL
```

C) GATM (glycine amidinotransferase, SEQ ID NO:19)
```
   1 MLRVRCLRGG SRGAEAVHYI GSRLGRTLTG WVQRTFQSTQ AATASSRNSC AADDKATEPL
  61 PKDCPVSSYN EWDPLEEVIV GRAENACVPP FTIEVKANTY EKYWPFYQKQ GGHYFPKDHL
 121 KKAVAEIEEM CNILKTEGVT VRRPDPIDWS LKYKTPDFES TGLYSAMPRD ILIVVGNEII
 181 EAPMAWRSRF FEYRAYRSII KDYFHRGAKW TTAPKPTMAD ELYNQDYPIH SVEDRHKLAA
 241 QGKFVTTEFE PCFDAADFIR AGRDIFAQRS QVTNYLGIEW MRRHLAPDYR VHIISFKDPN
 301 PMHIDATFNI IGPGIVLSNP DRPCHQIDLF KKAGWTIITP PTPIIPDDHP LWMSSKWLSM
 361 NVLMLDEKRV MVDANEVPIQ KMFEKLGITT IKVNIRNANS LGGGFHCWTC DVRRRGTLQS
 421 YLD
```

D) OGDH (oxoglutarate dehydrogenase, SEQ ID NO:20)
```
   1 MFHLRTCAAK LRPLTASQTV KTFSQNRPAA ARTFQQIRCY SAPVAAEPFL SGTSSNYVEE
  61 MYCAWLENPK SVHKSWDIFF RNTNAGAPPG TAYQSPLPLS RGSLAAVAHA QSLVEAQPNV
 121 DKLVEDHLAV QSLIRAYQIR GHHVAQLDPL GILDADLDSS VPADIISSTD KLGFYGLDES
 181 DLDKVFHLPT TTFIGGQESA LPLREIIRRL EMAYCQHIGV EFMFINDLEQ CQWIRQKFET
 241 PGIMQFTNEE KRTLLARLVR STRFEEFLQR KWSSEKRFGL EGCEVLIPAL KTIIDKSSEN
 301 GVDYVIMGMP HRGRLNVLAN VIRKELEQIF CQFDSKLEAA DEGSGDVKYH LGMYHRRINR
 361 VTDRNITLSL VANPSHLEAA DPVVMGKTKA EQFYCGDTEG KKVMSILLHG DAAFAGQGIV
 421 YETFHLSDLP SYTTHGTVHV VVNNQIGFTT DPRMARSSPY PTDVARVVNA PIFHVNSDDP
 481 EAVMYVCKVA AEWRSTFHKD VVVDLVCYRR NGHNEMDEPM FTQPLMYKQI RKQKPVLQKY
 541 AELLVSQGVV NQPEYEEEIS KYDKICEEAF ARSKDEKILH IKHWLDSPWP GFFTLDGQPR
 601 SMSCPSTGLT EDILTHIGNV ASSVPVENFT IHGGLSRILK TRGEMVKNRT VDWALAEYMA
 661 FGSLLKEGIH IRLSGQDVER GTFSHRHHVL HDQNVDKRTC IPMNHLWPNQ APYTVCNSSL
 721 SEYGVLGFEL GFAMASPNAL VLWEAQFGDF HNTAQCIIDQ FICPGQAKWV RQNGIVLLLP
 781 HGMEGMGPEH SSARPERFLQ MCNDDPDVLP DLKEANFDIN QLYDCNWVVV NCSTPGNFFH
 841 VLRRQILLPF RKPLIIFTPK SLLRHPEARS SFDEMLPGTH FQRVIPEDGP AAQNPENVKR
 901 LLFCTGKVYY DLTRERKARD MVGQVAITRI EQLSPFPFDL LLKEVQKYPN AELAWCQEEH
 961 KNQGYYDVVK PRLRTTISRA KPVWYAGRDP AAAPATGNKK THLTELQRLL DTAFDLDVFK
1021 NFS
```

FIG. 10 continued

E) BZRP (peripheral benzodiazepine receptor, SEQ ID NO:21)
```
  1 MAPPWVPAMG FTLAPSLGCF VGSRFVHGEG LRWYAGLQKP SWHPPHWVLG PVWGTLYSAM
 61 GYGSYLVWKE LGGFTEKAVV PLGLYTGQLA LNWAWPPIFF GARQMGWALV DLLLVSGAAA
121 ATTVAWYQVS PLAARLLYPY LAWLAFTTTL NYCVWRDNHG WRGGRRLPE
```

F) GSN (gelsolin, SEQ ID NO:22)
```
  1 MAPHRPAPAL LCALSLALCA LSLPVRAATA SRGASQAGAP QGRVPEARPN SMVVEHPEFL
 61 KAGKEPGLQI WRVEKFDLVP VPTNLYGDFF TGDAYVILKT VQLRNGNLQY DLHYWLGNEC
121 SQDESGAAAI FTVQLDDYLN GRAVQHREVQ GFESATFLGY FKSGLKYKKG GVASGFKHVV
181 PNEVVVQRLF QVKGRRVVRA TEVPVSWESF NNGDCFILDL GNNIHQWCGS NSNRYERLKA
241 TQVSKGIRDN ERSGRARVHV SEEGTEPEAM LQVLGPKPAL PAGTEDTAKE DAANRKLAKL
301 YKVSNGAGTM SVSLVADENP FAQGALKSED CFILDHGKDG KIFVWKGKQA NTEERKAALK
361 TASDFITKMD YPKQTQVSVL PEGGETPLFK QFFKNWRDPD QTDGLGLSYL SSHIANVERV
421 PFDAATLHTS TAMAAQHGMD DDGTGQKQIW RIEGSNKVPV DPATYGQFYG GDSYIILYNY
481 RHGGRQGQII YNWQGAQSTQ DEVAASAILT AQLDEELGGT PVQSRVVQGK EPAHLMSLFG
541 GKPMIIYKGG TSREGGQTAP ASTRLFQVRA NSAGATRAVE VLPKAGALNS NDAFVLKTPS
601 AAYLWVGTGA SEAEKTGAQE LLRVLRAQPV QVAEGSEPDG FWEALGGKAA YRTSPRLKDK
661 KMDAHPPRLF ACSNKIGRFV IEEVPGELMQ EDLATDDVML LDTWDQVFVW VGKDSQEEEK
721 TEALTSAKRY IETDPANRDR RTPITVVKQG FEPPSFVGWF LGWDDDYWSV DPLDRAMAEL
781 aa
```

G) NDUFA8 (NADH dehydrogenase, SEQ ID NO:23)
```
  1 MPGIVELPTL EELKVDEVKI SSAVLKAAAH HYGAQCDKPN KEFMLCRWEE KDPRRCLEEG
 61 KLVNKCALDF FRQIKRHCAE PFTEYWTCID YTGQQLFRHC RKQQAKFDEC VLDKLGWVRP
121 DLGELSKVTK VKTDRPLPEN PYHSRPRPDP SPEIEGDLQP ATHGSRFYFW TK
```

H) GRIM19 (CELL DEATH REGULATORY PROTEIN 19, SEQ ID NO:24)
```
  1 MQEPRRVTHC LGKRGVKTPQ LQPGSAFLPR VRRQSFTARS DSYTTVRDFL AVPRTISSAS
 61 ATLIMAVAVS HFRPGPEVWD TASMAASKVK QDMPPPGGYG PIDYKRNLPR RGLSGYSMLA
121 IGIGTLIYGH WSIMKWNRER RRLQIEDFEA RIALLPLLQA ETDRRTLQML RENLEEEAII
181 MKDVPDWKVG ESVFHTTRWV PPLIGELYGL RTTEEALHAS HGFMWYT
```

FIG. 10 continued

I) AC6 (ADENYLATE CYCLASE 6, SEQ ID NO:25)

```
   1 MSWFSGLLVP KVDERKTAWG ERNGQKRSRR RGTRAGGFCT PRYMSCLRDA EPPSPTPAGP
  61 PRCPWQDDAF IRRGGPGKGK ELGLRAVALG FEDTEVTTTA GGTAEVAPDA VPRSGRSCWR
 121 RLVQVFQSKQ FRSAKLERLY QRYFFQMNQS SLTLLMAVLV LLTAVLLAFH AAPARPQPAY
 181 VALLACAAAL FVGLMVVCNR HSFRQDSMWV VSYVVLGILA AVQVGGALAA DPRSPSAGLW
 241 CPVFFVYIAY TLLPIRMRAA VLSGLGLSTL HLILAWQLNR GDAFLWKQLG ANVLLFLCTN
 301 VIGICTHYPA EVSQRQAFQE TRGYIQARLH LQHENRQQER LLLSVLPQHV AMEMKEDINT
 361 KKEDMMFHKI YIQKHDNVSI LFADIEGFTS LASQCTAQEL VMTLNELFAR FDKLAAENHC
 421 LRIKILGDCY YCVSGLPEAR ADHAHCCVEM GVDMIEAISL VREVTGVNVN MRVGIHSGRV
 481 HCGVLGLRKW QFDVWSNDVT LANHMEAGGR AGRIHITRAT LQYLNGDYEV EPGRGGERNA
 541 YLKEQHIETF LILGASQKRK EEKAMLAKLQ RTRANSMEGL MPRWVPDRAF SRTKDSKAFR
 601 QMGIDDSSKD NRGTQDALNP EDEVDEFLSR AIDARSIDQL RKDHVRRFLL TFQREDLEKK
 661 YSRKVDPRFG AYVACALLVF CFICFIQLLI FPHSTLMLGI YASIFLLLLI TVLICAVYSC
 721 GSLFPKALQR LSRSIVRSRA HSTAVGIFSV LLVFTSAIAN MFTCNHTPIR SCAARMLNLT
 781 PADITACHLQ QLNYSLGLDA PLCEGTMPTC SFPEYFIGNM LLSLLASSVF LHISSIGKLA
 841 MIFVLGLIYL VLLLLGPPAT IFDNYDLLLG VHGLASSNET FDGLDCPAAG RVALKYMTPV
 901 ILLVFALALY LHAQQVESTA RLDFLWKLQA TGEKEEMEEL QAYNRRLLHN ILPKDVAAHF
 961 LARERRNDEL YYQSCECVAV MFASIANFSE FYVELEANNE GVECLRLLNE IIADFDEIIS
1021 EERFRQLEKI KTIGSTYMAA SGLNASTYDQ VGRSHITALA DYAMRLMEQM KHINEHSFNN
1081 FQMKIGLNMG PVVAGVIGAR KPQYDIWGNT VNVSSRMDST GVPDRIQVTT DLYQVLAAKG
1141 YQLECRGVVK VKGKGEMTTY FLNGGPSS
```

J) AC7 (ADENYLATE CYCLASE 7, SEQ ID NO:27)

```
   1 MPAKGRYFLN EGEEGPDQDA LYEKYQLTSQ HGPLLLTLLL VAATACVALI IIAFSQGDPS
  61 RHQAILGMAF LVLAVFAALS VLMYVECLLR RWLRALALLT WACLVALGYV LVFDAWTKAA
 121 CAWEQVPFFL FIVFVVYTLL PFSMRGAVAV GAVSTASHLL VLGSLMGGFT TPSVRVGLQL
 181 LANAVIFLCG NLTGAFHKHQ MQDASRDLFT YTVKCIQIRR KLRIEKRQQE NLLLSVLPAH
 241 ISMGMKLAII ERLKEHGDRR CMPDNNFHSL YVKRHQNVSI LYADIVGFTQ LASDCSPKEL
 301 VVVLNELFGK FDQIAKANEC MRIKILGDCY YCVSGLPVSL PTHARNCVKM GLDMCQAIKQ
 361 VREATGVDIN MRVGIHSGNV LCGVIGLRKW QYDVWSHDVS LANRMEAAGV PGRVHITEAT
 421 LKHLDKAYEV EDGHGQQRDP YLKEMNIRTY LVIDPRSQQP PPPSQHLPRP KGDAALKMRA
 481 SVRMTRYLES WGAARPFAHL NHRESVSSGE THVPNGRRPK SVPQRHRRTP DRSMSPKGRS
 541 EDDSYDDEML SAIEGLSSTR PCCSKSDDFY TFGSIFLEKG FEREYRLAPI PRARHDFACA
 601 SLIFVCILLV HVLLMPRTAA LGVSFGLVAC VLGLVLGLCF ATKFSRCCPA RGTLCTISER
 661 VETQPLLRLT LAVLTIGSLL TVAIINLPLM PFQVPELPVG NETGLLAASS KTRALCEPLP
 721 YYTCSCVLGF IACSVFLRMS LEPKVVLLTV ALVAYLVLFN LSPCWQWDCC GQGLGNLTKP
 781 NGTTSGTPSC SWKDLKTMTN FYLVLFYITL LTLSRQIDYY CRLDCLWKKK FKKEHEEFET
 841 MENVNRLLLE NVLPAHVAAH FIGDKLNEDW YHQSYDCVCV MFASVPDFKV FYTECDVNKE
 901 GLECLRLLNE IIADFDELLL KPKFSGVEKI KTIGSTYMAA AGLSVASGHE NQELERQHAH
 961 IGVMVEFSIA LMSKLDGINR HSFNSFRLRV GINHGPVIAG VIGARKPQYD IWGNTVNVAS
1021 RMESTGELGK IQVTEETCTI LQGLGYSCEC RGLINVKGKG ELRTYFVCTD TAKFQGLGLN
```

DIAGNOSTIC TESTS OF SUBSTANCE USE DISORDERS

This application is a U.S. national entry of International Application No. PCT/US2006/043098, filed Nov. 3, 2006, which claims benefit of U.S. Provisional Application No. 60/733,386, filed Nov. 3, 2005.

This invention was made in part with government support under grant 1R44AA014531, from the National Institute on Alcohol Abuse and Alcoholism. As such, the United States Government has certain rights in the invention.

SUBMISSION OF SEQUENCE LISTING ON SCH TEXT FILE

The content of the following submission on ASCII text file is incorporated herein by reference in its entirety: a computer readable form (CRF) of the Sequence listing (file name: 643892000100SEQLISTING.txt, date recorded: Jun. 24, 2011, size: 53 KB).

FIELD OF THE INVENTION

The present invention provides platelet-associated markers of substance use disorders. The present invention also provides proteomic methods for the identification of additional biomarkers of substance use, as well as for the identification of biomarkers of other medical disorders. In particular, the present invention provides methods and compositions for the diagnosis of chronic alcohol use and/or for monitoring abstinence.

BACKGROUND OF THE INVENTION

The term substance use disorder encompasses both dependence on and abuse of drugs (e.g., depressants, stimulants, opioids, cannabinols, hallucinogens, inhalants) usually taken voluntarily for the purpose of their effect on the central nervous system (e.g., intoxication or high) or to prevent or reduce withdrawal symptoms (Diagnostic and Statistical Manual of Mental Disorders, 4th edition, American Psychiatric Association, Washington D.C., 1994). These maladaptive patterns of substance use in and of themselves lead to significant impairment and distress. In addition, substance abuse and dependence may worsen preexisting medical conditions and/or mimic other types of medical or psychiatric problems. The lifetime prevalence of substance use disorders including alcoholism is on the order of 20% for men and 15% for women, with young adults and middle-aged persons most heavily affected (See, e.g., Schuckit, "Drug Abuse and Dependence," in *Scientific American Medicine*, vol. 3, chapter 13, section IV, pp. 1-12, 2004). Importantly, substance abuse related conditions are estimated to reduce the life span of a dependent individual by some ten or more years (Schuckit, supra, 2004). In fact, in the United States, over 100,000 deaths/year are directly attributed to alcohol use (O'Connor, "Alcohol Abuse and Dependency," in *Scientific American Medicine*, vol. 3, chapter 13, section III, pp. 1-9, 2001). Substance abuse not only impinges on the health of the drug abusing individual, but also affects other members of society through drug use related accidents, crime, etc.

The identification of individuals who are heavily consuming alcohol or other licit (e.g., tobacco) or illicit drugs, as well as the ability to monitor those individuals who are receiving treatment for dependence, requires objective biochemical markers of alcohol or drug use. Most drug screens use urine samples, however for a result to be positive a subject must have taken the substance in question recently (e.g., hours, or at most, days). Thus, a sample from a subject with a severe, chronic substance use problem, may test negative if the subject is able to refrain from using the substance for only one or two days preceding the toxicology screen. Moreover, typical urine tests simply indicate the presence or absence of a drug or its metabolite, and do not provide any information regarding the quantity or pattern of drug use.

Thus, there remains a need in the art for methods and test kits for assessing drug use, abstinence and/or relapse. In particular, the identification of stable biomarkers that are reflective of chronic, heavy substance use and/or occurrence of relapse are desirable for development of improved diagnostic tools.

SUMMARY OF THE INVENTION

The present invention provides platelet-associated markers of substance use disorders. The present invention also provides proteomic methods for the identification of additional biomarkers of substance use, as well as for the identification of biomarkers of other medical disorders. In particular, the present invention provides methods and compositions for the diagnosis of chronic alcohol use and/or for monitoring abstinence. In some preferred embodiments, the present invention provides one or more state markers of alcohol consumption that are largely unaffected by concomitant conditions or traits (e.g., depression, tobacco use, etc.).

Specifically, the present invention provides methods of determining the relative level of expression of a platelet associated substance use (PASU) marker in a sample from a subject, comprising: measuring PASU marker protein content and control protein content or total protein content of a sample from a subject, wherein the sample comprises platelets from the subject; and determining the relative level of the PASU marker expression in the sample, wherein the relative level correlates with the amount of use of a substance by the subject. In some embodiments, the determining step comprises comparing the PASU marker protein content to the control protein content or the total protein content. In some preferred embodiments, the substance is alcohol. In other embodiments, the substance is selected from the group consisting of amphetamines, cannabis, cocaine, hallucinogens (including but not limited to psychedelics, LSD, mescaline, peyote, psilocybin and DMT), inhalants (including but not limited to glue, gasoline, toluene and solvents), nicotine, opioids (including but not limited to heroin, methadone, morphine, demerol, percodan, opium, codeine, and darvon), phencyclidines, and sedatives (including but not limited to sleeping pills, barbiturates, seconal, valium, librium, ativan, xanax and quaaludes). In some preferred embodiments, the determining step is accomplished by use of an affinity-type method. In a subset of these embodiments, the affinity-type method comprises antibody-based methods or aptamer-based methods. In some particularly preferred embodiments, the PASU marker protein comprises monoamine oxidase-B (MAO-B). In other embodiments, the PASU marker protein is selected from the group consisting of CGI-51, glycine aminotransferase (GATM), oxoglutarate dehydrogenase (OGDH), peripheral benzodiazepine receptor (PBDR), and adenylyl cyclase (AC). Also provided by the present invention are embodiments, which further comprise obtaining the sample from the subject prior to the measuring, identifying the subject as having used a hazardous or harmful amount of the substance in the 3 to 7 days prior to the obtaining, and/or determining the approximate amount of use of the substance by the subject. Still further embodiments additionally comprise identifying the subject as not having used a hazardous or harmful amount of the substance in the 3 to 7 days prior to the obtaining step.

Moreover, the present invention provides methods for monitoring alcohol consumption by a subject, comprising: obtaining a sample comprising platelets from a subject; measuring platelet associated substance use (PASU) marker protein content and control protein content or total protein content of the sample; and comparing the PASU marker protein content to the control protein content or the total protein content to obtain a ratio, wherein the ratio is correlated with recent alcohol consumption by the subject. In some embodiments, the sample comprises blood. In some preferred embodiments, the measuring is accomplished by use of an affinity-type method. In a subset of these embodiments, the affinity-type method comprises antibody-based methods. In other embodiments, the affinity type method comprises aptamer-based methods. In still further embodiments, the measuring is accomplished by use of a proteomics method. In some embodiments, the proteomic methods comprise liquid chromatography and tandem mass spectrometry. In some preferred embodiments, the proteomic methods further comprise multidimensional protein identification technology (MudPIT). In some particularly preferred embodiments, the PASU marker protein comprises a membrane protein. In some embodiments, the PASU marker protein comprises a mitochondrial protein. In exemplary embodiments, the PASU marker protein is monoamine oxidase-B (MAO-B) protein, and/or the control protein comprises platelet p110 protein.

The present invention provides methods for monitoring alcohol consumption by a subject, comprising: obtaining a sample comprising platelets from a subject; measuring platelet associated substance use (PASU) marker protein content and control protein content or total protein content of the sample; and comparing the PASU marker protein content to the control protein content or the total protein content to obtain a ratio, wherein the ratio is correlated with recent alcohol consumption by the subject. In some preferred embodiments, the ratio of MAO-B protein content to the total protein content is significantly higher when the subject has abstained from drinking alcohol for at least 7 days, then when the subject has consistently consumed a hazardous or harmful amount of alcohol. In a subset of these embodiments, the subject is male and the hazardous or amount of alcohol is on average greater than 40 g/day, and the harmful amount of alcohol is on average greater than 80 g/day. In other embodiments, the subject is female and the hazardous amount of alcohol is on average greater than 20 g/day, and the harmful amount of alcohol is on average greater than 60 g/day. In some embodiments, when the ratio of MAO-B protein content to the total protein content is less than a threshold value, the ratio is indicative of recent hazardous or harmful alcohol use by the subject. In further embodiments, when the ratio of MAO-B protein content to the control protein content is greater than a threshold value, the ratio is indicative of abstinence or non-hazardous alcohol use by the subject. In preferred embodiments, abstinence comprises at least 14 days without hazardous or harmful alcohol use. In still further embodiments, when the ratio of MAO-B protein content to the control protein content is less than a threshold value, the ratio is correlated with recent hazardous or harmful alcohol use by the subject. In a subset of these embodiments, the subject is male and the hazardous or amount of alcohol is on average greater than 40 g/day, and the harmful amount of alcohol is on average greater than 80 g/day. In alternative embodiments, the subject is female and the hazardous amount of alcohol is on average greater than 20 g/day, and the harmful amount of alcohol is on average greater than 60 g/day. In some particularly preferred embodiments, the threshold value for a male subject is different from the threshold value for a female subject.

Also provided by the present invention are methods for monitoring alcohol consumption by a subject, comprising: obtaining a sample comprising platelets from a subject; measuring platelet associated substance use (PASU) marker protein content and control protein content or total protein content of the sample; and comparing the PASU marker protein content to the control protein content or the total protein content to obtain a ratio, wherein the ratio is correlated with recent alcohol consumption by the subject. Some embodiments further comprise correlating the ratio with the subject's risk for developing an alcohol-related health problem. In some preferred embodiments, the alcohol-related health problem comprises one or more of the group consisting of a neurological problem, a gastrointestinal problem, liver disease, and a cardiovascular problem. In some embodiments, the neurological problem comprises one or more of dementia, stroke, and peripheral neuropathy; the gastrointestinal problem comprises one or more of esophageal disease, gastritis, and peptic ulcer; the liver disease comprises one or more of alcoholic hepatitis and cirrhosis; and/or the cardiovascular problem comprises one or more of hypertension, left ventricular hypertrophy/cardiomyopathy, arrhythmia and heart attack. In particularly preferred embodiments, the methods further comprise measuring a second marker of alcohol consumption in a sample from the subject, wherein the PASU marker protein comprises a first marker of alcohol consumption. In a subset of these embodiments, the sample is a second sample comprising urine. In some preferred embodiments, the second marker of alcohol consumption comprises one or more of percent carbohydrate-deficient transferrin (% CDT), γ-glutamyltransferase (GGT), alanine/serine aminotransferase (ASAT), and ethyl glucuronide (EtG). Also provided by the present invention are methods wherein the ratio is combined by mathematical means with a value obtained for the second marker of alcohol consumption. In a subset of these embodiments, the mathematical means comprises linear discriminant analysis to increase diagnostic utility of the ratio for assessing hazardous or harmful alcohol use. In some embodiments, the PASU marker protein is selected from the group consisting of CGI-51, glycine aminotransferase (GATM), oxoglutarate dehydrogenase (OGDH), peripheral benzodiazepine receptor (PBDR), and adenylyl cyclase (AC).

Furthermore, the present invention provides methods for identifying a platelet associated substance use (PASU) marker, comprising: providing: i) control platelet membrane samples from control subjects, and ii) experimental platelet membrane samples from subjects diagnosed with a substance use disorder or known to have recently consumed a hazardous or harmful amount of a substance; subjecting the control and experimental platelet membrane samples comprising proteins to proteinase digestion to produce control mixture of peptides and experimental mixture of peptides; subjecting the mixtures to spectrometry to produce a plurality of control spectra and experimental spectra; and identifying at least one protein as a PASU marker, when the at least one protein has a higher or lower peptide spectra count in at least 85% of the experimental samples, as compared to the control samples. In a subset of these embodiments, the at least one protein has a higher or lower peptide spectra count in at least 90%, preferably at least 95%, and more preferably at least 98% of the experimental samples, as compared to the control samples. In some preferred embodiments, the control subjects comprise subjects diagnosed with a substance use disorder, but who have not consumed the substance for at least two weeks prior to collection of the control samples. In some preferred embodiments, the subjects diagnosed with a substance use disorder or known to have recently consumed a hazardous or harmful amount of a substance have consumed the substance within 3 to 7 days of collection of the experimental samples. The proteinase digestion step comprises digestion with proteinase K under high pH conditions, in some embodiments of the present invention. Also provided are embodiments in which the spectrometry step comprises liquid chromatography and tandem mass spectrometry. In some preferred embodiments, the liquid chromatography comprises a reverse phase and a strong cation exchange phase. In some particularly preferred embodiments, the at least one protein is identified from at least three of the peptides from the experimental mixture. Also provided are embodiments in which the methods further comprise assessing the PASU marker protein expression by immunoblotting.

Additionally, the present invention provides kits for detecting a platelet associated substance use (PASU) marker protein, comprising a PASU marker protein binding molecule, and a control protein binding molecule. In some preferred embodiments, the PASU marker protein binding molecule comprises an antibody or antibody fragment. In other preferred embodiments, the PASU marker protein binding molecule comprises an aptamer. In further embodiments, the kits additionally comprise a sample preparation solution suitable for preparing a sample comprising platelets for contact with one or both of the PASU marker and control protein binding molecules. The present invention also provides compositions comprising; a platelet associated substance use (PASU) marker protein binding molecule, and a control protein binding molecule.

DESCRIPTION OF THE FIGURES

FIG. 1 provides a flow chart of the Multidimensional Protein Identification Technology (MudPIT) employed herein for the identification and quantitation of membrane proteins in complex biological samples such as the human platelet.

FIG. 2 depicts the peptide sequence coverage for monoamine oxidase (MAO-B), obtained using, in this particular embodiment, the MudPIT procedure. Below the primary amino acid sequence of MAO-B set forth as SEQ ID NO:1 is a listing of the peptides detected by mass spectrometric analysis, the sequences of which have been set forth as SEQ ID NOS:2-16. The boxed region represents the transmembrane domain of MAO-B (LLRLIGLTT IFSATALGFL A, set forth as SEQ ID NO:17).

FIG. 3, panel A shows an immunoblot of platelet and recombinant MAO-B protein. Samples of platelet membrane proteins (2-20 µg) or recombinant MAO-B protein (10 or 20 ng) were separated by SDS-PAGE as previously described (Snell et al., *Mol Brain Res*, 40:71-78, 1996). Proteins were transferred to nitrocellulose membranes and MAO-B was identified using an affinity-purified polyclonal antibody (1:1000) followed by chemiluminescence detection. Panel B shows a representative immunoblot of MAO-B and p110 proteins.

FIG. 9 provides an alphabetically sorted list of platelet membrane proteins.

FIGS. 9A-N, also referred to herein as Table 1, GENBANK Accession Nos., spectra counts, percent sequence coverage, and descriptive names of platelet membrane proteins.

FIG. 10 provides the amino acid sequence of markers for hazardous/harmful alcohol use (HHAU) identified through the platelet proteomic analysis of the present invention.

FIG. 10A shows MAO-B GENBANK Accession No. NP_000889, version GI:38202207 (SEQ ID NO:1).

FIG. 10B shows CGI-51 GENBANK Accession No. NP_056195, version GI:31542301 (SEQ ID NO:18).

FIG. 10C shows GATM GENBANK Accession No. NP_001473, version GI:4503933 (SEQ ID NO:19).

FIG. 10D shows OGDH GENBANK Accession No. NP_002532, version GI:51873036 (SEQ ID NO:20).

FIG. 10E shows BZRP GENBANK Accession No. NP_000705, version GI:74275350 (SEQ ID NO:21).

FIG. 10F shows GSN GENBANK Accession No. NP_000168, version GI:4504165 (SEQ ID NO:22).

FIG. 10G shows NDUFA8 GENBANK Accession No. NP_055037, version GI:7657369 (SEQ ID NO:23).

FIG. 10H shows GRIM19 GENBANK Accession No. NP_057049, version GI:21361822 (SEQ ID NO:24). Also shown is the amino acid sequence of adenylyl cyclase which is contemplated by the inventors to be a further marker for hazardous/harmful alcohol use (HHAU).

FIG. 10I shows (AC6; GENBANK Accession No. NP_056085.1, version GI:10181096 (SEQ ID NO:25).

FIG. 10J shows (AC7; GENBANK Accession No. NP_001105.1, version GI:4557255 (SEQ ID NO:27).

DEFINITIONS

Figure 4:
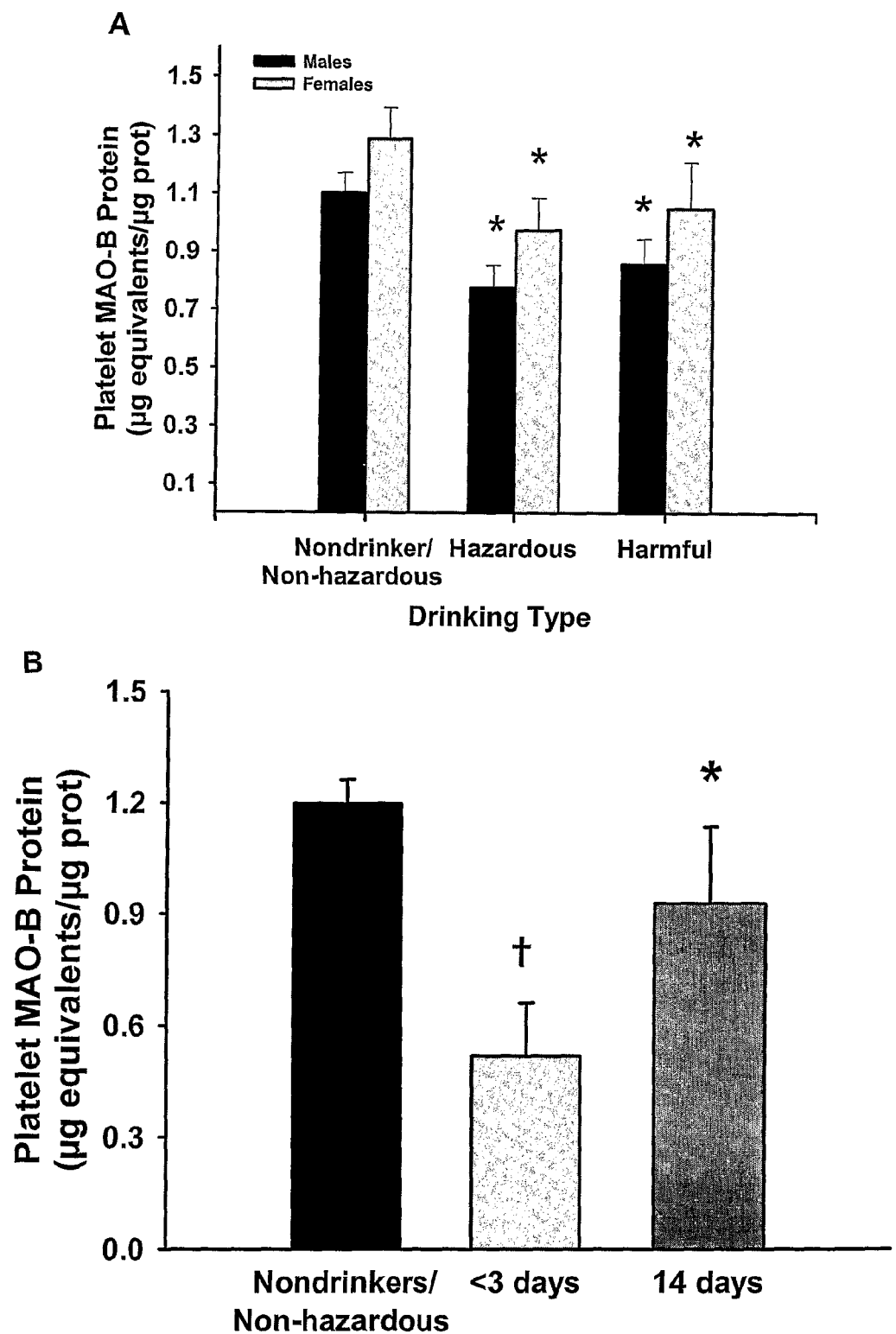
FIG. 4, panel A graphically depicts the reduction in MAO-B protein levels in subjects drinking alcohol at harmful and hazardous levels as compared to MAO-B protein levels observed in abstinent or non-hazardous drinking subjects. An asterisk indicates P<0.01 versus nondrinkers/nonhazardous drinkers by ANOVA with post-hoc Tukey tests. Panel B shows that abstention from alcohol consumption for 14 days was associated with a return of MAO-B protein to levels observed in abstinent/non-hazardous drinking subjects. A cross indicates P<0.01 versus nondrinkers/nonhazardous drinkers by Student's t test, while an asterisk indicates P<0.001 versus same subjects consuming alcohol at harmful levels within three days prior to blood sampling (<3 days; paired t-test).

To facilitate understanding of the invention, a number of terms are defined.

The terms "subject" as used herein, refers to a human. It is intended that the term encompasses healthy individuals, as well as, individuals predisposed to, suspected of having, or diagnosed with a substance use disorder. Typically, the terms "subject" and "patient" are used interchangeably. In some preferred embodiments of the present invention, the term subject refers to specific subgroups of patients such as males that consume hazardous or harmful amounts of alcohol.

As used herein, the term "sample" is meant to include a specimen obtained from a subject. The term "sample" encompasses fluids, solids, and tissues. In preferred embodiments, the term "sample" refers to blood or biopsy material obtained from a living body for the purpose of examination via any appropriate technique (e.g., needle, sponge, scalpel, swab, etc.). In particularly preferred embodiments, the term "sample" refers to a blood sample comprising platelets.

As used herein, the terms "platelets" and "thrombocytes" refer to non-nucleated blood cell fragments that are involved in the formation of blood clots. Low levels or dysfunction predisposes an individual to excess bleeding, while high levels may increase the risk of thrombosis. Platelets are formed in the bone marrow, from cells termed megakaryocytes.

The term "gene" refers to a nucleic acid (e.g., DNA) sequence that comprises coding sequences necessary for the production of a polypeptide (e.g., MAO-B), precursor, or RNA (e.g., mRNA). The polypeptide can be encoded by a full length coding sequence or by any portion of the coding sequence so long as the desired activity or functional properties (e.g., enzymatic activity, ligand binding, signal transduction, immunogenicity, etc.) of the full-length or fragment are retained. The term also encompasses the coding region of a structural gene and the sequences located adjacent to the coding region on both the 5' and 3' ends for a distance of about 1 kb or more on either end such that the gene corresponds to the length of the full-length mRNA. Sequences located 5' of the coding region and present on the mRNA are referred to as 5' non-translated sequences. Sequences located 3' or downstream of the coding region and present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene that are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

As used herein, the term "nucleic acid" refers to any nucleic acid containing molecule, including but not limited to, DNA, cDNA and RNA. In particular, the terms "monoamine oxidase B gene," refer to the full-length MAO nucleotide sequence. The term "MAO-B nucleic acid" as used herein, encompasses the full length MAO nucleotide sequence and fragments of the MAO-B sequence, as well as domains within the full-length MAO-B nucleotide sequence.

The term "wild-type" refers to a gene or gene product isolated from a naturally occurring source. A wild-type gene is that which is most frequently observed in a population and is thus arbitrarily designed the "normal" or "wild-type" form of the gene. In contrast, the term "modified" or "mutant" refers to a gene or gene product that displays modifications in sequence and or functional properties (i.e., altered characteristics) when compared to the wild-type gene or gene product. It is noted that naturally occurring mutants can be isolated; these are identified by the fact that they have altered characteristics (including altered nucleic acid sequences) when compared to the wild-type gene or gene product. In certain embodiments, the MAO-B nucleic acid is wild-type, while in other embodiments it is a mutant sequence.

As used herein, the terms "nucleic acid molecule encoding," "DNA sequence encoding," and "DNA encoding" refer to the order or sequence of deoxyribonucleotides along a strand of deoxyribonucleic acid. The order of these deoxyribonucleotides determines the order of amino acids along the polypeptide (protein) chain. The DNA sequence thus codes for the amino acid sequence.

As used herein, the terms "protein" or "polypeptide" refer to a molecule made up of three or more amino acids [$H_2N$—CHR—COOH] in peptide (amide) linkage (elimination of $H_2O$ between the $NH_2$ and COOH of successive residues), whose order is determined by the nucleic acid sequence of a DNA molecule.

As used herein, the term "peptide" refers to a molecule consisting of two or more amino acids. Peptides are smaller than proteins, which are also chains of amino acids. Molecules small enough to be synthesized from the constituent amino acids are, by convention, called peptides rather than proteins (e.g., about 50 amino acids).

The terms "MAO-B protein" and "monoamine oxidase B polypeptide" include the full-length MAO-B amino acid sequence (set forth as SEQ ID NO:1), as well as fragments of the MAO-B sequence. The MAO-B peptides that are shown in FIG. 2, and set forth as SEQ ID NOS:2-17 are subsets of the amino acid sequence of the full length MAO-B protein, and can be used in the methods of the present invention to identify the presence of the MAO-B protein in a sample.

The term "p110 protein" as used herein, refers to an acidic mitochondrial protein with an apparent molecular weight of 110 kDa, which is recognized by a mouse monoclonal antibody referred to as 2G2 (Paulin-Levasseur et al., *Histochem J*, 30:616-625, 1998).

As used herein, the terms "membrane protein" and "integral membrane protein" refer to a protein that is attached to, or associated with the membrane of a cell or organelle. The term "membrane protein" encompasses proteins that span the membrane (transmembrane proteins) as well as proteins anchored to the membrane's hydrophobic region, by a covalently attached lipid or glycolipid.

The term "mitochondrial protein" as used herein, refers to a protein that is associated with the mitochondria. This term encompasses proteins encoded by mitochondrial DNA, as well as proteins encoded by nuclear DNA.

The terms "percent carbohydrate deficient transferrin" and "% CDT" refer to asialo, monosialo and disialo isoforms of transferrin, whose levels are elevated in the blood of heavy drinkers. % CDT in a sample (e.g., blood, plasma, serum) can be determined by turbidimetric immunoassay (Bio-Rad), or by isoelectric focusing or pH-based anion exchange chromatography (e.g., U.S. Pat. No. 4,626,355, herein incorporated by reference in its entirety).

The terms "γ-glutamyltransferase" and "GGT" refer to an enzymatic biomarker of hepatobiliary disease, including alcoholic liver disease. GGT activity in a sample (e.g., blood, plasma, serum) can be determined by clinical chemistry methods known in the art. In some embodiments, GGT activity is detected by monitoring the GGT catalyzed transfer of γ-glutamyl from L-γ-glutamyl-p-nitroanilide to glycylglycine, producing L-γ-glutamyl-p-glycylglycine and p-nitroanilide, using VITROS chemistry products (See, Ortho-Clinical Diagnostics, Publication No. MP2-43_EN, version 3.0, herein incorporated by reference).

The terms "alanine/serine aminotransferase," "ASAT," "aspartate aminotransferase" and "AST" refer to an enzymatic biomarker of liver disease including alcoholic cirrhosis. ASAT activity in a sample (e.g., blood, plasma, serum) can be determined by clinical chemistry methods known in the art. In some embodiments, ASAT activity is detected by monitoring the ASAT catalyzed transfer of the amino group of L-aspartate to α-ketoglutarate in the presence of pyridoxal-5-phosphate to produce glutamate and oxaloacetate, using VITROS chemistry products (See, Ortho-Clinical Diagnostics, Publication No. MP2-113_EN, version 4.0, herein incorporated by reference).

The terms "ethyl glucuronide" and "EtG" refer to a carbohydrate biomarker of chronic alcoholism. The presence or elevation of EtG in a sample (e.g., urine) from a subject can be determined by chromatographic methods (e.g., thin layer chromatography, HPLC, etc.) known in the art (e.g., U.S. Pat. No. 5,958,785, herein incorporated by reference in its entirety).

The terms "P2X1," "purinoceptor P2X1," "purinergic receptor P2X," and "P2X receptor subunit 1" as used herein refer to an ATP-gated cation channel. P2X1 has an apparent molecular weight of 55 kDa, and is highly expressed on blood platelets membranes, but not significantly expressed in other blood cell types. Exemplary mRNA and protein sequences are shown as GENBANK Accession Nos. NM_002558 and NP_002549.1, respectively.

The terms "β-actin" and "ACTB" as used herein refer to a cell structural protein with an apparent molecular weight of 42 kDa. ACTB is found in all blood cell types. Exemplary mRNA and protein sequences are shown as GENBANK Accession Nos. NM_001101 and NP_001092.1, respectively.

The terms "voltage-dependent anion channel 1," and "VDAC1" refer to the isoform 1 of the voltage-dependent anion channel of mitochondrial membranes. VDAC1 has an apparent molecular weight of 31 kDa. Exemplary mRNA and protein sequences are shown as GENBANK Accession Nos. NM_003374 and NP_003365.1, respectively.

As used herein, the term "control" refers to subjects or samples that provide a basis for comparison for experimental subjects or samples. For instance, the use of control subjects or samples permits determinations to be made regarding the existence of biological markers of substance use disorders. In some embodiments, the term "control subject" refers to subjects that do not consume alcohol at hazardous or harmful levels.

In contrast, the term "experimental" as used herein refers to subjects or samples that are exposed to the variable of an experiment. For instance, in some embodiments, experimental subjects are individuals that drink alcohol at hazardous or harmful levels, or are suspected of having or are diagnosed with a substance use disorder. In other embodiments, experimental subjects are individuals that are suspected of having or are diagnosed with a health problem such as cardiovascular disease, which may or may not stem from substance abuse.

As used herein, the term "total protein content" refers to the mass of all proteins that are present in a sample. For instance, the total protein concentration of a sample can be determined by any one of a number of standard assays known in the art, such as the Bradford assay (Bradford, *Anal Biochem*, 72:248-254, 1976), the Lowry assay (Lowry et al., *J Biol Chem*, 193:265-275, 1951), and the BCA Assay (Smith et al., *Anal Biochem*, 150:76-85, 1985). The total protein content is determined by multiplying the volume of a sample by the total protein concentration of the sample (generally expressed as μg/μl).

Where amino acid sequence is recited herein to refer to an amino acid sequence of a naturally occurring protein molecule, amino acid sequence and like terms, such as polypeptide or protein are not meant to limit the amino acid sequence to the complete, native amino acid sequence associated with the recited protein molecule. Fragments, which are contemplated, typically are at least 4 amino acids long, preferably at least 8 amino acids long, usually at least 16 amino acids long or longer.

As applied to polypeptides, the term "substantial identity" means that two peptide sequences, when optimally aligned, such as by the programs GAP or BESTFIT using default gap weights, share at least 80 percent sequence identity, preferably at least 90 percent sequence identity, more preferably at least 95 percent sequence identity or more (e.g., 99 percent sequence identity). Preferably, residue positions that are not identical, differ by conservative amino acid substitutions. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, and asparagine-glutamine.

The term "biological marker" as used herein, refers to a protein that is correlated with a particular condition. In some preferred embodiments, the biomarker refers to a protein that is correlated with a recent hazardous or harmful alcohol use. In some of these embodiments, the biomarker comprises either a greater or lesser level of protein encoded by a gene of interest.

The term "Southern blot," refers to the analysis of DNA on agarose or acrylamide gels to fractionate the DNA according to size followed by transfer of the DNA from the gel to a solid support, such as nitrocellulose or a nylon membrane. The immobilized DNA is then probed with a labeled probe to detect DNA species complementary to the probe used. The DNA may be cleaved with restriction enzymes prior to electrophoresis. Following electrophoresis, the DNA may be partially depurinated and denatured prior to or during transfer to the solid support. Southern blots are a standard tool of molecular biologists (Sambrook et al., *Molecular Cloning: A Laboratory Manual*, Cold Spring Harbor Press, NY, pp 9.31-9.58, 1989).

The term "Northern blot," as used herein refers to the analysis of RNA by electrophoresis of RNA on agarose gels to fractionate the RNA according to size followed by transfer of the RNA from the gel to a solid support, such as nitrocellulose or a nylon membrane. The immobilized RNA is then probed with a labeled probe to detect RNA species complementary to the probe used. Northern blots are a standard tool of molecular biologists (Sambrook, et al., supra, pp 7.39-7.52, 1989).

The term "Western blot" refers to the analysis of protein(s) (or polypeptides) immobilized onto a support such as nitrocellulose or a membrane. The proteins are run on acrylamide gels to separate the proteins, followed by transfer of the protein from the gel to a solid support, such as nitrocellulose or a nylon membrane. The immobilized proteins are then exposed to antibodies with reactivity against an antigen of interest. The binding of the antibodies may be detected by various methods, including the use of radiolabeled antibodies.

As used herein, the terms "antibody-based method" or "immunoassay" refer to any method comprising the use of an antibody to detect the presence of an antigen in a sample.

The terms "proteomic method" or "proteomics" as used herein, refer to any suitable method for analyzing the proteome (collection of proteins) of a cell, organelle, subcellular fraction or sample thereof. In preferred embodiments, the "proteomic method" comprises a means for separating proteins/peptides, a means for identifying proteins/peptides, and a means for quantitating proteins/peptides. In some preferred embodiments, the means for separating proteins/peptides comprises liquid chromatography, the means for identifying proteins/peptides comprises mass spectrometry, and the means for quantitating proteins/peptides comprises spectral sampling.

As used herein, the term "shotgun proteomics" refers to a method for directly analyzing complex peptide mixtures generated from the proteolysis of samples containing many proteins, to rapidly generate a global profile of the protein complement within the mixture (Wu and MacCoss, *Curr Opin Mol Ther*, 4:242-245, 2002). In some preferred embodiments, the shotgun proteomics methods comprise a combination of liquid chromatography (LC)-tandem mass spectrometry (MS/MS) and sequence database searching (Patterson and Aebersold, *Nat Gen Suppl* 33:311-323, 2003). Some of the complexity of this approach can be reduced by introducing upstream fractionation of complex peptide mixtures (Wu and Yates, *Nat Biotech*, 21:262-267, 2003; and Rabilloud, *Nat Biotechnology*, 21:508-510, 2003).

As used herein, the terms "liquid chromatography," "LC," "high performance liquid chromatography," and "HPLC" refer to a form of chromatography in which an analyte is forced through a stationary phase column in a liquid (mobile phase) at high pressure. This decreases the time the separated components remain on the stationary phase and thus the time they have to diffuse within the column, leading to narrower peaks in the resulting chromatogram and to better resolution and sensitivity.

The terms "mass spectrometry" and "MS" refer to a technique for separating ions by their mass to charge (m/z) ratios. This is normally achieved by ionizing a sample and separating ions of differing masses and recording their relative abundance by measuring intensities of ion flux. A typical mass spectrometer comprises an ion source, a mass analyzer, and a detector.

As used herein, the terms "tandem mass spectrometry" and "MS/MS" refer to methods for obtaining sequence information from individual peptides by isolating them, colliding them with a nonreactive gas, and then cataloging the fragment ions produced.

The term "spectral sampling" as used herein, refers to the number of spectra acquired for each protein in a complex protein sample during analysis using shotgun proteomics methods. Liu and colleagues have shown that a relationship exists between the level of sampling observed for a protein and the relative abundance of the protein in the mixture (Liu et al., *Anal Chem*, 76:4193-201, 2004).

The term "spectrum" as used herein refers to a distribution of ions as shown by a mass spectrograph or a mass spectrometer. The term "spectra" is the plural form of the term spectrum.

As used herein, the terms "MudPIT" and "multidimensional protein identification technology" refer to a technique for the separation and identification of complex protein and peptide mixtures, which employs two-dimensional liquid chromatography, as opposed to traditional two-dimensional gel electrophoresis (e.g., Washburn et al., *Nat Biotechnol*, 19:242-247, 2001; and Wu and Yates, *Nat Biotech*, 21:262-, 2003, herein incorporated by reference in their entirety). One advantage of this technology is that it can be interfaced directly with the ion source of a mass spectrometer.

The term "high pH" refers to a basic pH suitable for homogenization of a sample comprising membranes. In some embodiments, a high pH is obtained by addition of urea to a sample.

The terms "protease," "proteinase," "peptidase" and "proteolytic enzyme" refer to an enzyme that catalyzes the splitting of proteins into smaller peptide fractions and amino acids by a process known as proteolysis. In preferred embodiments, the term protease refers to a nonspecific protease such as proteinase K. "Proteinase K" is a serine protease derived from *Tritirachium album* that cleaves peptide bonds at the carboxylic sides of aliphatic, aromatic or hydrophobic amino acids.

As used herein the terms "addictive disorder," "substance-related disorder" and "substance use disorder" refer to a disease characterized by the habitual psychological and physiologic dependence on a substance or practice that is beyond voluntary control. The term "addictive disorder" includes but is not limited to: alcohol dependence (e.g., alcoholism); amphetamine dependence (e.g., stimulants, speed, uppers, diet pills); cannabis dependence (e.g., marijuana, grass, pot, weed, reefer, hashish, bhang, ganja); cocaine dependence (e.g., coke, crack, coca leaves); hallucinogen dependence (e.g., psychedelics, LSD, mescaline, peyote, psilocybin, DMT); inhalant dependence (e.g., sniffing: glue, gasoline, toluene, solvents); nicotine dependence (e.g., tobacco); opioid dependence (e.g., heroin, methadone, morphine, demerol, percodan, opium, codeine, darvon); phencyclidine dependence (e.g., PCP, angel dust); and sedative dependence (e.g., sleeping pills, barbiturates, seconal, valium, librium, ativan, xanax, quaaludes).

The term "alcohol abuse" as used herein refers to a clinical syndrome (See, DSM-IV) that includes one or more of the following over 1 year: alcohol use despite social or interpersonal problems; alcohol use in physically hazardous situations; alcohol use resulting in failure to fulfill obligations; recurrent alcohol-related fights; and alcohol-related legal problems.

The term "alcohol dependence" as used herein refers to a clinical syndrome (See, DSM-IV) that includes at least three of the following over 1 year: tolerance (e.g., increased drinking to achieve same effect); alcohol withdrawal signs; drinking more alcohol than intended; unsuccessful attempts to cut down on use; excessive time related to alcohol (e.g., obtaining, hangover); impaired social or work activities due to alcohol; and use despite physical or psychological consequences. While alcohol tolerance is a phenomenon that is evident in both alcohol abusing and alcohol dependent individuals, the phenomenon of alcohol abuse is differentiated from alcohol dependence by the DSM-UV criteria for these phenomena (e.g., alcohol abusing individuals are ones that meet the criteria for abuse, but do not meet the criteria for dependence).

As used herein, the term "risk of developing alcohol abuse or dependence" refers to a subject's relative risk (e.g., the percent chance or a relative score) of developing alcohol abuse or dependence during their lifetime.

The term "subject suspected of being alcohol dependent" refers to a subject that presents one or more symptoms indicative of alcohol dependence (e.g., physiologic tolerance, withdrawal symptoms, excessive use, etc.) or is being screened for alcohol dependence (e.g., during a routine physical).

As used herein, the term "alcohol-related" refers to phenomena associated with alcohol consumption. For example, the phrase "alcohol-related legal problems," refer to legal problems (e.g., drunk driving/driving under influence/driving while intoxicated: the crime of operating a motor vehicle while under the influence of alcohol) associated with alcohol intake.

As used herein, the term "instructions for determining whether a subject has recently engaged in hazardous or harmful alcohol use" refers to instructions for using the reagents of the kit for determining the PASU marker protein content in a platelet sample relative to the total protein content or a control protein content of the sample from a subject. In some preferred embodiments, the PASU marker protein is selected from but not limited to CGI-51, GATM, OGDH, PBDR and AC, while in particularly preferred embodiments, the term PASU marker protein refers to MAO-B. In some embodiments, the instructions further comprise the statement of intended use required by the U.S. Food and Drug Administration (FDA) in labeling in vitro diagnostic products. The FDA classifies in vitro diagnostics as medical devices and requires that they be approved through the 510(k) procedure. Information required in an application under 510(k) includes the following: 1) The in vitro diagnostic product name, including the trade or proprietary name, the common or usual name, and the classification name of the device; 2) The intended use of the product; 3) The establishment registration number, if applicable, of the owner or operator submitting the 510(k) submission; the class in which the in vitro diagnostic product was placed under section 513 of the FD&C Act, if known, its appropriate panel, or, if the owner or operator determines that the device has not been classified under such section, a statement of that determination and the basis for the determination that the in vitro diagnostic product is not so classified; 4) Proposed labels, labeling and advertisements sufficient to describe the in vitro diagnostic product, its intended use, and directions for use, including photographs or engineering drawings, where applicable; 5) A statement indicating that the device is similar to and/or different from other in vitro diagnostic products of comparable type in commercial distribution in the U.S., accompanied by data to support the statement; 6) A 510(k) summary of the safety and effectiveness data upon which the substantial equivalence determination is based; or a statement that the 510(k) safety and effectiveness information supporting the FDA finding of substantial equivalence will be made available to any person within 30 days of a written request; 7) A statement that the submitter believes, to the best of their knowledge, that all data and information submitted in the premarket notification are truthful and accurate and that no material fact has been omitted; and 8) Any additional information regarding the in vitro diagnostic product requested that is necessary for the FDA to make a substantial equivalency determination. Additional information is available at the Internet web page of the U.S. FDA.

GENERAL DESCRIPTION OF THE INVENTION

The abuse of and addiction to alcohol, tobacco and illicit drugs constitute economic and social problems for society as a whole. In order to initiate treatment to reduce alcohol and drug consumption, it is necessary to identify those individuals who are abusing these substances. Once treatment has been established, it is necessary to monitor the success of the treatment and possible episodes of relapse. Currently available biochemical markers of heavy alcohol consumption are hampered by the high incidence of false negatives (low sensitivity) and false positives (low specificity) for measurement of recent heavy alcohol consumption. Cardiovascular disease is the leading cause of death and liver disease is currently the ninth leading cause of death in the United States. Much of the damage to these organs is caused by excessive consumption of ethanol. Identifying individuals who drink excessive levels of ethanol would greatly aid the physician in preventing and treating cardiovascular and liver disease.

As described herein, the present invention, in certain embodiments, employs an improved method of "shotgun" proteomic analysis for the measurement of platelet membrane proteins in control, alcohol or drug-consuming individuals or individuals suspected of having liver disease. This technique comprises limited protein hydrolysis, chromatographic separation of proteins and identification of proteins by mass spectrometry and sequence database searching. This approach allows for an unbiased determination of proteins that differ in individuals recently (past 3-14 days) consuming alcohol or other drugs. This methodology has made possible the identification of 514 platelet membrane proteins with 2-peptide coverage (>90% confidence level), and 218 proteins with 3-peptide coverage (>95% confidence level) as shown in Table 1. The present invention provides a method for quantitatively assessing by spectral sampling the platelet membrane proteins in control and alcohol/drug-using subjects, or persons with medical pathologies such as liver or cardiovascular disease. It has been shown that the number of spectra obtained for each protein (spectral sampling) can be directly related to the relative abundance of the protein in a mixture (Liu et al, *Anal Chem*, 76:4193-4201, 2004).

An experimental example is provided to demonstrate and clearly illustrate certain aspects of the invention. In this exemplary embodiment, a platelet membrane protein identified through mass spectroscopic analysis as monoamine oxidase B (MAO-B) was quantitated, and found to differ in a group of hazardous/harmful alcohol drinkers as compared to individuals drinking alcohol at non-harmful levels. The platelet protein, p110 (Paulin-Levasseur, *Histochem J*, 30:617-625, 1998), was found by antibody techniques not to differ between individuals regardless of their level of alcohol consumption, and as such is employed as an "internal standard" in the exemplary diagnostic procedure described herein. For high-throughput analysis, an antibody was generated to the MAO-B protein and MAO-B protein levels were measured in platelet membranes of 237 individuals known to consume alcohol at different levels. ROC analysis demonstrated that measurements of platelet MAO protein produced good sensitivity and specificity for discriminating hazardous/harmful drinking from non-hazardous drinking, and that specificity and/or sensitivity were improved when measures of MAO protein levels were combined with other markers of alcohol consumption (e.g., % CDT, lnGGT, lnASAT). Logistic regression analysis showed that the level of MAO protein is not influenced by a number of environmental and health variables that frequently compromise the validity of currently available biochemical markers of alcohol intake (e.g., CDT, GGT, etc). The reversibility of the suppression of MAO protein levels in platelets of male heavy drinkers after a 14-day period of abstinence was also observed. This reversibility phenomenon qualifies MAO protein levels as a "state" marker of heavy alcohol consumption, rather than being a reflection of a genetically determined trait marker (Demir et al., *Alcohol Alcohol*, 37:597-602, 2002; von Knorring et al., *Alcohol Alcohol*, 26:409-419, 1991), as demonstrated herein for the first time. Additionally the inventors have found that the ratio of MAO protein levels to p110 protein levels correlates well with the average quantity of alcohol consumed per day by an individual, and that MAO protein levels can act as sensitive marker of relapse to hazardous alcohol drinking.

DESCRIPTION OF THE INVENTION

I. Introduction to Platelet Proteomics

The proteome is the set of proteins encoded by the genome, and proteomics is the study of proteomes. One aspect of proteomics termed profiling proteomics is concerned with the description of the whole proteome of an organism. Profiling proteomics includes mapping of the proteome of organelles and cells, and measurement of differential protein expression in different types of cells or in the same type of cell exposed to different conditions (Tyers and Mann, *Nature*, 422:193-197, 2003; Choudhary and Grant, *Nat Neurosci*, 7:440-445, 2004; Patterson and Aebersold, *Nat Gen Suppl*, 33:311-323, 2003). Proteomics complements other functional genomics approaches, such as microarray analysis of gene expression, as a means to provide a full description of cellular function. The use of bioinformatics techniques to integrate the data obtained from these different sources provides investigators with a powerful and comprehensive database describing gene function (Tyers and Mann, *Nature*, 422:193-107, 2003).

Proteomic analysis is likely to have an important impact on clinical diagnosis and drug discovery (Tyers and Mann, supra, 2003). Profiling proteomics, for example, allows for the determination of protein profiles associated with particular disease states, in a similar manner to the use of gene expression profiling for cancer diagnosis (e.g., Carr et al, *Hum Genomics*, 1:134-140, 2004). Because most drug targets are proteins, proteomics is also likely to play a key role in drug discovery. The idea that proteomic research can identify biomarkers of disease states has received considerable attention (Hanash, *Nature* 422:226-232, 2003). The technologies used for proteomic research, including mass spectrometry for protein identification, allow for the determination of protein profiles in biological fluids or tissues without the need to first separate the proteins. The determination of differences in the level of proteins between tissue from normal and diseased individuals is contemplated to aid in the identification of new markers of disease. However, before this goal can be realized, development of tools suitable for accurate quantitation of protein levels in different samples is required.

In order to use proteomic analysis for diagnostic purposes, it is first useful to identify an easily accessible human tissue or cell type that is homogeneous and that is exposed to the internal milieu (e.g., by circulation through the organs of the body). Other characteristics that are useful for the diagnostic application of proteomics include responsiveness of the chosen cell and/or its proteins to relatively rapid changes in the body (e.g., changes in blood pressure, use of medications). Additionally, it is also useful that the chosen cell and/or its proteins have an appropriate rate of protein (or cellular) turnover, such that the cells/proteins reflect the condition of the body over the past several days.

The platelet represents a cell type with many of these desired characteristics. Platelets are small, enucleated cells involved in hemostasis and blood clotting at sites of vascular injury. They are derived from cytoplasmic fragmentation of megakaryocyte precursors, which are in turn derived from hematopoietic stem cells, present in bone marrow. The megakaryocyte precursors initially proliferate before differentiation into mature cells, from which the platelets are released. All of these processes are controlled by a complex signaling pathway that involves many growth factors and transcription factors (Matsumura and Kanakura, *Int J Hematology and Oncology*, 75:473-483, 2002; van geet, *Verh K Acad Geneeskd Bldg*, 66:5-24, 2004; and Italiano and Shivdasani, *J Thromb and Haemostasis*, 1:1174, 2003). Under normal conditions, platelets have a half-life of 4-5 days. With appropriate stimulation, platelets are activated, which involves protein phosphorylation and reorganization of the platelet membrane and cytoskeleton proteins, producing the rapid shape changes necessary for platelet aggregation and formation of a hemostatic plug. The relatively rapid turnover of platelets, and their ability to rapidly change morphologically and biochemically in response to changes in the body, make them useful as markers of the recent physiological state of the body. In addition, platelets contain proteins that are also expressed in the brain, and these proteins have been suggested to reflect the state of the proteins in the brain, which are more difficult, if not impossible, to assess in live humans (See, e.g., Williams et al., *Neuropharmacology*, 47:148-166, 2004). For example, platelet monoamine oxidase enzyme activity and platelet adenylyl cyclase enzyme activity have been measured to obtain insights into brain chemistry of schizophrenic and depressed individuals (Spivak et al., *Clin Neuropharmacol*, 17:83-88, 1994; Wahlund et al., *J Affect Disord*, 35:75-87, 1995; Mooney et al., *Biol Psychiatry*, 43:574-583, 1998; and Menninger and Tabakoff, *Biol Psychiatry*, 42:30-38, 1997), and alcoholics (Whitfield et al., *Psychol Med* 30:443-454, 2000; Oreland, *Neurotoxicology*, 25:79-89, 2004; Demir et al., *Alcohol Alcohol*, 2002:597-602, 2002; Anthenelli et al., *Biol Psychiatry*, 38:361-368, 1995; Devor et al., *Am J Med Genet*, 48:209-213, 1993; Hoffman et al., *Alcohol Clin Exp Res*, 26:1078-1087, 2002; Menninger et al., *Alcohol Clin Exp Res*, 22:1955-1961, 1998; and Tabakoff et al., *N Engl J Med*, 318:134-139, 1988). Activity of the serotonin transporter enzyme has also been assessed using platelets of alcoholic subjects (Javors et al., *Prog Neuropsychopharmacol Biol Psychiatry*, 29:7-13, 2005) to determine whether these transporters reflect correlates of brain function. A small number of platelet proteins, including the platelet serotonin transporter and platelet interleukin 6, have also been measured by immunoblotting (Marta et al., *Cytokine*, 29:13-17, 2005; Dmitriev et al., *Biochemistry (Mosc)* 69:629-641, 2004). However, adenylyl cyclase, MAO and p110 protein levels in platelets have never been measured in relation to substance use disorders.

There has been interest in mapping the platelet proteome, since the platelet is an enucleated cell that plays an important role in thrombosis and heart disease, even though it does contain some mRNA and may be capable of limited protein transcription and translation (Weyrich et al., *Sem Thromb Hemost*, 30:491-498, 2004; and McRedmond et al., *Mol Cell Proteomics*, 3:133-144, 2004). Two studies used 2-dimensional (2D) gel electrophoresis, with narrow pH gradients during the isoelectric focusing phase to separate platelet proteins, and, following in-gel proteolysis of selected protein spots, analyzed the resulting peptides by LC-MS/MS (O'Neill et al., *Proteomics* 2:288-305, 2002; Garcia et al., *Mass Spectr Rev* Early View Published Online, 2004). These two studies identified 123 and 311 proteins, respectively, in different pI ranges. However, one of the major limitations with using the 2D gel electrophoresis method for separation of proteins is that membrane proteins are under-represented, because they do not enter the gel (Garcia et al., supra, 2004). Although it is estimated that about 30% of proteins are membrane-bound, only about 1% of these are resolved by 2D gel electrophoresis (Santoni et al., *Electrophoresis* 21:1054-1070, 2000). In the platelet studies, only 3% of the reported proteins (9 proteins) were membrane proteins (Garcia et al., supra, 2004). Another attempt to analyse the platelet proteome employed a gel-free proteomic technique to evaluate platelet proteins, in which diagonal electrophoresis and diagonal chromatography were used to isolate N-terminal peptides (Gevaert et al., *Nat Biotech* 21:566-569, 2003). This procedure reduced the complexity of the peptide sample, since each protein has only one N-terminus represented by a single peptide. These investigators identified 264 proteins from a cytosolic and membrane skeleton fraction of platelets. Although they identified several different membrane proteins from those described by others, only 13 membrane proteins were found. More recently, the problem of identifying membrane proteins in platelets was approached by use of a subcellular prefractionation technique, in which glycolipid-enriched membrane domains (GEMS) were isolated prior to separation by gel electrophoresis and identification by mass spectrometry (Garcia et al., *Sem Thromb and Hemostasis* 30:485-489, 2004). Although improved, this technique resulted in the identification of only 24 proteins, while several proteins known to be associated with GEMS were not found. Other proteomic studies of platelets have identified at least 300 proteins that are not membrane-associated, when focused on proteins released when platelets are activated (Maguire et al., *Trends Cardiovasc Med* 14:207-220, 2004; and Coppinger et al., *Blood* 15:2096-2104, 2004). This inability to identify membrane-associated platelet proteins by proteomic techniques is an important issue for diagnostics, since many of the most informative proteins (e.g., receptors, enzymes, transporters) are located in the plasma membranes or membranes of organelles such as the mitochondrion.

Another key issue for the use of proteomics for diagnostic purposes is that of quantitation. To date, platelet proteomic studies have focused on simply identifying subsets of platelet proteins, rather than on protein quantitation. The most commonly used techniques for protein quantitation via proteomic methods, involve image analysis of stained gels, which is not useful for membrane proteins. Other techniques include isotope-coded affinity tags (ICAT), in which a mass-encoded linker containing either 8 hydrogens (for one sample) or 8 deuteriums (for a second sample) is attached to reduced cysteine residues. In this case, each cysteinyl peptide appears as a pair of signals differing by the mass differential encoded in the mass tag, and the ratio of the signal intensities indicates the ratio of abundance of the proteins in the two samples from which the peptides originate. One problem with this approach is that not all proteins contain cysteine residues, and another potential problem is that the two samples are reacted with the reagent after protein isolation, which can introduce artifacts if the samples are not treated identically. This latter issue also applies to methods in which, for example, $^{18}O$ is incorporated into isolated proteins from one sample (Staes et al., *J Proteome Res* 3:786-791, 2004).

Thus, there remains a need for a method to identify and quantitate membrane-bound proteins in platelets as biomarkers for addiction, and other physiological disorders (e.g., early cardiovascular disease). As described herein, the unbiased proteomic approach to the identification of biomarkers for these disorders provides tools for diagnosis of various diseases. Additionally, platelet membrane protein profiling and quantitation is contemplated to provide novel approaches for ascertaining the efficacy of therapeutic agents and for discovering new targets for drug development.

II. Unbiased Proteomic Methods for the Identification and Quantitation of Platelet Membrane Proteins In this approach, a platelet membrane fraction is obtained using standard methods known in the art. The membrane fraction is then homogenized and subjected to strongly alkaline conditions to obtain membrane sheets substantially depleted of soluble and peripheral membrane proteins. The membrane samples are subsequently digested with a nonspecific protease, such as proteinase K, to yield a series of peptides with an optimal length for analysis by liquid chromatography and tandem mass spectrometry. The peptides derived from proteins in the platelet membranes are separated by microcapillary liquid chromatography (LC), and elute directly into a tandem mass spectrometer and are subjected to electrospray ionization (ESI). Because this system is based on liquid chromatographic separation, it is readily amenable to automation. As the complexity of the protein sample increases, the number of peptides generated upon digestion drastically increases, and the performance demand on the LC separation increases. To handle the peptide complexity, the inventors have successfully applied a multi-dimensional approach called Multidimensional Protein Identification Technology (MudPIT; Washburn et al., *Nat Biotechnol* 19:242-247, 2001). Briefly, the peptide mixture is loaded onto a biphasic chromatography column, which is packed in tandem with both strong cation exchange (SCX) and reverse phase (C18) chromatography material, and placed in-line with the mass spectrometer. In this configuration, peptides are step eluted from the SCX material onto the C18 material using increasing concentrations of salt. After each "step" elution from the SCX column, a reverse phase gradient is applied to the C18 column to elute the peptides by their hydrophobicity into the mass spectrometer. The number of automated sequential cycles of short salt pulses, followed by a reverse phase gradient, is determined by the complexity of the sample. As peptides are eluted into the mass spectrometer, they are ionized and mass spectra are acquired. If an ion exceeds the threshold, the mass spectrometer will selectively isolate the ion, subject the isolated ion to collision-induced dissociation with an inert gas, and then perform a second stage of mass analysis (tandem mass spectrometry or MS/MS). MS/MS spectra are analyzed using the following software analysis protocol: 2 to 3 software determines the charge state (+2 or +3) of multiply charged peptide spectra and deletes poor-quality spectra. Each MS/MS spectrum after 2 to 3 is searched against the RefSeq protein database (rat, mouse, human sequences) using SEQUEST. To minimize false positives, only proteins with three or more peptides exceeding the peptide filters are considered. DTASelect then assembles the peptide sequences into proteins and removes redundant protein sequences (Eng et al., *J Amer Soc Mass Spectrom*, 5:976-989, 1994; Sadygov et al., *J Prot Res*, 1:211-215, 2002; and Tabb et al., *J Prot Res*, 1:21-26, 2002). Mud-PIT facilitates increased separation capacity and decreased limits of detection to femtomole levels (Washburn et al., *Nat Biotechnol*, 19:242-247, 2001; and McCormick et al., *Anal Chem*, 69:767-776, 1997). Furthermore, recently developed methodologies facilitate the rapid identifications of covalent modifications phosphorylation, methylation, acetylation, and ubiquitination) of both soluble (MacCoss et al., *Proc Nat Acad Sci*, 99:7900-7905, 2002; Peng et al., *Nat Biotechnol*, 21:921-926, 2003; and Wu and MacCoss, *Opin Mol Ther*, 4:242-250, 2002) and membrane proteins (Wu et al., *Nat Biotechnol*, 21:532-538, 2003) in total cell lysates.

III. Application to Substance Abuse Disorders and Other Diseases

Alcohol and drug abuse present substantial social and economic problems for society as a whole. The identification of individuals who are heavily consuming alcohol or other licit (e.g., tobacco, prescription medicines) or illicit drugs (e.g., cocaine, marijuana), as well as the ability to monitor for relapse those individuals who are receiving treatment, requires objective biochemical markers of alcohol or drug use. Currently available markers for alcohol use primarily identify individuals who are addicted to alcohol, but are not necessarily sensitive for those who are drinking at hazardous levels but do not meet the criteria for alcohol dependence. The inventors have found that levels of various platelet membrane proteins provide sensitive and specific markers of alcohol or other drug consumption during the past 3-14 days, since these proteins reflect the physiological state of the body during the period of platelet formation, and are "turned over" along with the platelets with a half-life of approximately 5 days.

Certain platelet proteins are also indicators of platelet activation, which is considered to play a key role in the deterioration of the failing heart due to pathological development of thrombosis. These proteins and other platelet membrane proteins reflecting inflammatory processes are contemplated to provide sensitive early diagnostic markers of liver disease and cardiovascular disease, including hypertension, congestive heart failure, and chest pain of cardiac origin. Given the substantial cost to society of cardiovascular disease, and its role as the leading cause of death in the United States, the identification of biomarkers that are indicators of early-stage cardiovascular disease, and which correlate with disease severity represents an important goal.

With the methods of the present invention described in the experimental examples below, platelet membrane proteins can now be identified and quantitated in an unbiased manner using proteomic techniques. As a proof of concept, the platelet membrane protein MAO-B was identified by mass spectrometry, and this protein was quantitated, first by mass spectrometry in individuals during drinking, and after abstinence, and then by antibody techniques, in groups of individuals who were drinking at hazardous/harmful vs. non-hazardous levels. All or most of the other platelet membrane proteins are quantitated by mass spectrometry, using the method of spectral sampling. The sensitivity and specificity of differentially expressed proteins to identify groups of substance-using/abusing, vs. non substance-using individuals, is assessed by statistical methods known in the art.

Additional platelet-associated substance use (PASU) markers may be identified by using the protocols detailed in of the following examples and in Section II above. Briefly, platelets are obtained from blood samples drawn from control and experimental subjects using the method of Corash (*Psychopharmacol Bull*, 16:65-67, 1980). In one exemplary embodiment, the experimental subjects are individuals diagnosed with opiate addition (e.g., VICODIN) or known to have chronically misused opiates (e.g., continued use over and beyond that prescribed by initial attending physician). In another exemplary embodiment, the experimental subjects are individuals diagnosed with a benzodiazepine addiction (e.g., XANAX) or known to have chronically misused benzodiazepines. In some exemplary embodiments, the control subjects are individuals that have not taken opiates and benzodiazepine, respectively. In other embodiments, the control subjects are individuals that have attended a drug rehabilitation program.

After limited proteolysis of the platelet membrane proteins to generate peptide mixtures, the peptide mixtures are analyzed by MudPIT (e.g., employing liquid chromatography/tandem mass spectrometry). The peptides from each MS/MS spectrum are identified by searching a protein database, and are quantitated by spectral sampling. Platelet proteins are identified as substance use (PASU) markers when the spectrum count for a particular protein is lower or higher in the majority (e.g., >65%, >75%, >85, >90%, >95%, >98%) of the experimental samples as compared to the control samples.

PASU markers are also identified through a more sensitive and quantitative approach for measuring protein levels by mass spectroscopic methods. One can isotopically label megakaryocytic platelet progenitor cells in culture, and then in the presence of proper cytokines and growth factors, generate mature megakaryocytes that subsequently produce platelets in culture.

Megakaryocyte progenitors cells (CD34$^+$) are isolated from bone marrow, umbilical cord blood or granulocyte-colony stimulating factor (G-CSF) mobilized peripheral blood. Using a suitable cytokine cocktail in serum-free medium, functional platelets are generated in vitro (Ungerer et al., *CircRes*, 95:e36-e44, 2004). Alternatively, there are several hematopoietic cell lines established from patients with leukemia that are induced to produce erythrocytes, leukocytes, and/or thrombocytes (platelets). MEG-01 cells (ATCC CRL-2021) are cultured at $3.3 \times 10^5$ cells/ml in RPMI-1640 medium supplemented with 10% fetal bovine serum (FBS) at 37° C. in a humidified atmosphere of 5% $CO_2$ in an incubator. Cells are exposed to 100 ng/ml thrombopoietin (TPO) and 10 nM phorbol 12-myristate 13-acetate (PMA) for 3-10 days. Changes in cell morphology are observed under an inverted phase-contrast microscope. After ten days in culture, untreated MEG-01 cells (control) and MEG-01 cells exposed to TPO and PMA (treated) are pelleted and aliquots of each are subjected to MudPIT analysis.

MudPIT analysis identified 574 and 891 non-redundant proteins in control and treated MEG-01 cells, respectively, using a three-peptide minimum coverage selection criteria. Of the proteins identified, 378 proteins were identified in both cell cultures that largely consisted of nuclear and metabolic proteins, suggesting that the treated cell cultures still contained undifferentiated precursor and megakaryocytic cell types. Of the 513 identified proteins that were unique to treated cells, three of the candidate marker proteins identified in platelets (CGI-51 protein, oxoglutarate dehydrogenase and NADH dehydrogenase) were expressed. Overall, treated MEG-01 cells expressed 34.3% of the proteins identified in MudPIT analysis of standard platelets.

Stable isotope labeling by amino acids in cell culture (SILAC) is achieved using $^{15}N$ or $^{13}C$ amino acids added to culture media to label proteins. Proteins from cell cultures grown under "heavy" media conditions are then added (1:1) as an internal standard to protein mixtures from cells grown in media with natural abundance isotopes and analyzed with liquid chromatography and tandem mass spectrometry (MS/MS). Comparison of ion chromatograms of the unlabeled and isotope-enriched peptide pairs yield quantitative protein ratios (Wu et al., *Anal Chem,* 76:4951-4959, 2004).

Alternatively or additionally, a polyclonal antibody is raised in rabbits immunized with a PASU marker peptide (~10-20 amino acid fragment of a PASU marker protein) conjugated to a carrier (e.g., keyhole limpet hemocyanin). The polyclonal serum is affinity purified against the immunizing PASU marker peptide and testing by immunoblot of polyacrylamide gel-separated platelet lysate. Serum that bind to a protein of the expected molecular weight, are used to analyze the relative expression level of the PASU marker protein in control and experimental samples, as compared to total protein content or control protein content (e.g., p110).

EXPERIMENTAL

The following examples are provided in order to demonstrate and further illustrate certain preferred embodiments and aspects of the present invention and are not to be construed as limiting the scope thereof.

In the experimental disclosure which follows, the following abbreviations apply: eq (equivalents); M (Molar); μM (micromolar); N (Normal); mol (moles); mmol (millimoles); μmol (micromoles); nmol (nanomoles); g (grams); mg (milligrams); μg (micrograms); ng (nanograms); l or L (liters); ml (milliliters); μl (microliters); cm (centimeters); mm (millimeters); μm (micrometers); nm (nanometers); ° C. (degrees Centigrade); U (units), mU (milliunits); min. (minutes); sec. (seconds); % (percent); kb (kilobase); bp (base pair); cpm (counts per minute); Ci (Curies); PCR (polymerase chain reaction); HHAU (hazardous/harmful alcohol use); MAO (monoamine oxidase), CGI-51 (sorting and assembly machinery 50 kDa protein); GATM (glycine amidinotransferase); OGDH (oxoglutarate dehydrogenase); BZRP (peripheral benzodiazepine receptor); GSN (gelsolin); NDUFA8 (NADH dehydrogenase); GRIM19 (cell death regulatory protein 19); CDT (carbohydrate deficient transferrin); hpPK (high pH proteinase K); MudPIT (multidimensional protein identification technology); HPLC (high performance liquid chromatography); MS (mass spectrometry); GGT (γ-glutamyltransferase); and ASAT (alanine/serine aminotransferase).

Example 1

Preparing Platelet Membrane Proteins for Proteomic Analysis

Platelets were obtained from a local blood bank within 72 hours after the platelets became out-dated, or platelets were obtained using the method of Corash (*Psychopharmacol Bull,* 16:65-67, 1980) from blood samples drawn from study subjects. Platelets were pelleted by centrifugation at 6000×g and then resuspended by addition of ice-cold distilled water and homogenized in a glass/Teflon homogenizer for 1 min at 600 rpm. The homogenate was frozen overnight at −80° C. The next day the homogenate was thawed and platelet membranes were pelleted by centrifugation at 44,000×g for 30 min. The supernatant was discarded and the membrane pellet was resuspended in 10 mM $K_iPO_4$ buffer, pH 7.4 (1.5 ml per 10 ml original volume) by sonication. The protein concentration was determined (BCA assay; Pierce, Rockford Ill.) and the homogenate diluted to approximately 1 mg/ml in 10 mM $K_iPO_4$ buffer. Homogenate aliquots of 1 ml were centrifuged at 44,000×g and the resulting pellets frozen at −70° C.

After thawing and resuspension of the platelet membranes at 1 mg protein/ml in 200 mM $Na_2CO_3$, pH 11, with five passes through an insulin syringe (28, 29 or 30 gauge), the suspension was incubated on ice for 1 h. The membrane sample was then adjusted to 8 M urea, and reduced and alkylated as previously reported (Washburn et al., *Nat Biotechnol,* 19:242-247, 2001). Proteinase K (5 μg) was added to the sample, which was then incubated at 37° C. for 3 h in a Thermomixer (Brinkmann, Westbury, N.Y.). An additional aliquot of proteinase K (5 μg) was added and the sample was incubated at 37° C. for 1.5 h. The reaction was quenched with formic acid (5% final concentration) and microcentrifuged at 18,000×g at 4° C. for 15 min to remove particulates.

Example 2

Proteomic Analysis of Platelet Membrane Proteins

Platelet membrane proteins were analyzed by the technique of multidimensional protein identification technology (MudPIT) as shown in FIG. 1 and as described (Wu and Yates, *Nat Biotech,* 21:262-267, 2003). The protein digest (supernatant from Example 1) was pressure-loaded onto a fused-silica capillary desalting column containing 5 cm of 5-μm Polaris C18-A material (Metachem, Ventura, Calif.) packed into a 250-μm inner diameter (i.d.) capillary with a 2-μm filtered union (UpChurch Scientific, Oak Harbor, Wash.). The desalting column was washed with buffer containing 95% water, 5% acetonitrile, and 0.1% formic acid (all vol/vol). The desalted proteins were then eluted onto the rear end of a triphasic chromatography column using 20% water, 80% acetonitrile, and 0.1% formic acid. The triphasic column consisted of a 100-μm i.d. capillary with a 5-μm pulled tip, packed in the following order from the tip: (i) 7 cm 5-μm Aqua C18 material (Phenomenex, Ventura, Calif.), (ii) 3 cm 5-μm Partisphere strong cation exchanger (Whatman, Clifton, N.J.), and (iii) 3 cm 5-μm hydrophilic interaction chromatography material (PolyLC, Columbia, Md.).

Once loaded with the peptide digests, the column was placed inline with an Agilent 1100 quaternary HPLC (Palo Alto, Calif.) and analyzed using a modified 12-step separation as described (Washburn et al., *Nat Biotechnol,* 19:242-247, 2001). The buffer solutions used were 5% acetonitrile-0.1% formic acid (buffer A), 80% acetonitrile-0.1% formic acid (buffer B), and 500 mM ammonium acetate-5% acetonitrile-0.1% formic acid (buffer C) (all vol/vol). Step 1 consisted of a 100-min gradient from 0 to 100% buffer B. Steps 2-11 had the following profile: 3 min of 100% buffer A, 2 min of x % buffer C, a 10-min gradient from 0 to 15% buffer B, and a 97-min gradient from 15% to 45% buffer B. The 2-min buffer C percentages (x) were 10%, 15%, 20%, 25%, 30%, 35%, 40%, 45%, 50%, 60%, respectively, for the 12-step analysis. For the final step, the gradient contained 3 min of 100% buffer A, 20 min of 100% buffer C, a 10-min gradient from 0 to 15% buffer B, and a 107-min gradient from 15% to 70% buffer B.

As peptides eluted from the microcapillary column, they were electrosprayed directly into an LCQ-Deca mass spectrometer (ThermoFinnigan, Palo Alto, Calif.) with the application of a distal 2.4 kV spray voltage. A cycle of one full-scan mass spectrum (400-1,400 m/z) followed by three data-dependent MS/MS spectra at a 35% normalized collision energy was repeated continuously throughout each step of the multidimensional separation. The application of mass spectrometer scan functions and HPLC solvent gradients was controlled by the Xcaliber data system (ThermoFinnigan, Palo Alto, Calif.) as shown in FIG. 1.

MS/MS spectra were analyzed using the following software analysis protocol: 2 to 3 determined the charge state (+2 or +3) of multiply charged peptide spectra and deleted poor-quality spectra. Each MS/MS spectrum after 2 to 3 was searched against the RefSeq protein database (rat, mouse, human sequences) using SEQUEST (Eng et al., *Spectrom*, 5:976-989, 1994). DTASelect selected peptide sequences from +1, +2, and +3 charged peptide precursors with normalized SEQUEST XCorr scores>0.3 (MacCoss et al., *Anal Chem*, 74:5593-5599, 2002) and $\Delta C_n > 0.1$. To minimize false positives, only proteins with two or more peptides exceeding the peptide filters were considered. DTASelect then assembled the peptide sequences into proteins and removed redundant protein sequences (Tabb et al., *J Proteome Res*, 1:21-26, 2002). For example, if ten different peptides identified a gene locus and three of the ten were also present in a second gene locus, only the locus with the greater number of peptides was listed, and the subset locus was removed. If all ten peptides were identified in two gene loci, both loci were listed but only counted as single protein identifications. Table 1 provided in FIG. 9 lists the 534 proteins that were identified, using at least two peptides from each protein, in the platelet membrane preparations and also notes the spectrum count of peptides (which provides a measure of abundance). FIG. 2 shows the peptides that were used to identify MAO-B in the platelet membrane preparation.

Example 3

Quantitation of Platelet Proteins by Mass Spectrometry in Control and Experimental Groups Several shotgun proteomic studies have suggested a quantitative relationship between protein abundance and the sampling process (Pang et al., *Proteome Res*, 1:161-169, 2002; Gao et al., *J Proteome Res*, 2:643-639, 2003; and Florens et al., *Nature*, 419:520-526, 2002). Thus, highly abundant proteins are sampled more frequently resulting in greater peptide sequence coverage and greater spectral sampling. Therefore, good data can be generated for high abundance proteins with fewer experiments. Likewise, greater sequence coverage and spectral sampling can be achieved for low abundance proteins by increasing the number of experiments. Recently, a direct relationship between the level of sampling (number of peptides) observed for a protein and the relative abundance of the protein in the mixture was demonstrated to have a linear dynamic range over 2 orders of magnitude by using the number of spectra (spectral sampling) acquired for each protein (Liu et al., *Anal Chem* 76:4193-4201, 2004). Spectral sampling was shown to be very accurate at measuring large changes between proteins but less accurate at measuring small differences between proteins (Liu et al., supra 2004; and Qian et al., *Proteomics [Epub ahead of print]*, 2005). With this in mind, the inventors have used spectral sampling as a preliminary determinant of protein abundance and as one of the selection criteria for target proteins in the platelet membrane proteome for direct quantification. Table 1 provided in FIG. 9 contains the GENBANK database reference information, the descriptive name, the spectrum count (indicating abundance) and sequence coverage of 514 proteins with 2 peptide coverage and 218 proteins with 3-peptide coverage that were identified in the platelet preparations analyzed during development of the present invention. This analysis was applied to platelet preparations that were generated from blood samples provided by subjects who entered alcohol treatment programs. Two consecutive blood samples were collected from such subjects. The first sample (A) was collected upon entry into the program (on average, within 3 days after the last drinking bout). The second sample (B) was collected fourteen days after the first sample, and the subjects were in the inpatient program during the intervening days between the first and second sample. The consecutive samples were used as a means to identify "state" markers for high alcohol consumption. Of particular interest were markers that would demonstrate, in a reversible fashion, whether the individual had been drinking recently (i.e., within the last 2-5 days) or had maintained abstinence or low levels of alcohol intake over the preceding 1-3 weeks. Such a marker would be useful in both screening for recent alcohol consumption and for monitoring the success of treatment during periods between scheduled appointments with a therapist. In an exemplary analysis, data from seven individuals who had A and B samples available for assay were utilized. These individuals had stopped drinking for an average period of 2.2 days. Their average daily ethanol intake during the 30 days prior to entering treatment was 205.7 g/day (range 93-378 g/day). Three subjects, who had low or no alcohol consumption during the last 30 days, were also examined. The average daily ethanol consumption of these individuals was 6.5 g/day (range 0-19 g/day) over the last 30 days.

The criteria for choosing a platelet protein for as a biomarker (see Table 2) was that the spectrum count for a particular protein had to be lower or higher in 85% of the A samples compared to the B samples. In addition, the spectral count of the B samples had to resemble the spectral count (or be approaching the spectral count) for that protein in the samples of the low or no alcohol consumers. One of the most abundant of these differentially expressed proteins was MAO-B; other platelet mitochondrial proteins were also identified. MAO-B was chosen as an example because of its consistently high spectral counts and sequence coverage. As described herein, the inventors have demonstrated that MAO protein levels (but not platelet MAO activity), can be used as a "state" marker of hazardous/harmful alcohol use (HAAU).

TABLE 2

Biomarkers for Hazardous/Harmful Alcohol Use (HAAU)

| Protein | SEQ ID NO | Locus | Spectrum Count | Sequence Coverage |
|---|---|---|---|---|
| Monoamine oxidase, (MAO) | 1 | gi 38202207 | 44 | 16.2% |
| CGI-51 protein | 18 | gi 31542301 | 13 | 13.0% |
| Glycine amidinotransferase (GATM) | 19 | gi 4503933 | 12 | 10.4% |
| Oxoglutarate dehydrogenase (OGD4) | 20 | gi 33563270 | 12 | 3.8% |
| Peripheral benzodiazepine receptor (BZRP) | 21 | gi 4502481 | 6 | 11.8% |
| Gelsolin isoform a (GSN) | 22 | gi 4504165 | 5 | 22.0% |
| NADH dehydrogenase (DNUFA8) | 23 | gi 7657369 | 5 | 32.6% |
| Cell death-regulatory protein 19 (GRIM19) | 24 | gi 21361822 | 4 | 10.1% |

The peptide mixture produced by hpPK treatment of the platelet membranes was analyzed by MudPIT and 218 proteins were identified with a three-peptide minimum (>95% confidence). A complete list sorted alphabetically is provided in Table 1 shown as FIG. 9. Five of these proteins were chosen for further analysis, as protein markers for alcohol abuse. All five proteins were significantly lower in subjects while they were consuming high levels of alcohol compared to these protein levels measured after two weeks of abstinence in an inpatient alcohol treatment facility. Furthermore, all are constituents of platelet mitochondria, suggesting that alcohol use compromises platelet mitochondrial function. The five proteins of interest in order of their spectral abundance were the neurotransmitter metabolizing monoamine oxidase (MAO-B), CGI-51 protein also known as the sorting and assembly machinery (SAM50) protein of the translocase of the outer mitochondrial membrane (TOM), glycine amidinotransferase (GATM), oxoglutarate dehydrogenase (OGDH) and the peripheral benzodiazepine receptor protein (PBDR or BZRP). The CGI-51 protein is a key protein involved in the assembly of pre-proteins into the TOM complex, and is essential for cell viability (Kozjak et al., *J Biol Chem*, 278:48520-48523, 2003). Amidinotransferase (transamidinase, L-arginine:glycine amidinotransferase) is an enzyme that catalyses the first step in creatine synthesis (Walker, *Adv Enzymol*, 50:177-242, 1979). Oxoglutarate dehydrogenase (α-ketoglutarate dehydrogenase) is a thiamine-dependent enzyme that is the rate-limiting step in the TCA cycle and has been implicated in the generation of reactive oxygen species in mitochondria (Tretter and Adam-Vizi, *J Neurosci*, 24:7771-7778, 2004). The peripheral benzodiazepine receptor is an important mitochondrial pore protein involved in steroidogenesis and apoptosis (Papadopoulos, *Endocr Res*, 30:677-684, 2004; and Jorda et al., *Apoptosis*, 10:91-104, 2005).

Example 4

Generating an Antibody to MAO-B

A polyclonal antibody was raised in rabbits immunized with the peptide TNGGQERKFVGGSGQC (SEQ ID NO:26), corresponding to amino acids 202-216 in MAO-B, plus a C-terminal cysteine to allow conjugation to keyhole limpet hemocyanin. The resulting serum was affinity purified against the immunizing peptide immobilized on iodoacetamide-linked agarose gel columns (SulfoLink; Pierce, Rockford, Ill.). Other peptides corresponding to immunogenic sequences of MAO protein can also be used to immunize rabbits or mice for the purpose of obtaining antibodies. The MAO-B antibody was characterized using standard SDS-PAGE methods. Samples of platelet membranes and recombinant human MAO-B protein were solubilized in 100 μl 2% SDS by boiling for 3 min. Protein concentrations were determined, followed by addition of 25 μl 5×SDS sample buffer (0.3125 M Tris, 10% SDS, 750 mM DTT, 7.5 M urea, 50% glycerol, 0.05% bromophenol blue) and boiling to denature proteins. Protein aliquots (2-20 μg per well for platelets; 10 and 20 ng recombinant MAO-B) were loaded onto 8-10% SDS-PAGE gels and proteins were separated and transferred to nitrocellulose membranes. Blots were blocked in 5% nonfat dry milk in Tris-buffered saline, pH 7.5, and 0.1% Tween 20 (NFDM-TBST), washed twice in washing buffer (TBST) and then incubated for 1 hr at room temperature with rabbit polyclonal antisera (1:1000 dilution in 5% NFDM-TBST). After incubation, blots were washed twice and then incubated with horseradish-peroxidase-conjugated anti-rabbit IgG (BioRad, Hercules, Calif.) diluted 1:10,000 in NFDM-TBST. Bound antibodies were detected using enhanced chemiluminescence (Renaissance, Dupont-NEN, Boston, Mass.) and exposure to Kodak X-Omat film. The optical density (OD) of immunoreactive bands was determined and analyzed using Molecular Analyst software (BioRad, Hercules, Calif.). FIG. 3 shows that this antibody recognizes a polypeptide with apparent molecular mass of ~59 kDa (corresponding to the calculated molecular mass of MAO-B) in preparations of recombinant MAO-B and platelet membranes. This value is in agreement with the molecular weight predicted from the full amino acid sequence of MAO-B. Although the methods described herein relate to the generation of a polyclonal antiserum for MAO, the present invention is not limited to these methods. In further embodiments, monoclonal antibodies are generated for the purpose of detecting the MAO-B protein.

Example 5

Measurement of Platelet MAO-B Protein Levels in Individuals Consuming Different Amounts of Alcohol The antibody to MAO-B was used to measure the amount of MAO-B protein in platelet samples obtained from 237 subjects (143 males and 94 females) recruited in the WHO/ISBRA Study of State and Trait Markers of Alcohol Use and Dependence. This study was established in 1988 to assess, in a multi-center trial, markers of recent alcohol use (state markers) and trait markers of predisposition to alcohol dependence (Glanz et al., *Alcohol Clin Exp Res*, 26:1047-1061, 2002). Immunoblotting was used to assess the levels of platelet MAO-B protein in individuals characterized as harmful/hazardous drinkers and in those characterized as drinking amounts of alcohol below these levels (non-hazardous drinkers). Subjects' alcohol consumption was classified as nonhazardous or hazardous/harmful using established criteria (Saunders et al., *Compr Psychiatry*, 41:95-103, 2000): for males, drinking >40 grams of ethanol per day (g/day) is considered hazardous and drinking >80 g/day is considered harmful. For females, drinking >20 g/day is considered hazardous and drinking >60 g/day is considered harmful. The consumption thresholds for hazardous drinking were chosen to reflect levels at which health hazards of drinking begin to increase according to the National Health and Medical Research Council (Saunders et al., supra, 2000). The consumption thresholds for harmful drinking where chosen to reflect levels at which physical harm becomes likely according to published reports (Saunders et al., *Addiction*, 88:349-362, 1993).

Platelets were isolated from blood samples collected from each individual as described (Glanz et al., *Alcohol Clin Exp Res*, 26:1047-1061, 2002), and homogenates were kept frozen at −80° C. The homogenate was thawed and platelet membranes were pelleted by centrifugation at 44,000×g for 30 min. The supernatant was discarded and the membrane pellet was resuspended in 10 mM $K_iPO_4$ buffer, pH 7.4 (1.5 ml per 10 ml original volume) by sonication. The protein concentration was determined (BCA assay; Pierce, Rockland Ill.) and the homogenate diluted to approximately 1 mg/ml protein in 10 mM $K_iPO_4$ buffer. Homogenate aliquots of 1 ml were centrifuged at 44,000×g and the resulting pellets frozen at −70° C. until used.

For each subject, two amounts of platelet protein (4 and 8 µg) were separated by SDS-PAGE and transferred to nitrocellulose membranes. Each blot also contained increasing amounts of a standard platelet membrane preparation (2, 5, 10 and 20 µg protein). A standard curve of immunoreactive intensity was established (3-parameter Hill equation using non-linear curve fitting (SigmaPlot, SPSS Inc., Chicago, Ill.). Quantification of sample immunoreactive band intensities was performed using the adjusted OD of the sample bands relative to the standard platelet protein standard curve. Results were expressed as µg equivalents of the MAO immunoreactivity (relative to the standard platelet preparation) per µg of total protein.

FIG. 4A shows an immunoblot of platelet MAO-B protein and platelet p110 protein in an individual during the period of consumption of high amounts of alcohol (40490A) and following two weeks of abstinence (40490B). BRIEFLY, a SDS-PAGE gel (10%) was loaded with solubilized protein from a standard platelet preparation (5, 10, 20 and 40 µg), and solubilized protein from two sample platelet preparations (10 and 20 µg each of "A" and "B" samples from subject 40490). After electrophoresis, the platelet proteins were transferred, and the blot was cut at the level of the 75 kDa molecular weight marker (dotted line). Immunoblotting for p110 and MAO-B was carried out separately, and the blot re-assembled before development with enhanced chemiluminescence. The last lane was loaded with ~1 µg recombinant MAO-B, and thus this lane does not contain p110 protein.

FIG. 4B presents the means (±SE) for the µg equivalents of MAO/µg protein, for male and female subjects exhibiting hazardous/harmful levels ethanol consumption versus male and female subjects who are nondrinkers or exhibit non-hazardous ethanol consumption. Overall, even in non-drinkers, MAO-B protein levels were higher in the platelets of female subjects compared to male subjects. In both genders, however, MAO-B protein levels were lower in individuals who exhibited hazardous or harmful ethanol consumption, compared to those who were nondrinkers or exhibited non-hazardous ethanol consumption, as was initially determined by proteomic techniques (Table 2). Specifically, female and male subjects consuming alcohol at hazardous levels (>20 g/day and >40 g/day respectively) and harmful levels (>60 g/day and >80 g/day respectively) were observed to have significantly lower platelet MAO-B protein levels compared to nondrinkers and non-hazardous drinkers ($P<<0.01$ versus nondrinkers/non-hazardous drinkers by ANOVA with post-hoc Tukey tests). FIGS. 4A and 4B also show (inset) that while platelet MAO-B was lower in individuals consuming alcohol at harmful/hazardous levels within 3 days of blood sampling, the level of platelet MAO-B returned to control levels (non-drinking/non-hazardous drinking) when male subjects (n=14) abstained from alcohol for 14 days.

Example 6

Sensitivity and Specificity of MAO-B Protein Concentration as a Diagnostic Marker for Hazardous/Harmful Alcohol Use (HHAU)

Figure 5:
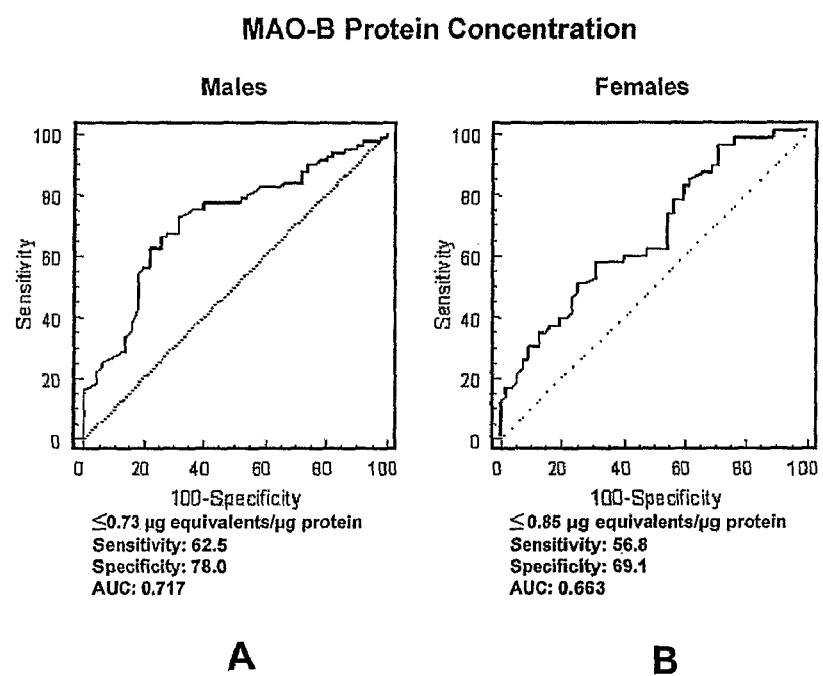
FIG. 5 depicts ROC curves for platelet MAO-B protein concentration to discriminate hazardous/harmful alcohol use (HHAU) from non-hazardous alcohol intake in men (panel A) and women (panel B). Sensitivities and specificities are those at the listed optimal cutoff levels of MAO-B protein concentration. Curves were generated using MedCalc and SPSS.

Receiver operating characteristic (ROC) analysis was used to determine the sensitivity and specificity of platelet MAO-B protein, as a marker to identify male and female hazardous/harmful alcohol drinkers. As shown in FIG. 5, MAO-B protein level was able to identify hazardous/harmful male drinkers with a sensitivity=63% and a specificity=78% at a cutoff level of 0.73 µg equivalents/µg protein (threshold value for the methods of Example 5). MAO-B protein level identified hazardous/harmful female drinkers with a sensitivity=57% and a specificity=69% at a cutoff level of 0.85 µg equivalents/µg protein (threshold value for the methods of Example 5). Accuracy, a measure of overall performance, was calculated from the percentages of true positives and true negatives correctly identified relative to the total number of subjects. MAO-B protein showed an accuracy of 69% in males and 54% in females.

Example 7

Independent Association of Variables with Platelet MAO-B Concentration Determined by Logistic Regression Analysis One reason for low specificity and/or sensitivity of a marker for discriminating a particular phenotype such as harmful/hazardous alcohol intake is the existence of other factors that affect the marker levels or characteristics. For example, smoking has been reported to affect % CDT (percent carbohydrate deficient transferrin) levels (Whitfield et al, *Clin Chem* 44:2480-2489, 1998), and non-alcoholic liver disease or damage can influence the levels of liver enzymes such as γ-glutamyltransferase (GGT) or alanine/serine aminotransferase (ASAT). Logistic regression analysis is a statistical method that allows for the determination of factors that are independently associated with a particular outcome, such as the level of MAO-B protein. Table 3 lists the variables that were used in logistic regression analyses as potential predictors of an individual having a protein level of MAO above the cutoff for determining harmful/hazardous drinking. The outcome variable of the MAO protein cutoffs was determined from ROC analyses for discriminating harmful/hazardous drinking in males or females. Manufacturer-recommended cutoffs for males and females were used for discriminating individuals utilizing % CDT, ASAT or GGT as predictor variables. Each predictor variable was initially analyzed univariately using a logistic regression model to predict the protein level of MAO-B. Significance levels were based on Type III Analysis of Effect Wald Chi-Square statistics.

Predictor variables that had a significance level of less than 0.2 were considered for inclusion in a multivariate logistic model to predict an individual having a protein level of MAO-B above the cutoff. A forward stepwise regression search algorithm was utilized to determine final multivariate models. In this method, potential effects enter and exit the model based on the score chi-square statistic. The stepwise selection is done in a forward manner identifying one potential effect at a time to either enter or exit the model. The cut point for entrance and exit was set at 0.05. Analyses were done for males and females separately. Having platelet MAO-B protein concentrations below the optimal cutoff concentrations to identify hazardous/harmful alcohol use (HHAU) as determined by ROC analyses (0.73 µg equivalents/µg protein; see ROC analyses, above), was taken as the positive diagnostic outcome. The stepwise logistic regression analysis of male subjects revealed a significant association of the cut-off variable with HHAU, with $V_{max}$ of MAO activity, with total body water (TBW) and with marijuana use during the last 30 days (Table 4). The association of platelet MAO concentration cutoff with TBW was due to the covariance of this measure with gender (total body water is higher in males compared to females). The finding that marijuana use was associated with the platelet MAO concentration cutoff was unanticipated, but has since been controlled for in later analyses.

TABLE 3

Variables Entered Into Logistic Regression Analysis For Platelet MAO-B Protein Cut Off[a]

Non-alcohol clinical

Age
Total body water (TBW)
Body mass index (BMI)
Regular exercise
Medical history[b]

enlarged liver
Hepatitis
Hyperlipidemia
convulsion (epilepsy)
Vitamin deficiency
Emphysema

TABLE 3-continued

Variables Entered Into Logistic Regression Analysis For Platelet MAO-B Protein Cut Off[a]

Arthritis
High blood pressure
Prescription drug use[c]

Seizure disorder drugs
Dietary supplements
Antidepressants
Other drugs[c]
Non-prescription drug use[d]

marijuana use
Cocaine use
Nicotine use
(non-, ex- or current smoker)
Clinical diagnoses (DSM-IV)

current alcohol dependence
current alcohol abuse
lifetime[b] marijuana dependence
lifetime cocaine dependence
lifetime ASPD
lifetime conduct disorder
lifetime major depression
lifetime familial depression
alcohol-related variables family history of alcohol dependence
familial alcohol dependence
hazardous harmful alcohol use (HHAU)[e]
Biochemical marker variables Platelet MAO activity affinity ($K_m$)
log transformed platelet MAO activity max velocity [log($V_{max}$)]
Platelet MAO-B protein concentration
Alanine/serine aminotransferase (ASAT)
γ-Glutamyltransferase (GGT)
carbohydrate-deficient transferrin (% CDT)
ASAT cut off[f]
GGT cut off[f]
CDT cut off[f]

[a]Platelet MAO-B cut off values of 0.73 µg equivalents/µg protein and 0.85 µg equivalents/µg protein for males and females, respectively, that identify hazardous/harmful alcohol use (HHAU) from nondrinker/non-hazardous alcohol use (ROC analysis)
[b]Diagnosed with given medical condition at any time during life
[c]Other medications for: Parkinson's disease, diuretics/antidiuretic, blood coagulation, digestion/evacuation, mania (lithium), diabetes, replacement hormone therapy, infection, cardiovascular disease, psychosis, seizures, allergies, pain (antipyretics, analgesics), anxiety (benzodiazepines), sympathetic and parasympathetic drugs and dietary supplements
[d]use/abuse during previous 30 days
[e]hazardous/harmful alcohol use defined as >20 g/day for females and >40 g/day for males
[f]literature reported cut off values for detecting recent hazardous/harmful alcohol use, ASAT (40 U/L), GGT (40 U/L), % CDT (2.6%)

TABLE 4

Logistic Regression Models For Being Above The Platelet MAO-B Protein Concentration Cut Off For Hazardous/Harmful Alcohol Use (HHAU)

| Variables | df | Estimate | S.E. | Wald $\chi^2$ | P | OR | 95% Confidence Limits |
|---|---|---|---|---|---|---|---|
| Males | | | | | | | |
| TBW | 1 | −0.16 | 0.06 | 7.46 | 0.006 | 0.86 | 0.77-0.96 |
| log($V_{max}$) | 1 | 5.25 | 1.59 | 10.85 | 0.001 | 189.82 | 8.37-999 |
| marijuana use | 1 | 2.23 | 0.66 | 11.30 | <0.001 | 9.33 | 2.24-34.29 |
| HHAU | 1 | −1.62 | 0.57 | 8.11 | 0.004 | 0.20 | 0.07-0.60 |
| Females | | | | | | | |
| conduct disorder | 1 | 1.83 | 0.90 | 4.18 | 0.04 | 6.23 | 1.08-36.02 |
| other medication | 1 | −1.59 | 0.67 | 5.69 | <0.02 | 0.20 | 0.06-0.75 |
| HHAU | 1 | −1.65 | 0.83 | 3.99 | <0.05 | 0.19 | 0.04-0.97 |

Logistic regression analyses (SPSS) were performed to explore the contribution of the variables listed in Table 7 to the odds of platelet MAO protein levels being above the cut off values for HHAU in men and women. The multiple logistic regression models were obtained by the purposeful selection method. Prior to the model building process, univariate and bivariate statistical methods (e.g., means, histograms, t-tests, Chi-squares) were implemented to screen the data. Then, all possible bivariate regressions with the independent variables were fit. Variables that are significant at the $\alpha=0.20$ level are included into the full model. Using the log-likelihood ratio test, each independent variable was then added sequentially and retained in the model if it was significant at less than the $\alpha=0.10$ level. As variables were added, their potential as confounding variables was assessed by calculating a change in the coefficients of the other variables in the model. Variables that produced changes greater than 15% were considered confounders and left in the model. This process was repeated until all covariates were included, resulting in a primary main effects model. At this point, meaningful interaction terms were constructed, and their statistical significance evaluated using the log likelihood ratio test. Those significant at the $\alpha=0.05$ level were included in the model. Non-linear terms were either collapsed into meaningful categories or mathematically transformed. Finally, the model's fit and performance was assessed with a series of goodness of fit tests (e.g., Studentized jackknife residuals vs. predicted values, Cook's Distances vs. predicted values, leverage vs. predicted values). Analyses were performed using SAS version 8.1, SPSS version 12.0, and STATA version 6.0 software.

As shown in Table 4, logistic regression analyses in female subjects on the platelet MAO-B protein concentration cutoff for HHAU (above 0.83 μg equivalents/μg protein) revealed an association with HHAU, with conduct disorder, and with the use of prescription medication. Examination of the prescription medications taken by the female subjects included in this analysis did not reveal any particular medication that prevailed over others and thus, this variable could not be adjusted for in subsequent analyses. However, the association of platelet MAO-B protein concentration cutoff with conduct disorder in females was taken into account in later analyses.

Example 8

Sensitivity and Specificity of MAO-B Protein Level Alone and in Conjunction with CDT, GGT and ASAT Measurements for Identifying Heavy Alcohol Consumption Serum samples from 205 subjects (Table 5) for whom platelet MAO-B protein concentrations were determined were assayed for % CDT concentrations using a turbidometric immunoassay (% CDT; BioRad, Hercules, Calif.). GGT and ASAT were assayed by reflectance spectrophotometry using a Vitros 250 Analyzer (Ortho Clinical Diagnostics, Rochester, N.Y.) as described (Conigrave et al., *Alcohol Clin Exp Res*, 26:332-339, 2002). Correlation analysis on all of these markers was performed. Table 6 shows that platelet MAO-B protein levels were not significantly correlated with any of the other markers. These results indicate that platelet MAO-B protein levels, % CDT, GGT and ASAT levels can provide independent markers of harmful/hazardous alcohol drinking (although GGT and ASAT, as well as % CDT and ASAT, were significantly correlated in both genders).

TABLE 5

Subject Population Characteristics For Measures Of Platelet MAO-B Protein, % CDT, GGT And ASAT

| Characteristic | Male | | Female | |
|---|---|---|---|---|
| No. of Subjects | 123 | | 82 | |
| Mean Age (range) | 39 (18-60) | | 39 (18-60) | |
| Race | | | | |
| White | 104 | | 75 | |
| Black | 5 | | 4 | |
| Other | 14 | | 3 | |
| Ethanol Consumption | g/day | N | g/day | N |
| Nondrinker/Nonhazardous | <40 | 50 | <20 | 54 |
| Hazardous/Harmful | >40 | 73 | >20 | 28 |
| Current Alcohol Abuse | | 71 | | 24 |
| Current Alcohol Dependence | | 63 | | 23 |
| Smoking Status | | | | |
| Non-Smoker | | 21 | | 23 |
| Ex-Smoker | | 16 | | 21 |
| Current Smoker | | 86 | | 38 |
| Major Depression | | 22 | | 24 |
| ASPD | | 29 | | 15 |
| Conduct Disorder | | 13 | | 7 |
| Other Drug Dependence | | 21 | | 10 |

TABLE 6

Correlations Between Biomarkers Of Alcohol Use

| | % CDT | lnGGT | lnASAT |
|---|---|---|---|
| Males | | | |
| Platelet MAO-B concentration | −0.185 | −0.254 | −0.127 |
| % CDT | | 0.249 | 0.444** |
| lnGGT | | | 0.705** |
| Females | | | |
| Platelet MAO-B concentration | −0.084 | −0.150 | −0.188 |
| % CDT | | 0.192 | 0.270** |
| lnGGT | | | 0.576** |

**Correlation is significant at the <0.01 level

The correlations between MAO protein and the markers GGT and AST were examined and summary statistics computed on both the original and natural logarithmic (lNGGT and lnASAT) scales. A logarithmic transformation was used because the marker distributions were positively skewed. Platelet MAO-B protein concentration was poorly correlated with serum % CDT and plasma GGT levels in males, and not correlated at all in females. Moreover, in neither gender was platelet MAO-B protein concentration correlated with plasma ASAT levels. % CDT was significantly correlated with ASAT in both genders. More importantly, GGT and ASAT were highly correlated in both genders. This is not unexpected since both GGT and ASAT are elevated following liver damage (which is often seen in alcoholics). The lack of correlation between platelet MAO-B protein concentration and ASAT levels in this population suggests that these two measures are providing different information about alcohol intake. Based on these findings, the inventors have concluded that separate comparisons between MAO-B protein concentration, % CDT, GGT and ASAT are warranted.

Table 7 shows the results of the ROC analyses for CDT (expressed as the percentage of total serum transferrin levels; % CDT), ln GGT and in ASAT to detect HHAU in the 205 subjects for whom platelet MAO-B protein concentrations have been measured. Data presented are the sensitivity, specificity and area under the ROC curve (AUC) for each marker, listed separately for males and females. As a measure of the overall performance of the markers, accuracy was calculated from the percentage of true positives and true negatives correctly identified, relative to the total number of subjects. Based on the association of platelet MAO-B protein concentration with marijuana use in males and conduct disorder in females (see logistic regression), ROC analyses were also performed on data sets that excluded male subjects who had used marijuana in the last 30 days (excluded n=32) or female subjects with a lifetime history of conduct disorder (excluded n=10). These data show that, in males, all markers exhibited specificities superior to their sensitivities. Platelet MAO-B protein concentration performed better than % CDT and ln GGT and equally as well as ln ASAT in identifying hazardous/harmful alcohol intake (accuracy: 69.2% vs. 60.8%, 64.7% and 69.2%, respectively). It should be noted that when recent marijuana users were excluded from these data (based on the logistic regression analysis), although the accuracy of all markers improved, platelet MAO-B protein concentration now demonstrated the highest accuracy, achieved primarily from an increase in sensitivity (62.5% sensitivity in all subjects vs. 84.5% sensitivity in subjects who did not use marijuana).

TABLE 7

ROC Analyses To Differentiate Hazardous/Harmful Alcohol Intake From Non-hazardous Alcohol Intake*

| Biomarker | Sens | Spec | AUC | Acc | Sens | Spec | AUC | Acc |
|---|---|---|---|---|---|---|---|---|
| | Males (includes MJ users) | | | | Males (excludes MJ users) | | | |
| platelet MAO-B concentration | 62.5 | 78.0 | 0.717 | 69.2 | 84.5 | 62.5 | 0.751 | 72.4 |
| % CDT | 61.2 | 86.0 | 0.766 | 60.8 | 63.5 | 90.0 | 0.773 | 65.9 |
| lnGGT | 56.6 | 79.4 | 0.738 | 64.7 | 46.8 | 100.0 | 0.769 | 71.6 |
| lnASAT | 65.1 | 80.0 | 0.808 | 69.2 | 58.1 | 92.5 | 0.789 | 69.6 |
| | Females (includes CD subjects) | | | | Females (excludes CD subjects) | | | |
| platelet MAO-B concentration | 56.8 | 69.1 | 0.663 | 53.5 | 55.0 | 69.4 | 0.648 | 51.7 |
| % CDT | 52.3 | 63.0 | 0.582 | 59.2 | 40.0 | 79.6 | 0.580 | 60.2 |
| lnGGT | 62.8 | 72.2 | 0.730 | 67.0 | 64.1 | 73.5 | 0.742 | 68.2 |
| lnASAT | 16.3 | 100.0 | 0.589 | 58.8 | 61.5 | 57.1 | 0.610 | 60.2 |

*MJ = marijuana use; CD = conduct disorder; Sens = % Sensitivity; Spec = % Specificity; Accuracy = (True positives + True negatives)/TOTAL × 100.

Performance of the markers to identify HHAU in females was poorer than that seen in males, primarily due to low diagnostic sensitivity. This has previously been reported for % CDT, GGT and ASAT (Sillanaukee and Olsson, *Clin Chem*, 47:681-685, 2001). Removing the female subjects with history of conduct disorder did not appreciably improve performance of these markers in detecting HHAU, perhaps due to the relatively small proportion of subjects exhibiting this condition (10/94=11%).

Analyses using combinations of markers were then used to assess sensitivity and specificity for identifying male and female hazardous/harmful drinkers. Several researchers have developed rules or algorithms for combining the quantitative results of multiple biochemical tests to increase diagnostic for HHAU (Sillanaukee and Olson, Clin Chem, 47:681-685, 2001; Chen et al., *Alcohol Alcohol*, 38:574-582, 2003), with the resulting combination providing higher accuracy than any test alone. Using linear discriminant analysis, the inventors assessed whether combinations of platelet MAO-B protein concentration with the other diagnostic markers, % CDT, GGT and ASAT, increased the diagnostic accuracy. In addition, these results were compared to combinations where platelet MAO-B protein concentration was not included. Men who had used marijuana in the previous 30 days and women who had a history of conduct disorder were excluded from these analyses. In both men and women, a number (but not all) of the discriminant functions that included one of the other markers in combination with platelet MAO-B protein concentration improved diagnostic performance as assessed by the AUC of the ROC curve or accuracy measures compared to MAO protein alone (Table 8). In males, the combination of platelet MAO-B protein concentration and lnGGT provided the highest accuracy, while platelet MAO-B protein concentration in combination with % CDT provided a larger AUC. The disparity in these two measures is due to the sacrifice of some sensitivity for greater specificity using % CDT vs. lnGGT. The combination of platelet MAO-B protein concentration, % CDT and lnGGT offered no additional improvement over the dual combinations. The addition of lnASAT to platelet MAO-B protein concentration alone or in combination with other markers offered no greater diagnostic utility. Discriminant functions utilizing combinations of % CDT, lnGGT and lnASAT attained higher specificities with modest losses of sensitivity, which is reflected in somewhat higher AUC compared to marker combinations containing platelet MAO-B protein concentration. The overall diagnostic accuracy, however, was not superior.

TABLE 8

Sensitivity, Specificity, Areas Under The ROC curve (AUC) And Accuracy For Combinations Of Markers

| Linear discriminant functions | Sens | Spec | AUC | Acc |
|---|---|---|---|---|
| Males (No MJ Use) | | | | |
| Platelet MAO-B concentration (MAO-P) | 84.5 | 62.5 | 0.751 | 72.4 |
| −0.673*MAO-P + 0.748*% CDT | 66.7 | 81.3 | 0.843 | 71.1 |
| 0.676*MAO-P − 0.665*lnGGT | 81.1 | 65.0 | 0.810 | 78.7 |
| 0.716*MAO-P − 0.642*lnASAT | 64.8 | 87.5 | 0.845 | 71.3 |
| −0.512*MAO-P + 0.554*% CDT + 0.555* lnGGT | 87.0 | 65.0 | 0.837 | 78.5 |
| −0.511*MAO-P + 0.575*% CDT + 0.606*lnGGT − 0.078*lnASAT | 66.0 | 90.9 | 0.827 | 78.5 |
| 0.659*% CDT + 0.736*ln (GGT) | 70.9 | 96.9 | 0.884 | 78.2 |
| 0.699*% CDT + 0.816*ln (GGT) − 0.126*lnASAT | 69.1 | 96.9 | 0.891 | 78.2 |
| Females (No CD) | | | | |
| Platelet MAO-B concentration (MAO-P) | 55.0 | 69.4 | 0.648 | 51.7 |
| 0.747*MAO-P − 0.724*% CDT | 77.5 | 60.4 | 0.728 | 62.5 |
| −0.536*MAO-P + 0.814*lnGGT | 87.2 | 55.1 | 0.792 | 72.7 |

TABLE 8-continued

Sensitivity, Specificity, Areas Under The ROC curve
(AUC) And Accuracy For Combinations Of Markers

| Linear discriminant functions | Sens | Spec | AUC | Acc |
|---|---|---|---|---|
| 0.782*MAO-P − 0.515*lnASAT | 100.0 | 26.5 | 0.671 | 62.5 |
| −0.516*MAO-P + 0.485*% CDT + 0.673*lnGGT | 66.7 | 83.3 | 0.820 | 72.4 |
| 0.719*MAO-P − 0.510*% CDT + 0.475*lnGGT + 0.365*lnASAT | 71.8 | 41.7 | 0.535 | 72.4 |
| 0.517*% CDT + 0.826*lnGGT | 74.4 | 72.9 | 0.773 | 72.4 |
| 0.544*% CDT + 0.912*lnGGT − 0.179*lnASAT | 74.4 | 70.8 | 0.774 | 71.3 |

Linear discriminant analysis (Johnson and Wichern, *Prentice-Hall*, 1992) was used to generate discriminant functions based on linear combinations of MAO-B protein and traditional markers for identification of high alcohol intake. Subjects with contributing and/or confounding variables, identified by logistic regression analysis, were excluded from the discriminant analysis. Linear discriminant analysis of marker combinations in females paralleled those seen in males with the combination of platelet MAO-B protein concentration and lnGGT providing the greatest accuracy (72.7%) for detecting HHAU, although the specificity was only moderate (55.1%) in the females. The discriminant function that also included % CDT produced an improved specificity (83.3%), and a higher AUC, with no appreciable change in accuracy. Again, the inclusion of lnASAT in the discriminant functions had no impact or reduced diagnostic performance. Discriminant functions utilizing combinations of % CDT, lnGGT and lNASAT did not outperform those utilizing platelet MAO-B protein concentration.

Example 9

Figure 8:
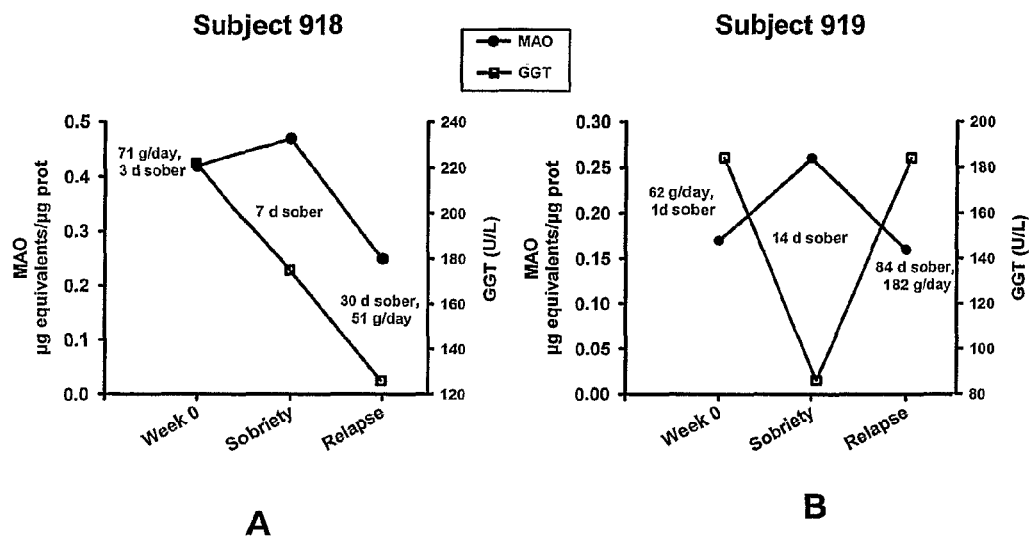
FIG. 8 provides graphs showing the changes in platelet MAO-B protein concentration and GGT levels in two subjects (subject 918 in panel A and subject 919 in panel B) during treatment for alcohol abuse. "Week 0" indicates the initial levels of platelet MAO-B protein and GGT concentrations obtained from blood samples taken within two days of hospitalization. Alcohol intake (average daily grams of ethanol intake during the previous 30 days) and the number of reported days sober immediately before hospitalization are noted alongside the time points on the graph. "Sobriety" indicates the time point at which the levels of platelet MAO-B protein were measured after the indicated number of days of hospitalization. "Relapse" indicates the time point at which the levels of platelet MAO-B protein were measured when the subject began drinking again. The average daily grams of ethanol intake during the two weeks following relapse is noted alongside the "relapse" value for MAO and GGT on the graph. The two panels present the data in fig equivalents of platelet MAO-B per µg total protein loaded on the gel, and the GGT levels are reported as units/liter (U/L).

Measurement of Mao-B Protein Content and GGT Activity in Two Subjects During Treatment of Alcohol Abuse As shown in FIG. 8, the MAO protein levels in subject 919 are low at the time of initial hospitalization (within 1-3 days) of beginning abstinence. The MAO protein levels rise after 14 days of sobriety to "normal" levels for this subject. However, when subject 919 relapses and is drinking 182 g alcohol/day after 84 days of being sober, the MAO protein levels again drop to levels seen prior to the abstinence period. The commonly used marker for alcohol intake, GGT, mirrors the pattern seen with MAO protein in this subject. Similarly, with 3-5 days of sobriety prior to giving a blood sample in the hospital, the MAO protein level in platelets of subject 918 are lower than when the subject has been sober for 10 days (3 days prior to hospitalization and 7 days in the hospital). The MAO protein levels drop significantly when this subject relapses after 30 days of sobriety and starts drinking 51 g alcohol/day. Interestingly, the commonly used marker, GGT, does not "sense" this relapse and continues on its downward trajectory. This data indicates the superiority of MAO protein levels in sensing relapse as compared to the commonly used marker, GGT.

Example 10

Use of Platelet P110 Protein to Standardize Platelet MAO-B Protein Levels (MAO-B/p110 Ratio)

Figure 6:
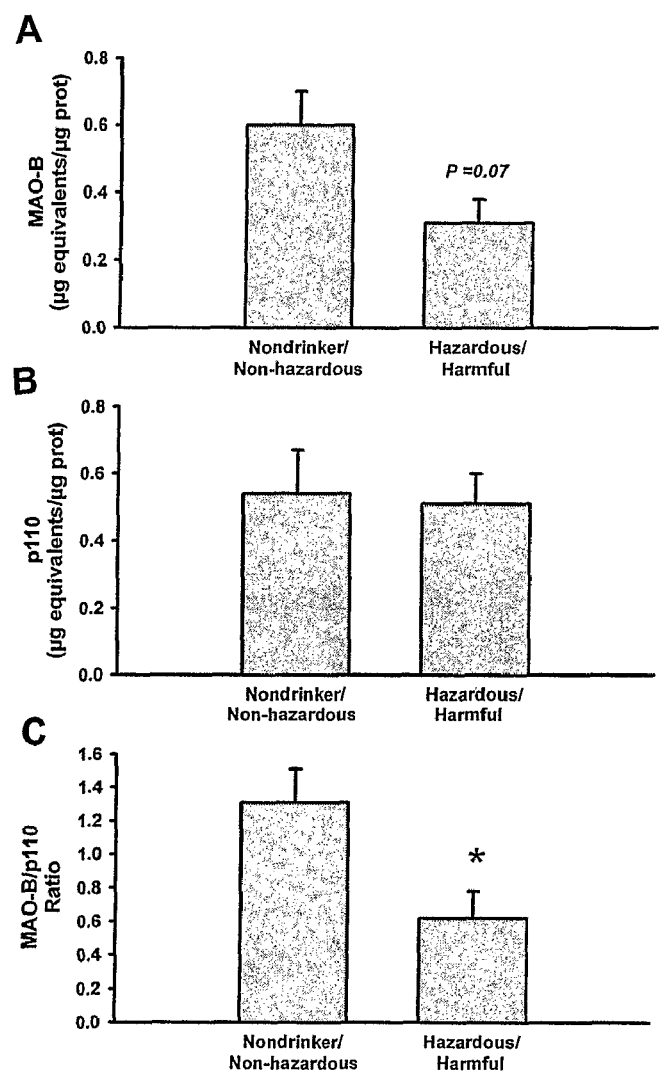
FIG. 6 provides a comparison of MAO-B protein concentrations (panel A), p110 protein concentrations (panel B), and MAO-B/p110 ratios (panel C) in male subjects with non-hazardous ethanol intake (nondrinker/non-hazardous) and hazardous/harmful ethanol intake in the previous 30 days. Data are shown as an average±standard error of the mean of 14 and 7 values, respectively, with an asterisk denoting P<0.05 by Student's t-test.
Figure 7:
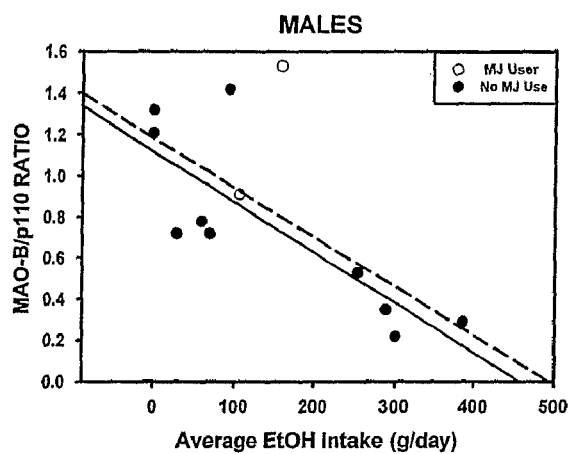
FIG. 7 depicts correlations between average daily ethanol intake expressed in g/day and platelet MAO-B protein concentration expressed as the MAO-B/p100 ratio. MAO-B/p110 ratios were significantly correlated (P<0.02; dashed line) with the average daily ethanol intake in male subjects (N=12). Exclusion of the two marijuana users from the analysis improves the correlation (P<0.005; solid line).
Figure 11:
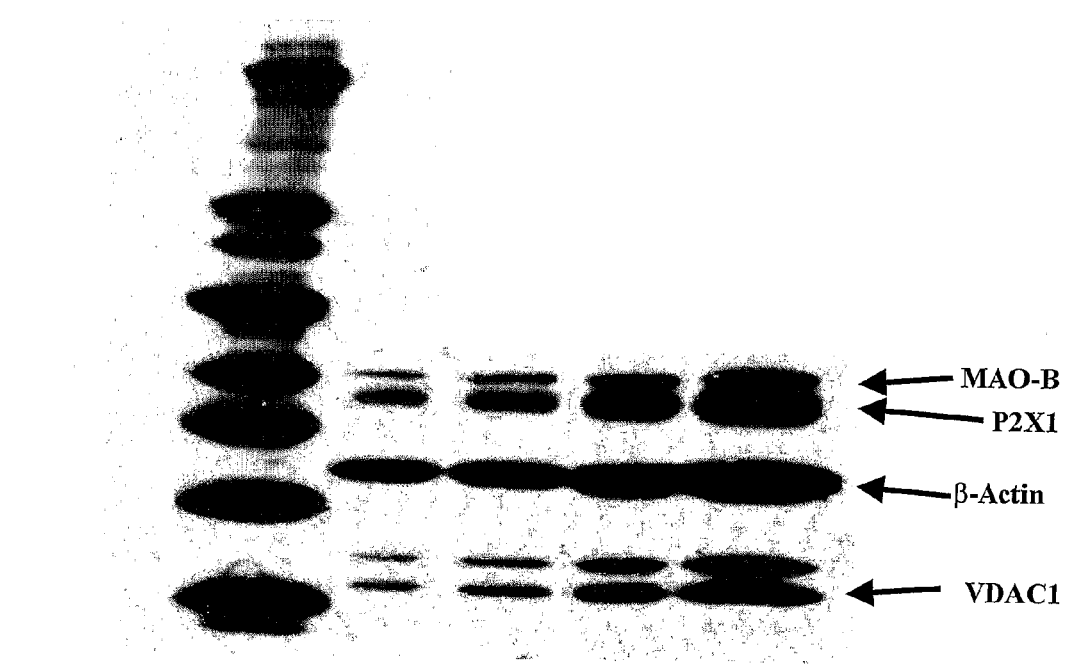
FIG. 11 depicts an immunoblot of standard platelet membranes illustrating the use of internal standard markers for platelet membranes (P2X1, purinergic receptor), total protein (β-actin, structural protein) and mitochondrial membranes (VDAC1, voltage-dependent anion channel). Standard platelet membranes were separated on a 8-16% SDS-PAGE gel and transferred to nitrocellulose membranes. Blots were incubated in 1:1,000 dilutions of anti-MAO-B (Lohocla), 1:3,000 dilution of anti-P2X1 (Chemicon International), 1:50,000 dilution of β-actin (Rockland Immunochemicals) and 1:3,000 dilution of VDAC (Abcam) antibodies, followed by incubation in goat anti-rabbit HRP conjugated secondary antibody. Immunoreactive bands were detected by chemiluminescence. The left lane was loaded with MagicMark XP molecular weight standards (InVitrogen).

The immunological measure of platelet MAO-B protein concentration can be influenced by the quality of the platelet membrane preparation. High levels of non-platelet contaminating proteins from plasma and other blood cells can reduce the apparent MAO-B protein concentration when concentration is expressed per µg of total protein. For this reason, an immunological measure of the level of the mitochondrial-specific protein, p110, was added. p110 was chosen given that the levels of this protein are not significantly affected by ethanol consumption levels (FIG. 4A and FIG. 6A). Measurements of both MAO-B and p110 in the same platelet preparations provide a means of expressing MAO-B protein concentrations per unit of another "internal standard" mitochondrial protein (i.e., MAO-B/p110 ratio). Other platelet proteins that can be used in a way similar to p110 include but are not limited to P2X1, β-actin and VDAC1. Other suitable "internal standard proteins" include those platelet proteins that do not change as a consequence of alcohol consumption. FIG. 11 provides an immunoblot illustrating the use of P2X1, β-actin and VDAC1 as "internal standard proteins." FIG. 6B depicts the correlation between the average daily ethanol intake during the previous 30 days and the MAO-B/p110 ratio in 12 male subjects. Linear regression analysis yielded a significant relationship between the MAO-B/p110 ratios with all subjects included (R=0.94, P<0.02). If subjects who had smoked marijuana in the previous 30 days were excluded from the analysis, the correlation improved (R=0.96, P<0.005). For instance, when using standardized antibodies for MAO-B protein and p110 control protein, a threshold value of 0.6 distinguishes hazardous or harmful alcohol using (HHAU) subjects, from subjects that consume little to no alcohol. The HHAU subjects exhibit ratios less than 0.6, while the non-HHAU subjects exhibit ratios of greater than 0.6.

Further evidence of the benefit of the use of MAO-B/p110 ratio over platelet MAO-B protein concentration alone is demonstrated in FIG. 6A, where in male subjects, the MAO-B/p110 ratio more clearly distinguishes subjects exhibiting HHAU, than does measures of only the platelet MAO-B protein concentration. As previously stated, p110 protein concentrations show no correlation to (are unaffected by) ethanol drinking levels.

Example 11

Identification of MAO-B Aptamers

This example describes the use of in vitro selection and amplification techniques to identify nucleic acid ligands (aptamer) with high affinity and specificity for the MAO-B protein (See, Turek and Gold, *Science*, 249:505-510, 1990; and Ellington and Szostak, *Nature*, 346:818-822). A SELEX-type process (Systematic Evolution of Ligands by EXponential enrichment) is employed for screening a large combinatorial library of oligonucleotides library (See, e.g., U.S. Pat. No. 5,270,163; and U.S. Pat. No. 5,475,096; and as reviewed in Jayasena, *Clinical Chemistry*, 45:1628-1650, 1999, all herein incorporated by reference in their entirety). These methods are also suitable for use in identifying aptamers for other platelet associated substance use (PASU) markers. Briefly, the basic elements of the SELEX process involve the following series of steps:

1) Preparing a candidate mixture of nucleic acids of differing sequence. The candidate mixture generally includes regions of fixed sequences (i.e., each of the members of the candidate mixture contains the same sequences in the same location) and regions of randomized sequences. The fixed sequence regions are selected either: a) to assist in the amplification steps described below; b) to facilitate mimicry of a sequence known to bind to the target; or c) to enhance the concentration of a given structural arrangement of the nucleic acids in the candidate mixture. The randomized sequences can be totally randomized (i.e., the probability of finding a base at any position being one in four) or only partially randomized (e.g., the probability of finding a base at any location can be selected at any level between 0 and 100 percent).

2) The candidate mixture is contacted with the selected target under conditions favorable for binding between the target and members of the candidate mixture. Under these circumstances, the interaction between the target and the nucleic acids of the candidate mixture can be considered as forming nucleic acid-target pairs between the target and the nucleic acids having the strongest affinity for the target.

3) The nucleic acids with the highest affinity for the target are partitioned from those nucleic acids with lesser affinity to the target. Because only a small number of sequences (and possibly only one molecule of nucleic acid) corresponding to the highest affinity nucleic acids exist in the candidate mixture, it is generally desirable to set the partitioning criteria so that a significant amount of the nucleic acids in the candidate mixture (approximately 5-50%) are retained during partitioning.

4) Those nucleic acids selected during partitioning as having the relatively higher affinity to the target are then amplified to create a new candidate mixture that is enriched in nucleic acids having a relatively higher affinity for the target.

5) By repeating the partitioning and amplifying steps above, the newly formed candidate mixture contains fewer and fewer unique sequences, and the average degree of affinity of the nucleic acids to the target will generally increase. Taken to its extreme, the SELEX process will yield a candidate mixture containing one or a small number of unique nucleic acids representing those nucleic acids from the original candidate mixture having the highest affinity to the target molecule.

In an exemplary embodiment, a recombinant human MAO-B fusion protein comprising an MAO-B sequence fused to an affinity tag (e.g., IgG, polyhistidine, flu epitope, etc.) is prepared. The purified MAO-B protein is immobilized on a suspendable solid support such as paramagnetic beads (Dynal, Lake Success, N.Y.). After washing the beads, affinity selections are performed by mixing the bead slurry with an RNA library, and incubating the mixture at 37° C. for 30 min. After washing, the beads (paramagnetic spheres/MAO-B/RNA) were then transferred to a new microfuge tube for subsequent reverse transcription. After removal of the beads, the reverse transcriptase solution is subjected to PCR amplification with an error-prone polymerase (e.g., Taq) and a primer pair whose sequence is shared by the members of the RNA library. In vitro transcription of the PCR amplified product is done followed by purification of the transcripts by gel electrophoresis after a brief DNase treatment to remove the template. This process is repeated multiple times (e.g., 3-6). Sequences of a multiple aptamer clones are obtained by standard cloning and sequencing methods. The binding affinity of a subset of aptamers is measuring using a nitrocellulose filter binding method. In some preferred embodiments, aptamers with high affinity and specificity for MAO-B are selected for use in diagnostic tests of heavy drinking.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in molecular biology, biochemistry, proteomics, medicine, psychiatry or related fields, are intended to be within the scope of the following claims.

We claim:

1. A method for monitoring alcohol consumption by a subject, comprising:
   a) obtaining a sample comprising platelets from the subject, wherein the platelets comprise a platelet associated substance use (PASU) marker protein and a platelet p110 protein;
   b) measuring the PASU marker protein content and the platelet p110 protein content of said sample; and
   c) comparing said PASU marker protein content to said platelet p110 protein content to obtain a ratio, wherein said ratio is inversely related to an average level of alcohol consumption by said subject within the previous fourteen days.

2. The method of claim 1, wherein said measuring is accomplished by use of an affinity-type method.

3. The method of claim 2, wherein said affinity-type method comprises antibody-based methods.

4. The method of claim 2, wherein said affinity type method comprises aptamer-based methods.

5. The method of claim 1, wherein said measuring is accomplished by use of a proteomics method.

6. The method of claim 5, wherein said proteomic methods comprise liquid chromatography and tandem mass spectrometry.

7. The method of claim 1, wherein said PASU marker protein is monoamine oxidase-B (MAO-B) protein.

8. The method of claim 7, wherein said ratio of MAO-B protein content to said platelet p110 protein content is significantly higher when said subject has abstained from drinking alcohol for at least 7 days, than when said subject has consistently consumed a hazardous or harmful amount of alcohol, wherein if said subject is male said hazardous amount of alcohol is on average greater than 40 g/day, and said harmful amount of alcohol is on average greater than 80 g/day, and wherein if said subject is female said hazardous amount of alcohol is on average greater than 20 g/day, and said harmful amount of alcohol is on average greater than 60 g/day.

9. The method of claim 7, wherein when said ratio of MAO-B protein content to said platelet p110 protein content is less than a threshold value, said method further comprises identifying said subject as having consumed a hazardous or harmful amount of alcohol within the previous fourteen days, wherein if said subject is male said hazardous amount of alcohol is on average greater than 40 g/day, and said harmful amount of alcohol is on average greater than 80 g/day, and wherein if said subject is female said hazardous amount of alcohol is on average greater than 20 g/day, and said harmful amount of alcohol is on average greater than 60 g/day.

10. The method of claim 7, wherein when said ratio of MAO-B protein content to said platelet p110 protein content is greater than a threshold value, said method further comprises identifying said subject as having abstained from or consumed a non-hazardous amount of alcohol within the previous fourteen days, wherein if said subject is male said non-hazardous amount of alcohol is on average less than 40 g/day, and wherein if said subject is female said non-hazardous amount of alcohol is on average less than 20 g/day.

11. The method of claim 7, further comprising measuring a second marker of alcohol consumption in a sample from said subject, wherein said PASU marker protein comprises a first marker of alcohol consumption.

12. The method of claim 11, wherein said second marker is in a second sample comprising urine obtained from said subject.

13. The method of claim 11, wherein said second marker of alcohol consumption comprises one or more of percent carbohydrate-deficient transferrin (% CDT), γ-glutamyltransferase (GGT), alanine/serine aminotransferase (ASAT), and ethyl glucuronide (EtG).

14. The method of claim 1, further comprising step d) correlating said ratio with said subject's risk for developing an alcohol-related health problem, wherein said alcohol-related health problem comprises one or more of dementia, stroke, peripheral neuropathy, esophageal disease, gastritis, peptic ulcer, alcoholic hepatitis, liver cirrhosis, hypertension, left ventricular hypertrophy/cardiomyopathy, arrhythmia and heart attack, and wherein: (i) when said ratio is less than a threshold value, said method comprises identifying said subject as having an increased risk for developing said alcohol-related health problem, or (ii) when said ratio is greater than said threshold value, said method comprises identifying said subject as not having increased risk for developing said alcohol-related health problem.

15. The method of claim 1, wherein said PASU marker protein is selected from the group consisting of CGI-51, glycine aminotransferase (GATM), oxoglutarate dehydrogenase (OGDH), and peripheral benzodiazepine receptor (PBDR).

* * * * *

SEQUENCE LISTING

```
<160> NUMBER OF SEQ ID NOS: 27

<210> SEQ ID NO 1
<211> LENGTH: 520
<212> TYPE: PRT
<213> ORGANISM: Homo sapiens

<400> SEQUENCE: 1

Met Ser Asn Lys Cys Asp Val Val Val Gly Gly Gly Ile Ser Gly
 1               5                  10                  15

Met Ala Ala Lys Leu Leu His Asp Ser Gly Leu Asn Val Val Val
                20                  25                  30

Leu Glu Ala Arg Asp Arg Val Gly Gly Arg Thr Tyr Thr Leu Arg Asn
                35                  40                  45

Gln Lys Val Lys Tyr Val Asp Leu Gly Gly Ser Tyr Val Gly Pro Thr
        50                  55                  60

Gln Asn Arg Ile Leu Arg Leu Ala Lys Glu Leu Gly Leu Glu Thr Tyr
```

```
                65                  70                  75                  80
            Lys Val Asn Glu Val Glu Arg Leu Ile His His Val Lys Gly Lys Ser
                            85                  90                  95
            Tyr Pro Phe Arg Gly Pro Phe Pro Val Trp Asn Pro Ile Thr Tyr
                        100                 105                 110
            Leu Asp His Asn Asn Phe Trp Arg Thr Met Asp Asp Met Gly Arg Glu
                        115                 120                 125
            Ile Pro Ser Asp Ala Pro Trp Lys Ala Pro Leu Ala Glu Glu Trp Asp
                    130                 135                 140
            Asn Met Thr Met Lys Glu Leu Leu Asp Lys Leu Cys Trp Thr Glu Ser
            145                 150                 155                 160
            Ala Lys Gln Leu Ala Thr Leu Phe Val Asn Leu Cys Val Thr Ala Glu
                            165                 170                 175
            Thr His Glu Val Ser Ala Leu Trp Phe Leu Trp Tyr Val Lys Gln Cys
                        180                 185                 190
            Gly Gly Thr Thr Arg Ile Ile Ser Thr Thr Asn Gly Gly Gln Glu Arg
                        195                 200                 205
            Lys Phe Val Gly Gly Ser Gly Gln Val Ser Glu Arg Ile Met Asp Leu
                    210                 215                 220
            Leu Gly Asp Arg Val Lys Leu Glu Arg Pro Val Ile Tyr Ile Asp Gln
            225                 230                 235                 240
            Thr Arg Glu Asn Val Leu Val Glu Thr Leu Asn His Glu Met Tyr Glu
                            245                 250                 255
            Ala Lys Tyr Val Ile Ser Ala Ile Pro Pro Thr Leu Gly Met Lys Ile
                        260                 265                 270
            His Phe Asn Pro Pro Leu Pro Met Met Arg Asn Gln Met Ile Thr Arg
                        275                 280                 285
            Val Pro Leu Gly Ser Val Ile Lys Cys Ile Val Tyr Tyr Lys Glu Pro
                    290                 295                 300
            Phe Trp Arg Lys Lys Asp Tyr Cys Gly Thr Met Ile Ile Asp Gly Glu
            305                 310                 315                 320
            Glu Ala Pro Val Ala Tyr Thr Leu Asp Asp Thr Lys Pro Glu Gly Asn
                            325                 330                 335
            Tyr Ala Ala Ile Met Gly Phe Ile Leu Ala His Lys Ala Arg Lys Leu
                        340                 345                 350
            Ala Arg Leu Thr Lys Glu Glu Arg Leu Lys Lys Leu Cys Glu Leu Tyr
                        355                 360                 365
            Ala Lys Val Leu Gly Ser Leu Glu Ala Leu Glu Pro Val His Tyr Glu
                    370                 375                 380
            Glu Lys Asn Trp Cys Glu Glu Gln Tyr Ser Gly Gly Cys Tyr Thr Thr
            385                 390                 395                 400
            Tyr Phe Pro Pro Gly Ile Leu Thr Gln Tyr Gly Arg Val Leu Arg Gln
                            405                 410                 415
            Pro Val Asp Arg Ile Tyr Phe Ala Gly Thr Glu Thr Ala Thr His Trp
                        420                 425                 430
            Ser Gly Tyr Met Glu Gly Ala Val Glu Ala Gly Glu Arg Ala Ala Arg
                        435                 440                 445
            Glu Ile Leu His Ala Met Gly Lys Ile Pro Glu Asp Glu Ile Trp Gln
                    450                 455                 460
            Ser Glu Pro Glu Ser Val Asp Val Pro Ala Gln Pro Ile Thr Thr Thr
            465                 470                 475                 480
            Phe Leu Glu Arg His Leu Pro Ser Val Pro Gly Leu Leu Arg Leu Ile
                            485                 490                 495
```

```
Gly Leu Thr Thr Ile Phe Ser Ala Thr Ala Leu Gly Phe Leu Ala His
                500                 505                 510
Lys Arg Gly Leu Leu Val Arg Val
            515                 520
```

<210> SEQ ID NO 2
<211> LENGTH: 19
<212> TYPE: PRT
<213> ORGANISM: Homo sapiens

<400> SEQUENCE: 2

```
Gly Lys Ser Tyr Pro Phe Arg Gly Pro Phe Pro Pro Val Trp Asn Pro
 1                5                  10                  15
Ile Thr Tyr
```

<210> SEQ ID NO 3
<211> LENGTH: 17
<212> TYPE: PRT
<213> ORGANISM: Homo sapiens

<400> SEQUENCE: 3

```
Ser Tyr Pro Phe Arg Gly Pro Phe Pro Pro Val Trp Asn Pro Ile Thr
 1                5                  10                  15
Tyr
```

<210> SEQ ID NO 4
<211> LENGTH: 18
<212> TYPE: PRT
<213> ORGANISM: Homo sapiens

<400> SEQUENCE: 4

```
Ser Tyr Pro Phe Arg Gly Pro Phe Pro Pro Val Trp Asn Pro Ile Thr
 1                5                  10                  15
Tyr Leu
```

<210> SEQ ID NO 5
<211> LENGTH: 13
<212> TYPE: PRT
<213> ORGANISM: Homo sapiens

<400> SEQUENCE: 5

```
Arg Gly Pro Phe Pro Pro Val Trp Asn Pro Ile Thr Tyr
 1                5                  10
```

<210> SEQ ID NO 6
<211> LENGTH: 14
<212> TYPE: PRT
<213> ORGANISM: Homo sapiens

<400> SEQUENCE: 6

```
Arg Gly Pro Phe Pro Pro Val Trp Asn Pro Ile Thr Tyr Leu
 1                5                  10
```

<210> SEQ ID NO 7
<211> LENGTH: 17
<212> TYPE: PRT
<213> ORGANISM: Homo sapiens

<400> SEQUENCE: 7

```
Asp Asp Met Gly Arg Glu Ile Pro Ser Asp Ala Pro Trp Lys Ala Pro
 1                5                  10                  15
Leu
```

<210> SEQ ID NO 8
<211> LENGTH: 19
<212> TYPE: PRT
<213> ORGANISM: Homo sapiens

<400> SEQUENCE: 8

Asp Asp Met Gly Arg Glu Ile Pro Ser Asp Ala Pro Trp Lys Ala Pro
1               5                   10                  15

Leu Ala Glu

<210> SEQ ID NO 9
<211> LENGTH: 9
<212> TYPE: PRT
<213> ORGANISM: Homo sapiens

<400> SEQUENCE: 9

Ile His Phe Asn Pro Pro Leu Pro Met
1               5

<210> SEQ ID NO 10
<211> LENGTH: 10
<212> TYPE: PRT
<213> ORGANISM: Homo sapiens

<400> SEQUENCE: 10

Ile His Phe Asn Pro Pro Leu Pro Met Met
1               5                   10

<210> SEQ ID NO 11
<211> LENGTH: 10
<212> TYPE: PRT
<213> ORGANISM: Homo sapiens

<400> SEQUENCE: 11

Arg Gln Pro Val Asp Arg Ile Tyr Phe Ala
1               5                   10

<210> SEQ ID NO 12
<211> LENGTH: 12
<212> TYPE: PRT
<213> ORGANISM: Homo sapiens

<400> SEQUENCE: 12

Ser Val Asp Val Pro Ala Gln Pro Ile Thr Thr Thr
1               5                   10

<210> SEQ ID NO 13
<211> LENGTH: 14
<212> TYPE: PRT
<213> ORGANISM: Homo sapiens

<400> SEQUENCE: 13

Thr Phe Leu Glu Arg His Leu Pro Ser Val Pro Gly Leu Leu
1               5                   10

<210> SEQ ID NO 14
<211> LENGTH: 13
<212> TYPE: PRT
<213> ORGANISM: Homo sapiens

<400> SEQUENCE: 14

Phe Leu Glu Arg His Leu Pro Ser Val Pro Gly Leu Leu
1               5                   10

```
<210> SEQ ID NO 15
<211> LENGTH: 12
<212> TYPE: PRT
<213> ORGANISM: Homo sapiens

<400> SEQUENCE: 15

Leu Glu Arg His Leu Pro Ser Val Pro Gly Leu Leu
 1               5                  10

<210> SEQ ID NO 16
<211> LENGTH: 10
<212> TYPE: PRT
<213> ORGANISM: Homo sapiens

<400> SEQUENCE: 16

Arg His Leu Pro Ser Val Pro Gly Leu Leu
 1               5                  10

<210> SEQ ID NO 17
<211> LENGTH: 20
<212> TYPE: PRT
<213> ORGANISM: Homo sapiens

<400> SEQUENCE: 17

Leu Leu Arg Leu Ile Gly Leu Thr Thr Ile Phe Ser Ala Thr Ala Leu
 1               5                  10                  15

Gly Phe Leu Ala
            20

<210> SEQ ID NO 18
<211> LENGTH: 468
<212> TYPE: PRT
<213> ORGANISM: Homo sapiens

<400> SEQUENCE: 18

Met Gly Thr Val His Ala Arg Ser Leu Glu Pro Leu Pro Ser Ser Gly
 1               5                  10                  15

Pro Asp Phe Gly Gly Leu Gly Glu Glu Ala Glu Phe Val Glu Val Glu
                20                  25                  30

Pro Glu Ala Lys Gln Glu Ile Leu Glu Asn Lys Asp Val Val Gln
            35                  40                  45

His Val His Phe Asp Gly Leu Gly Arg Thr Lys Asp Asp Ile Ile Ile
 50                  55                  60

Cys Glu Ile Gly Asp Val Phe Lys Ala Lys Asn Leu Ile Glu Val Met
65                  70                  75                  80

Arg Lys Ser His Glu Ala Arg Glu Lys Leu Leu Arg Leu Gly Ile Phe
                85                  90                  95

Arg Gln Val Asp Val Leu Ile Asp Thr Cys Gln Gly Asp Asp Ala Leu
            100                 105                 110

Pro Asn Gly Leu Asp Val Thr Phe Glu Val Thr Glu Leu Arg Arg Leu
        115                 120                 125

Thr Gly Ser Tyr Asn Thr Met Val Gly Asn Asn Glu Gly Ser Met Val
    130                 135                 140

Leu Gly Leu Lys Leu Pro Asn Leu Leu Gly Arg Ala Glu Lys Val Thr
145                 150                 155                 160

Phe Gln Phe Ser Tyr Gly Thr Lys Glu Thr Ser Tyr Gly Leu Ser Phe
                165                 170                 175

Phe Lys Pro Arg Pro Gly Asn Phe Glu Arg Asn Phe Ser Val Asn Leu
            180                 185                 190

Tyr Lys Val Thr Gly Gln Phe Pro Trp Ser Ser Leu Arg Glu Thr Asp
```

```
                195                 200                 205
Arg Gly Met Ser Ala Glu Tyr Ser Phe Pro Ile Trp Lys Thr Ser His
    210                 215                 220

Thr Val Lys Trp Glu Gly Val Trp Arg Glu Leu Gly Cys Leu Ser Arg
225                 230                 235                 240

Thr Ala Ser Phe Ala Val Arg Lys Glu Ser Gly His Ser Leu Lys Ser
                245                 250                 255

Ser Leu Ser His Ala Met Val Ile Asp Ser Arg Asn Ser Ser Ile Leu
                260                 265                 270

Pro Arg Arg Gly Ala Leu Leu Lys Val Asn Gln Glu Leu Ala Gly Tyr
                275                 280                 285

Thr Gly Gly Asp Val Ser Phe Lys Glu Asp Phe Glu Leu Gln Leu Asn
    290                 295                 300

Lys Gln Leu Ile Phe Asp Ser Val Phe Ser Ala Ser Phe Trp Gly Gly
305                 310                 315                 320

Met Leu Val Pro Ile Gly Asp Lys Pro Ser Ser Ile Ala Asp Arg Phe
                325                 330                 335

Tyr Leu Gly Gly Pro Thr Ser Val Arg Gly Phe Ser Met His Ser Ile
                340                 345                 350

Gly Pro Gln Ser Glu Gly Asp Tyr Leu Gly Gly Glu Ala Tyr Trp Ala
                355                 360                 365

Gly Gly Leu His Leu Tyr Thr Pro Leu Pro Phe Arg Pro Gly Gln Gly
    370                 375                 380

Gly Phe Gly Glu Leu Phe Arg Thr His Phe Leu Asn Ala Gly Asn
385                 390                 395                 400

Leu Cys Asn Leu Asn Tyr Gly Glu Gly Pro Lys Ala His Ile Arg Lys
                405                 410                 415

Leu Ala Glu Cys Ile Arg Trp Ser Tyr Gly Ala Gly Ile Val Leu Arg
                420                 425                 430

Leu Gly Asn Ile Ala Arg Leu Glu Leu Asn Tyr Cys Val Pro Met Gly
                435                 440                 445

Val Gln Thr Gly Asp Arg Ile Cys Asp Gly Val Gln Phe Gly Ala Gly
    450                 455                 460

Ile Arg Phe Leu
465

<210> SEQ ID NO 19
<211> LENGTH: 423
<212> TYPE: PRT
<213> ORGANISM: Homo sapiens

<400> SEQUENCE: 19

Met Leu Arg Val Arg Cys Leu Arg Gly Gly Ser Arg Gly Ala Glu Ala
1               5                   10                  15

Val His Tyr Ile Gly Ser Arg Leu Gly Arg Thr Leu Thr Gly Trp Val
                20                  25                  30

Gln Arg Thr Phe Gln Ser Thr Gln Ala Ala Thr Ala Ser Ser Arg Asn
            35                  40                  45

Ser Cys Ala Ala Asp Asp Lys Ala Thr Glu Pro Leu Pro Lys Asp Cys
        50                  55                  60

Pro Val Ser Ser Tyr Asn Glu Trp Asp Pro Leu Glu Glu Val Ile Val
65                  70                  75                  80

Gly Arg Ala Glu Asn Ala Cys Val Pro Pro Phe Thr Ile Glu Val Lys
                85                  90                  95

Ala Asn Thr Tyr Glu Lys Tyr Trp Pro Phe Tyr Gln Lys Gln Gly Gly
```

```
                    100                 105                 110
His Tyr Phe Pro Lys Asp His Leu Lys Lys Ala Val Ala Glu Ile Glu
            115                 120                 125
Glu Met Cys Asn Ile Leu Lys Thr Glu Gly Val Thr Val Arg Arg Pro
130                 135                 140
Asp Pro Ile Asp Trp Ser Leu Lys Tyr Lys Thr Pro Asp Phe Glu Ser
145                 150                 155                 160
Thr Gly Leu Tyr Ser Ala Met Pro Arg Asp Ile Leu Ile Val Val Gly
            165                 170                 175
Asn Glu Ile Ile Glu Ala Pro Met Ala Trp Arg Ser Arg Phe Phe Glu
            180                 185                 190
Tyr Arg Ala Tyr Arg Ser Ile Ile Lys Asp Tyr Phe His Arg Gly Ala
            195                 200                 205
Lys Trp Thr Thr Ala Pro Lys Pro Thr Met Ala Asp Glu Leu Tyr Asn
            210                 215                 220
Gln Asp Tyr Pro Ile His Ser Val Glu Asp Arg His Lys Leu Ala Ala
225                 230                 235                 240
Gln Gly Lys Phe Val Thr Thr Glu Phe Glu Pro Cys Phe Asp Ala Ala
            245                 250                 255
Asp Phe Ile Arg Ala Gly Arg Asp Ile Phe Ala Gln Arg Ser Gln Val
            260                 265                 270
Thr Asn Tyr Leu Gly Ile Glu Trp Met Arg Arg His Leu Ala Pro Asp
            275                 280                 285
Tyr Arg Val His Ile Ile Ser Phe Lys Asp Pro Asn Pro Met His Ile
            290                 295                 300
Asp Ala Thr Phe Asn Ile Ile Gly Pro Gly Ile Val Leu Ser Asn Pro
305                 310                 315                 320
Asp Arg Pro Cys His Gln Ile Asp Leu Phe Lys Lys Ala Gly Trp Thr
            325                 330                 335
Ile Ile Thr Pro Pro Thr Pro Ile Pro Asp His Pro Leu Trp
            340                 345                 350
Met Ser Ser Lys Trp Leu Ser Met Asn Val Leu Met Leu Asp Glu Lys
            355                 360                 365
Arg Val Met Val Asp Ala Asn Glu Val Pro Ile Gln Lys Met Phe Glu
            370                 375                 380
Lys Leu Gly Ile Thr Thr Ile Lys Val Asn Ile Arg Asn Ala Asn Ser
385                 390                 395                 400
Leu Gly Gly Gly Phe His Cys Trp Thr Cys Asp Val Arg Arg Arg Gly
            405                 410                 415
Thr Leu Gln Ser Tyr Leu Asp
            420

<210> SEQ ID NO 20
<211> LENGTH: 1022
<212> TYPE: PRT
<213> ORGANISM: Homo sapiens

<400> SEQUENCE: 20

Met Phe His Leu Arg Thr Cys Ala Ala Lys Leu Arg Pro Leu Thr Ala
1               5                   10                  15
Ser Gln Thr Val Lys Thr Phe Ser Gln Asn Arg Pro Ala Ala Ala Arg
            20                  25                  30
Thr Phe Gln Gln Ile Arg Cys Tyr Ser Ala Pro Val Ala Ala Glu Pro
        35                  40                  45
Phe Leu Ser Gly Thr Ser Ser Asn Tyr Val Glu Glu Met Tyr Cys Ala
```

```
            50                   55                  60
Trp Leu Glu Asn Pro Lys Ser Val His Lys Ser Trp Asp Ile Phe Phe
65                  70                  75                  80

Arg Asn Thr Asn Ala Gly Ala Pro Gly Thr Ala Tyr Gln Ser Pro
                85                  90                  95

Leu Pro Leu Ser Arg Gly Ser Leu Ala Ala Val Ala His Ala Gln Ser
                100                 105                 110

Leu Val Glu Ala Gln Pro Asn Val Asp Lys Leu Val Glu Asp His Leu
                115                 120                 125

Ala Val Gln Ser Leu Arg Ala Tyr Gln Ile Arg Gly His His Val Ala
                130                 135                 140

Gln Leu Asp Pro Leu Gly Ile Leu Asp Ala Asp Leu Asp Ser Ser Val
145                 150                 155                 160

Pro Ala Asp Ile Ile Ser Ser Thr Asp Lys Leu Gly Phe Tyr Gly Leu
                    165                 170                 175

Asp Glu Ser Asp Leu Asp Lys Val Phe His Leu Pro Thr Thr Thr Phe
                180                 185                 190

Ile Gly Gly Gln Glu Ser Ala Leu Pro Leu Arg Glu Ile Ile Arg Arg
                195                 200                 205

Leu Glu Met Ala Tyr Cys Gln His Ile Gly Val Glu Phe Met Phe Ile
210                 215                 220

Asn Asp Leu Glu Gln Cys Gln Trp Ile Arg Gln Lys Phe Glu Thr Pro
225                 230                 235                 240

Gly Ile Met Gln Phe Thr Asn Glu Glu Lys Arg Thr Leu Leu Ala Arg
                    245                 250                 255

Leu Val Arg Ser Thr Arg Phe Glu Glu Phe Leu Gln Arg Lys Trp Ser
                260                 265                 270

Ser Glu Lys Arg Phe Gly Leu Glu Gly Cys Glu Val Leu Ile Pro Ala
                275                 280                 285

Leu Lys Thr Ile Ile Asp Lys Ser Ser Glu Asn Gly Val Asp Tyr Val
                290                 295                 300

Ile Met Gly Met Pro His Arg Gly Arg Leu Asn Val Leu Ala Asn Val
305                 310                 315                 320

Ile Arg Lys Glu Leu Glu Gln Ile Phe Cys Gln Phe Asp Ser Lys Leu
                    325                 330                 335

Glu Ala Ala Asp Glu Gly Ser Gly Asp Val Lys Tyr His Leu Gly Met
                340                 345                 350

Tyr His Arg Arg Ile Asn Arg Val Thr Asp Arg Asn Ile Thr Leu Ser
                355                 360                 365

Leu Val Ala Asn Pro Ser His Leu Glu Ala Ala Asp Pro Val Val Met
370                 375                 380

Gly Lys Thr Lys Ala Glu Gln Phe Tyr Cys Gly Asp Thr Glu Gly Lys
385                 390                 395                 400

Lys Val Met Ser Ile Leu Leu His Gly Asp Ala Ala Phe Ala Gly Gln
                    405                 410                 415

Gly Ile Val Tyr Glu Thr Phe His Leu Ser Asp Leu Pro Ser Tyr Thr
                420                 425                 430

Thr His Gly Thr Val His Val Val Asn Asn Gln Ile Gly Phe Thr
                435                 440                 445

Thr Asp Pro Arg Met Ala Arg Ser Ser Pro Tyr Pro Thr Asp Val Ala
    450                 455                 460

Arg Val Val Asn Ala Pro Ile Phe His Val Asn Ser Asp Asp Pro Glu
465                 470                 475                 480
```

```
-continued

Ala Val Met Tyr Val Cys Lys Val Ala Ala Glu Trp Arg Ser Thr Phe
                485                 490                 495

His Lys Asp Val Val Asp Leu Val Cys Tyr Arg Arg Asn Gly His
            500                 505                 510

Asn Glu Met Asp Glu Pro Met Phe Thr Gln Pro Leu Met Tyr Lys Gln
            515                 520                 525

Ile Arg Lys Gln Lys Pro Val Leu Gln Lys Tyr Ala Glu Leu Leu Val
        530                 535                 540

Ser Gln Gly Val Val Asn Gln Pro Glu Tyr Glu Glu Ile Ser Lys
545                 550                 555                 560

Tyr Asp Lys Ile Cys Glu Glu Ala Phe Ala Arg Ser Lys Asp Glu Lys
                565                 570                 575

Ile Leu His Ile Lys His Trp Leu Asp Ser Pro Trp Pro Gly Phe Phe
            580                 585                 590

Thr Leu Asp Gly Gln Pro Arg Ser Met Ser Cys Pro Ser Thr Gly Leu
            595                 600                 605

Thr Glu Asp Ile Leu Thr His Ile Gly Asn Val Ala Ser Ser Val Pro
        610                 615                 620

Val Glu Asn Phe Thr Ile His Gly Gly Leu Ser Arg Ile Leu Lys Thr
625                 630                 635                 640

Arg Gly Glu Met Val Lys Asn Arg Thr Val Asp Trp Ala Leu Ala Glu
                645                 650                 655

Tyr Met Ala Phe Gly Ser Leu Leu Lys Glu Gly Ile His Ile Arg Leu
            660                 665                 670

Ser Gly Gln Asp Val Glu Arg Gly Thr Phe Ser His Arg His His Val
            675                 680                 685

Leu His Asp Gln Asn Val Asp Lys Arg Thr Cys Ile Pro Met Asn His
        690                 695                 700

Leu Trp Pro Asn Gln Ala Pro Tyr Thr Val Cys Asn Ser Ser Leu Ser
705                 710                 715                 720

Glu Tyr Gly Val Leu Gly Phe Glu Leu Gly Phe Ala Met Ala Ser Pro
                725                 730                 735

Asn Ala Leu Val Leu Trp Glu Ala Gln Phe Gly Asp Phe His Asn Thr
            740                 745                 750

Ala Gln Cys Ile Ile Asp Gln Phe Ile Cys Pro Gly Gln Ala Lys Trp
            755                 760                 765

Val Arg Gln Asn Gly Ile Val Leu Leu Leu Pro His Gly Met Glu Gly
        770                 775                 780

Met Gly Pro Glu His Ser Ser Ala Arg Pro Glu Arg Phe Leu Gln Met
785                 790                 795                 800

Cys Asn Asp Asp Pro Asp Val Leu Pro Asp Leu Lys Glu Ala Asn Phe
                805                 810                 815

Asp Ile Asn Gln Leu Tyr Asp Cys Asn Trp Val Val Asn Cys Ser
            820                 825                 830

Thr Pro Gly Asn Phe Phe His Val Leu Arg Arg Gln Ile Leu Leu Pro
            835                 840                 845

Phe Arg Lys Pro Leu Ile Ile Phe Thr Pro Lys Ser Leu Leu Arg His
        850                 855                 860

Pro Glu Ala Arg Ser Ser Phe Asp Glu Met Leu Pro Gly Thr His Phe
865                 870                 875                 880

Gln Arg Val Ile Pro Glu Asp Gly Pro Ala Ala Gln Asn Pro Glu Asn
                885                 890                 895

Val Lys Arg Leu Leu Phe Cys Thr Gly Lys Val Tyr Tyr Asp Leu Thr
            900                 905                 910
```

-continued

Arg Glu Arg Lys Ala Arg Asp Met Val Gly Gln Val Ala Ile Thr Arg
            915                 920                 925

Ile Glu Gln Leu Ser Pro Phe Pro Phe Asp Leu Leu Leu Lys Glu Val
        930                 935                 940

Gln Lys Tyr Pro Asn Ala Glu Leu Ala Trp Cys Gln Glu Glu His Lys
945                 950                 955                 960

Asn Gln Gly Tyr Tyr Asp Tyr Val Lys Pro Arg Leu Arg Thr Thr Ile
                965                 970                 975

Ser Arg Ala Lys Pro Val Trp Tyr Ala Gly Arg Asp Pro Ala Ala Ala
            980                 985                 990

Pro Ala Thr Gly Asn Lys Lys Thr His Leu Thr Glu Leu Gln Arg Leu
        995                 1000                1005

Leu Asp Thr Ala Phe Asp Leu Asp Val Phe Lys Asn Phe Ser
    1010                1015                1020

<210> SEQ ID NO 21
<211> LENGTH: 169
<212> TYPE: PRT
<213> ORGANISM: Homo sapiens

<400> SEQUENCE: 21

Met Ala Pro Pro Trp Val Pro Ala Met Gly Phe Thr Leu Ala Pro Ser
1               5                   10                  15

Leu Gly Cys Phe Val Gly Ser Arg Phe Val His Gly Glu Gly Leu Arg
            20                  25                  30

Trp Tyr Ala Gly Leu Gln Lys Pro Ser Trp His Pro Pro His Trp Val
        35                  40                  45

Leu Gly Pro Val Trp Gly Thr Leu Tyr Ser Ala Met Gly Tyr Gly Ser
    50                  55                  60

Tyr Leu Val Trp Lys Glu Leu Gly Gly Phe Thr Glu Lys Ala Val Val
65                  70                  75                  80

Pro Leu Gly Leu Tyr Thr Gly Gln Leu Ala Leu Asn Trp Ala Trp Pro
                85                  90                  95

Pro Ile Phe Phe Gly Ala Arg Gln Met Gly Trp Ala Leu Val Asp Leu
            100                 105                 110

Leu Leu Val Ser Gly Ala Ala Ala Thr Thr Val Ala Trp Tyr Gln Val
        115                 120                 125

Val Ser Pro Leu Ala Ala Arg Leu Leu Tyr Pro Tyr Leu Ala Trp Leu
    130                 135                 140

Ala Phe Thr Thr Thr Leu Asn Tyr Cys Val Trp Arg Asp Asn His Gly
145                 150                 155                 160

Trp Arg Gly Gly Arg Arg Leu Pro Glu
                165

<210> SEQ ID NO 22
<211> LENGTH: 782
<212> TYPE: PRT
<213> ORGANISM: Homo sapiens

<400> SEQUENCE: 22

Met Ala Pro His Arg Pro Ala Pro Ala Leu Leu Cys Ala Leu Ser Leu
1               5                   10                  15

Ala Leu Cys Ala Leu Ser Leu Pro Val Arg Ala Ala Thr Ala Ser Arg
            20                  25                  30

Gly Ala Ser Gln Ala Gly Ala Pro Gln Gly Arg Val Pro Glu Ala Arg
        35                  40                  45

-continued

```
Pro Asn Ser Met Val Val Glu His Pro Glu Phe Leu Lys Ala Gly Lys
    50                  55                  60

Glu Pro Gly Leu Gln Ile Trp Arg Val Glu Lys Phe Asp Leu Val Pro
65                  70                  75                  80

Val Pro Thr Asn Leu Tyr Gly Asp Phe Phe Thr Gly Asp Ala Tyr Val
                85                  90                  95

Ile Leu Lys Thr Val Gln Leu Arg Asn Gly Asn Leu Gln Tyr Asp Leu
                100                 105                 110

His Tyr Trp Leu Gly Asn Glu Cys Ser Gln Asp Glu Ser Gly Ala Ala
            115                 120                 125

Ala Ile Phe Thr Val Gln Leu Asp Asp Tyr Leu Asn Gly Arg Ala Val
        130                 135                 140

Gln His Arg Glu Val Gln Gly Phe Glu Ser Ala Thr Phe Leu Gly Tyr
145                 150                 155                 160

Phe Lys Ser Gly Leu Lys Tyr Lys Lys Gly Gly Val Ala Ser Gly Phe
                165                 170                 175

Lys His Val Val Pro Asn Glu Val Val Gln Arg Leu Phe Gln Val
            180                 185                 190

Lys Gly Arg Arg Val Val Arg Ala Thr Glu Val Pro Val Ser Trp Glu
            195                 200                 205

Ser Phe Asn Asn Gly Asp Cys Phe Ile Leu Asp Leu Gly Asn Asn Ile
        210                 215                 220

His Gln Trp Cys Gly Ser Asn Ser Asn Arg Tyr Glu Arg Leu Lys Ala
225                 230                 235                 240

Thr Gln Val Ser Lys Gly Ile Arg Asp Asn Glu Arg Ser Gly Arg Ala
                245                 250                 255

Arg Val His Val Ser Glu Glu Gly Thr Glu Pro Glu Ala Met Leu Gln
            260                 265                 270

Val Leu Gly Pro Lys Pro Ala Leu Pro Ala Gly Thr Glu Asp Thr Ala
        275                 280                 285

Lys Glu Asp Ala Ala Asn Arg Lys Leu Ala Lys Leu Tyr Lys Val Ser
    290                 295                 300

Asn Gly Ala Gly Thr Met Ser Val Ser Leu Val Ala Asp Glu Asn Pro
305                 310                 315                 320

Phe Ala Gln Gly Ala Leu Lys Ser Glu Asp Cys Phe Ile Leu Asp His
                325                 330                 335

Gly Lys Asp Gly Lys Ile Phe Val Trp Lys Gly Lys Gln Ala Asn Thr
            340                 345                 350

Glu Glu Arg Lys Ala Ala Leu Lys Thr Ala Ser Asp Phe Ile Thr Lys
        355                 360                 365

Met Asp Tyr Pro Lys Gln Thr Gln Val Ser Val Leu Pro Glu Gly Gly
    370                 375                 380

Glu Thr Pro Leu Phe Lys Gln Phe Phe Lys Asn Trp Arg Asp Pro Asp
385                 390                 395                 400

Gln Thr Asp Gly Leu Gly Leu Ser Tyr Leu Ser Ser His Ile Ala Asn
                405                 410                 415

Val Glu Arg Val Pro Phe Asp Ala Ala Thr Leu His Thr Ser Thr Ala
            420                 425                 430

Met Ala Ala Gln His Gly Met Asp Asp Gly Thr Gly Gln Lys Gln
        435                 440                 445

Ile Trp Arg Ile Glu Gly Ser Asn Lys Val Pro Val Asp Pro Ala Thr
    450                 455                 460

Tyr Gly Gln Phe Tyr Gly Gly Asp Ser Tyr Ile Ile Leu Tyr Asn Tyr
465                 470                 475                 480
```

```
Arg His Gly Gly Arg Gln Gly Gln Ile Ile Tyr Asn Trp Gln Gly Ala
                485                 490                 495

Gln Ser Thr Gln Asp Glu Val Ala Ala Ser Ala Ile Leu Thr Ala Gln
            500                 505                 510

Leu Asp Glu Glu Leu Gly Gly Thr Pro Val Gln Ser Arg Val Val Gln
            515                 520                 525

Gly Lys Glu Pro Ala His Leu Met Ser Leu Phe Gly Gly Lys Pro Met
        530                 535                 540

Ile Ile Tyr Lys Gly Gly Thr Ser Arg Glu Gly Gln Thr Ala Pro
545                 550                 555                 560

Ala Ser Thr Arg Leu Phe Gln Val Arg Ala Asn Ser Ala Gly Ala Thr
                565                 570                 575

Arg Ala Val Glu Val Leu Pro Lys Ala Gly Ala Leu Asn Ser Asn Asp
            580                 585                 590

Ala Phe Val Leu Lys Thr Pro Ser Ala Ala Tyr Leu Trp Val Gly Thr
        595                 600                 605

Gly Ala Ser Glu Ala Glu Lys Thr Gly Ala Gln Glu Leu Leu Arg Val
        610                 615                 620

Leu Arg Ala Gln Pro Val Gln Val Ala Glu Gly Ser Glu Pro Asp Gly
625                 630                 635                 640

Phe Trp Glu Ala Leu Gly Gly Lys Ala Ala Tyr Arg Thr Ser Pro Arg
                645                 650                 655

Leu Lys Asp Lys Lys Met Asp Ala His Pro Pro Arg Leu Phe Ala Cys
            660                 665                 670

Ser Asn Lys Ile Gly Arg Phe Val Ile Glu Glu Val Pro Gly Glu Leu
        675                 680                 685

Met Gln Glu Asp Leu Ala Thr Asp Asp Val Met Leu Leu Asp Thr Trp
        690                 695                 700

Asp Gln Val Phe Val Trp Val Gly Lys Asp Ser Gln Glu Glu Glu Lys
705                 710                 715                 720

Thr Glu Ala Leu Thr Ser Ala Lys Arg Tyr Ile Glu Thr Asp Pro Ala
                725                 730                 735

Asn Arg Asp Arg Arg Thr Pro Ile Thr Val Val Lys Gln Gly Phe Glu
            740                 745                 750

Pro Pro Ser Phe Val Gly Trp Phe Leu Gly Trp Asp Asp Asp Tyr Trp
        755                 760                 765

Ser Val Asp Pro Leu Asp Arg Ala Met Ala Glu Leu Ala Ala
        770                 775                 780

<210> SEQ ID NO 23
<211> LENGTH: 172
<212> TYPE: PRT
<213> ORGANISM: Homo sapiens

<400> SEQUENCE: 23

Met Pro Gly Ile Val Glu Leu Pro Thr Leu Glu Glu Leu Lys Val Asp
1               5                   10                  15

Glu Val Lys Ile Ser Ser Ala Val Leu Lys Ala Ala His His Tyr
            20                  25                  30

Gly Ala Gln Cys Asp Lys Pro Asn Lys Glu Phe Met Leu Cys Arg Trp
        35                  40                  45

Glu Glu Lys Asp Pro Arg Arg Cys Leu Glu Glu Gly Lys Leu Val Asn
        50                  55                  60

Lys Cys Ala Leu Asp Phe Phe Arg Gln Ile Lys Arg His Cys Ala Glu
65                  70                  75                  80
```

```
Pro Phe Thr Glu Tyr Trp Thr Cys Ile Asp Tyr Thr Gly Gln Gln Leu
                85                  90                  95

Phe Arg His Cys Arg Lys Gln Gln Ala Lys Phe Asp Glu Cys Val Leu
            100                 105                 110

Asp Lys Leu Gly Trp Val Arg Pro Asp Leu Gly Glu Leu Ser Lys Val
        115                 120                 125

Thr Lys Val Lys Thr Asp Arg Pro Leu Pro Glu Asn Pro Tyr His Ser
130                 135                 140

Arg Pro Arg Pro Asp Pro Ser Pro Glu Ile Glu Gly Asp Leu Gln Pro
145                 150                 155                 160

Ala Thr His Gly Ser Arg Phe Tyr Phe Trp Thr Lys
                165                 170
```

<210> SEQ ID NO 24
<211> LENGTH: 227
<212> TYPE: PRT
<213> ORGANISM: Homo sapiens

<400> SEQUENCE: 24

```
Met Gln Glu Pro Arg Arg Val Thr His Cys Leu Gly Lys Arg Gly Val
1               5                   10                  15

Lys Thr Pro Gln Leu Gln Pro Gly Ser Ala Phe Leu Pro Arg Val Arg
            20                  25                  30

Arg Gln Ser Phe Thr Ala Arg Ser Asp Ser Tyr Thr Thr Val Arg Asp
        35                  40                  45

Phe Leu Ala Val Pro Arg Thr Ile Ser Ser Ala Ser Thr Leu Ile
    50                  55                  60

Met Ala Val Ala Val Ser His Phe Arg Pro Gly Pro Glu Val Trp Asp
65                  70                  75                  80

Thr Ala Ser Met Ala Ala Ser Lys Val Lys Gln Asp Met Pro Pro Pro
                85                  90                  95

Gly Gly Tyr Gly Pro Ile Asp Tyr Lys Arg Asn Leu Pro Arg Arg Gly
            100                 105                 110

Leu Ser Gly Tyr Ser Met Leu Ala Ile Gly Ile Gly Thr Leu Ile Tyr
        115                 120                 125

Gly His Trp Ser Ile Met Lys Trp Asn Arg Glu Arg Arg Leu Gln
        130                 135                 140

Ile Glu Asp Phe Glu Ala Arg Ile Ala Leu Leu Pro Leu Leu Gln Ala
145                 150                 155                 160

Glu Thr Asp Arg Arg Thr Leu Gln Met Leu Arg Glu Asn Leu Glu Glu
                165                 170                 175

Glu Ala Ile Ile Met Lys Asp Val Pro Asp Trp Lys Val Gly Glu Ser
            180                 185                 190

Val Phe His Thr Thr Arg Trp Val Pro Pro Leu Ile Gly Glu Leu Tyr
        195                 200                 205

Gly Leu Arg Thr Thr Glu Glu Ala Leu His Ala Ser His Gly Phe Met
    210                 215                 220

Trp Tyr Thr
225
```

<210> SEQ ID NO 25
<211> LENGTH: 1168
<212> TYPE: PRT
<213> ORGANISM: Homo sapiens

<400> SEQUENCE: 25

-continued

```
Met Ser Trp Phe Ser Gly Leu Leu Val Pro Lys Val Asp Glu Arg Lys
 1               5                  10                  15
Thr Ala Trp Gly Glu Arg Asn Gly Gln Lys Arg Ser Arg Arg Arg Gly
             20                  25                  30
Thr Arg Ala Gly Gly Phe Cys Thr Pro Arg Tyr Met Ser Cys Leu Arg
             35                  40                  45
Asp Ala Glu Pro Pro Ser Pro Thr Pro Ala Gly Pro Pro Arg Cys Pro
         50                  55                  60
Trp Gln Asp Asp Ala Phe Ile Arg Arg Gly Pro Gly Lys Gly Lys
 65                  70                  75              80
Glu Leu Gly Leu Arg Ala Val Ala Leu Gly Phe Glu Asp Thr Glu Val
                 85                  90                  95
Thr Thr Thr Ala Gly Gly Thr Ala Glu Val Ala Pro Asp Ala Val Pro
             100                 105                 110
Arg Ser Gly Arg Ser Cys Trp Arg Arg Leu Val Gln Val Phe Gln Ser
             115                 120                 125
Lys Gln Phe Arg Ser Ala Lys Leu Glu Arg Leu Tyr Gln Arg Tyr Phe
         130                 135                 140
Phe Gln Met Asn Gln Ser Ser Leu Thr Leu Leu Met Ala Val Leu Val
145                 150                 155                 160
Leu Leu Thr Ala Val Leu Leu Ala Phe His Ala Ala Pro Ala Arg Pro
                 165                 170                 175
Gln Pro Ala Tyr Val Ala Leu Ala Cys Ala Ala Ala Leu Phe Val
             180                 185                 190
Gly Leu Met Val Val Cys Asn Arg His Ser Phe Arg Gln Asp Ser Met
             195                 200                 205
Trp Val Val Ser Tyr Val Val Leu Gly Ile Leu Ala Ala Val Gln Val
         210                 215                 220
Gly Gly Ala Leu Ala Ala Asp Pro Arg Ser Pro Ser Ala Gly Leu Trp
225                 230                 235                 240
Cys Pro Val Phe Phe Val Tyr Ile Ala Tyr Thr Leu Leu Pro Ile Arg
                 245                 250                 255
Met Arg Ala Ala Val Leu Ser Gly Leu Gly Leu Ser Thr Leu His Leu
             260                 265                 270
Ile Leu Ala Trp Gln Leu Asn Arg Gly Asp Ala Phe Leu Trp Lys Gln
         275                 280                 285
Leu Gly Ala Asn Val Leu Leu Phe Leu Cys Thr Asn Val Ile Gly Ile
         290                 295                 300
Cys Thr His Tyr Pro Ala Glu Val Ser Gln Arg Gln Ala Phe Gln Glu
305                 310                 315                 320
Thr Arg Gly Tyr Ile Gln Ala Arg Leu His Leu Gln His Glu Asn Arg
             325                 330                 335
Gln Gln Glu Arg Leu Leu Leu Ser Val Leu Pro Gln His Val Ala Met
             340                 345                 350
Glu Met Lys Glu Asp Ile Asn Thr Lys Lys Glu Asp Met Met Phe His
         355                 360                 365
Lys Ile Tyr Ile Gln Lys His Asp Asn Val Ser Ile Leu Phe Ala Asp
         370                 375                 380
Ile Glu Gly Phe Thr Ser Leu Ala Ser Gln Cys Thr Ala Gln Glu Leu
385                 390                 395                 400
Val Met Thr Leu Asn Glu Leu Phe Ala Arg Phe Asp Lys Leu Ala Ala
                 405                 410                 415
Glu Asn His Cys Leu Arg Ile Lys Ile Leu Gly Asp Cys Tyr Tyr Cys
             420                 425                 430
```

```
Val Ser Gly Leu Pro Glu Ala Arg Ala Asp His Ala His Cys Cys Val
        435                 440                 445

Glu Met Gly Val Asp Met Ile Glu Ala Ile Ser Leu Val Arg Glu Val
        450                 455                 460

Thr Gly Val Asn Val Asn Met Arg Val Gly Ile His Ser Gly Arg Val
465                 470                 475                 480

His Cys Gly Val Leu Gly Leu Arg Lys Trp Gln Phe Asp Val Trp Ser
                485                 490                 495

Asn Asp Val Thr Leu Ala Asn His Met Glu Ala Gly Gly Arg Ala Gly
                500                 505                 510

Arg Ile His Ile Thr Arg Ala Thr Leu Gln Tyr Leu Asn Gly Asp Tyr
            515                 520                 525

Glu Val Glu Pro Gly Arg Gly Glu Arg Asn Ala Tyr Leu Lys Glu
        530                 535                 540

Gln His Ile Glu Thr Phe Leu Ile Leu Gly Ala Ser Gln Lys Arg Lys
545                 550                 555                 560

Glu Glu Lys Ala Met Leu Ala Lys Leu Gln Arg Thr Arg Ala Asn Ser
                565                 570                 575

Met Glu Gly Leu Met Pro Arg Trp Val Pro Asp Arg Ala Phe Ser Arg
                580                 585                 590

Thr Lys Asp Ser Lys Ala Phe Arg Gln Met Gly Ile Asp Asp Ser Ser
            595                 600                 605

Lys Asp Asn Arg Gly Thr Gln Asp Ala Leu Asn Pro Glu Asp Glu Val
        610                 615                 620

Asp Glu Phe Leu Ser Arg Ala Ile Asp Ala Arg Ser Ile Asp Gln Leu
625                 630                 635                 640

Arg Lys Asp His Val Arg Arg Phe Leu Leu Thr Phe Gln Arg Glu Asp
                645                 650                 655

Leu Glu Lys Lys Tyr Ser Arg Lys Val Asp Pro Arg Phe Gly Ala Tyr
                660                 665                 670

Val Ala Cys Ala Leu Leu Val Phe Cys Phe Ile Cys Phe Ile Gln Leu
            675                 680                 685

Leu Ile Phe Pro His Ser Thr Leu Met Leu Gly Ile Tyr Ala Ser Ile
        690                 695                 700

Phe Leu Leu Leu Leu Ile Thr Val Leu Ile Cys Ala Val Tyr Ser Cys
705                 710                 715                 720

Gly Ser Leu Phe Pro Lys Ala Leu Gln Arg Leu Ser Arg Ser Ile Val
                725                 730                 735

Arg Ser Arg Ala His Ser Thr Ala Val Gly Ile Phe Ser Val Leu Leu
            740                 745                 750

Val Phe Thr Ser Ala Ile Ala Asn Met Phe Thr Cys Asn His Thr Pro
        755                 760                 765

Ile Arg Ser Cys Ala Ala Arg Met Leu Asn Leu Thr Pro Ala Asp Ile
        770                 775                 780

Thr Ala Cys His Leu Gln Gln Leu Asn Tyr Ser Leu Gly Leu Asp Ala
785                 790                 795                 800

Pro Leu Cys Glu Gly Thr Met Pro Thr Cys Ser Phe Pro Glu Tyr Phe
                805                 810                 815

Ile Gly Asn Met Leu Leu Ser Leu Leu Ala Ser Ser Val Phe Leu His
                820                 825                 830

Ile Ser Ser Ile Gly Lys Leu Ala Met Ile Phe Val Leu Gly Leu Ile
            835                 840                 845

Tyr Leu Val Leu Leu Leu Leu Gly Pro Pro Ala Thr Ile Phe Asp Asn
```

```
                850           855           860
Tyr Asp Leu Leu Leu Gly Val His Gly Leu Ala Ser Ser Asn Glu Thr
865                 870                 875                 880

Phe Asp Gly Leu Asp Cys Pro Ala Ala Gly Arg Val Ala Leu Lys Tyr
                    885                 890                 895

Met Thr Pro Val Ile Leu Leu Val Phe Ala Leu Ala Leu Tyr Leu His
            900                 905                 910

Ala Gln Gln Val Glu Ser Thr Ala Arg Leu Asp Phe Leu Trp Lys Leu
        915                 920                 925

Gln Ala Thr Gly Glu Lys Glu Glu Met Glu Glu Leu Gln Ala Tyr Asn
    930                 935                 940

Arg Arg Leu Leu His Asn Ile Leu Pro Lys Asp Val Ala Ala His Phe
945                 950                 955                 960

Leu Ala Arg Glu Arg Arg Asn Asp Glu Leu Tyr Tyr Gln Ser Cys Glu
                965                 970                 975

Cys Val Ala Val Met Phe Ala Ser Ile Ala Asn Phe Ser Glu Phe Tyr
            980                 985                 990

Val Glu Leu Glu Ala Asn Asn Glu Gly Val Glu Cys Leu Arg Leu Leu
        995                 1000                1005

Asn Glu Ile Ile Ala Asp Phe Asp Glu Ile Ile Ser Glu Glu Arg Phe
    1010                1015                1020

Arg Gln Leu Glu Lys Ile Lys Thr Ile Gly Ser Thr Tyr Met Ala Ala
1025                1030                1035                1040

Ser Gly Leu Asn Ala Ser Thr Tyr Asp Gln Val Gly Arg Ser His Ile
                1045                1050                1055

Thr Ala Leu Ala Asp Tyr Ala Met Arg Leu Met Glu Gln Met Lys His
            1060                1065                1070

Ile Asn Glu His Ser Phe Asn Asn Phe Gln Met Lys Ile Gly Leu Asn
        1075                1080                1085

Met Gly Pro Val Val Ala Gly Val Ile Gly Ala Arg Lys Pro Gln Tyr
    1090                1095                1100

Asp Ile Trp Gly Asn Thr Val Asn Val Ser Ser Arg Met Asp Ser Thr
1105                1110                1115                1120

Gly Val Pro Asp Arg Ile Gln Val Thr Thr Asp Leu Tyr Gln Val Leu
                1125                1130                1135

Ala Ala Lys Gly Tyr Gln Leu Glu Cys Arg Gly Val Val Lys Val Lys
            1140                1145                1150

Gly Lys Gly Glu Met Thr Thr Tyr Phe Leu Asn Gly Gly Pro Ser Ser
        1155                1160                1165

<210> SEQ ID NO 26
<211> LENGTH: 16
<212> TYPE: PRT
<213> ORGANISM: Homo sapiens

<400> SEQUENCE: 26

Thr Asn Gly Gly Gln Glu Arg Lys Phe Val Gly Gly Ser Gly Gln Cys
1               5                   10                  15

<210> SEQ ID NO 27
<211> LENGTH: 1080
<212> TYPE: PRT
<213> ORGANISM: Homo sapiens

<400> SEQUENCE: 27

Met Pro Ala Lys Gly Arg Tyr Phe Leu Asn Glu Gly Glu Glu Gly Pro
1               5                   10                  15
```

```
Asp Gln Asp Ala Leu Tyr Glu Lys Tyr Gln Leu Thr Ser Gln His Gly
            20                  25                  30

Pro Leu Leu Leu Thr Leu Leu Val Ala Ala Thr Ala Cys Val Ala
                35                  40                  45

Leu Ile Ile Ile Ala Phe Ser Gln Gly Asp Pro Ser Arg His Gln Ala
 50                  55                  60

Ile Leu Gly Met Ala Phe Leu Val Leu Ala Val Phe Ala Ala Leu Ser
65                  70                  75                  80

Val Leu Met Tyr Val Glu Cys Leu Leu Arg Arg Trp Leu Arg Ala Leu
                85                  90                  95

Ala Leu Leu Thr Trp Ala Cys Leu Val Ala Leu Gly Tyr Val Leu Val
                100                 105                 110

Phe Asp Ala Trp Thr Lys Ala Ala Cys Ala Trp Glu Gln Val Pro Phe
            115                 120                 125

Phe Leu Phe Ile Val Phe Val Val Tyr Thr Leu Leu Pro Phe Ser Met
            130                 135                 140

Arg Gly Ala Val Ala Val Gly Ala Val Ser Thr Ala Ser His Leu Leu
145                 150                 155                 160

Val Leu Gly Ser Leu Met Gly Gly Phe Thr Thr Pro Ser Val Arg Val
                165                 170                 175

Gly Leu Gln Leu Leu Ala Asn Ala Val Ile Phe Leu Cys Gly Asn Leu
            180                 185                 190

Thr Gly Ala Phe His Lys His Gln Met Gln Asp Ala Ser Arg Asp Leu
            195                 200                 205

Phe Thr Tyr Thr Val Lys Cys Ile Gln Ile Arg Arg Lys Leu Arg Ile
            210                 215                 220

Glu Lys Arg Gln Gln Glu Asn Leu Leu Leu Ser Val Leu Pro Ala His
225                 230                 235                 240

Ile Ser Met Gly Met Lys Leu Ala Ile Ile Glu Arg Leu Lys Glu His
                245                 250                 255

Gly Asp Arg Arg Cys Met Pro Asp Asn Asn Phe His Ser Leu Tyr Val
                260                 265                 270

Lys Arg His Gln Asn Val Ser Ile Leu Tyr Ala Asp Ile Val Gly Phe
            275                 280                 285

Thr Gln Leu Ala Ser Asp Cys Ser Pro Lys Glu Leu Val Val Val Leu
            290                 295                 300

Asn Glu Leu Phe Gly Lys Phe Asp Gln Ile Ala Lys Ala Asn Glu Cys
305                 310                 315                 320

Met Arg Ile Lys Ile Leu Gly Asp Cys Tyr Tyr Cys Val Ser Gly Leu
                325                 330                 335

Pro Val Ser Leu Pro Thr His Ala Arg Asn Cys Val Lys Met Gly Leu
                340                 345                 350

Asp Met Cys Gln Ala Ile Lys Gln Val Arg Glu Ala Thr Gly Val Asp
            355                 360                 365

Ile Asn Met Arg Val Gly Ile His Ser Gly Asn Val Leu Cys Gly Val
            370                 375                 380

Ile Gly Leu Arg Lys Trp Gln Tyr Asp Val Trp Ser His Asp Val Ser
385                 390                 395                 400

Leu Ala Asn Arg Met Glu Ala Ala Gly Val Pro Gly Arg Val His Ile
                405                 410                 415

Thr Glu Ala Thr Leu Lys His Leu Asp Lys Ala Tyr Glu Val Glu Asp
            420                 425                 430

Gly His Gly Gln Gln Arg Asp Pro Tyr Leu Lys Glu Met Asn Ile Arg
```

```
                435                 440                 445
Thr Tyr Leu Val Ile Asp Pro Arg Ser Gln Gln Pro Pro Pro Ser
450                 455                 460
Gln His Leu Pro Arg Pro Lys Gly Asp Ala Ala Leu Lys Met Arg Ala
465                 470                 475                 480
Ser Val Arg Met Thr Arg Tyr Leu Glu Ser Trp Gly Ala Ala Arg Pro
                485                 490                 495
Phe Ala His Leu Asn His Arg Glu Ser Val Ser Ser Gly Glu Thr His
                500                 505                 510
Val Pro Asn Gly Arg Arg Pro Lys Ser Val Pro Gln Arg His Arg Arg
                515                 520                 525
Thr Pro Asp Arg Ser Met Ser Pro Lys Gly Arg Ser Glu Asp Asp Ser
530                 535                 540
Tyr Asp Asp Glu Met Leu Ser Ala Ile Glu Gly Leu Ser Ser Thr Arg
545                 550                 555                 560
Pro Cys Cys Ser Lys Ser Asp Asp Phe Tyr Thr Phe Gly Ser Ile Phe
                565                 570                 575
Leu Glu Lys Gly Phe Glu Arg Glu Tyr Arg Leu Ala Pro Ile Pro Arg
                580                 585                 590
Ala Arg His Asp Phe Ala Cys Ala Ser Leu Ile Phe Val Cys Ile Leu
                595                 600                 605
Leu Val His Val Leu Leu Met Pro Arg Thr Ala Ala Leu Gly Val Ser
                610                 615                 620
Phe Gly Leu Val Ala Cys Val Leu Gly Leu Val Leu Gly Leu Cys Phe
625                 630                 635                 640
Ala Thr Lys Phe Ser Arg Cys Cys Pro Ala Arg Gly Thr Leu Cys Thr
                645                 650                 655
Ile Ser Glu Arg Val Glu Thr Gln Pro Leu Leu Arg Leu Thr Leu Ala
                660                 665                 670
Val Leu Thr Ile Gly Ser Leu Leu Thr Val Ala Ile Ile Asn Leu Pro
                675                 680                 685
Leu Met Pro Phe Gln Val Pro Glu Leu Pro Val Gly Asn Glu Thr Gly
                690                 695                 700
Leu Leu Ala Ala Ser Ser Lys Thr Arg Ala Leu Cys Glu Pro Leu Pro
705                 710                 715                 720
Tyr Tyr Thr Cys Ser Cys Val Leu Gly Phe Ile Ala Cys Ser Val Phe
                725                 730                 735
Leu Arg Met Ser Leu Glu Pro Lys Val Val Leu Leu Thr Val Ala Leu
                740                 745                 750
Val Ala Tyr Leu Val Leu Phe Asn Leu Ser Pro Cys Trp Gln Trp Asp
                755                 760                 765
Cys Cys Gly Gln Gly Leu Gly Asn Leu Thr Lys Pro Asn Gly Thr Thr
770                 775                 780
Ser Gly Thr Pro Ser Cys Ser Trp Lys Asp Leu Lys Thr Met Thr Asn
785                 790                 795                 800
Phe Tyr Leu Val Leu Phe Tyr Ile Thr Leu Leu Thr Leu Ser Arg Gln
                805                 810                 815
Ile Asp Tyr Tyr Cys Arg Leu Asp Cys Leu Trp Lys Lys Lys Phe Lys
                820                 825                 830
Lys Glu His Glu Glu Phe Glu Thr Met Glu Asn Val Asn Arg Leu Leu
                835                 840                 845
Leu Glu Asn Val Leu Pro Ala His Val Ala Ala His Phe Ile Gly Asp
                850                 855                 860
```

```
                                           -continued

Lys Leu Asn Glu Asp Trp Tyr His Gln Ser Tyr Asp Cys Val Cys Val
865                 870                 875                 880

Met Phe Ala Ser Val Pro Asp Phe Lys Val Phe Tyr Thr Glu Cys Asp
                885                 890                 895

Val Asn Lys Glu Gly Leu Glu Cys Leu Arg Leu Leu Asn Glu Ile Ile
            900                 905                 910

Ala Asp Phe Asp Glu Leu Leu Leu Lys Pro Lys Phe Ser Gly Val Glu
        915                 920                 925

Lys Ile Lys Thr Ile Gly Ser Thr Tyr Met Ala Ala Ala Gly Leu Ser
    930                 935                 940

Val Ala Ser Gly His Glu Asn Gln Glu Leu Glu Arg Gln His Ala His
945                 950                 955                 960

Ile Gly Val Met Val Glu Phe Ser Ile Ala Leu Met Ser Lys Leu Asp
                965                 970                 975

Gly Ile Asn Arg His Ser Phe Asn Ser Phe Arg Leu Arg Val Gly Ile
            980                 985                 990

Asn His Gly Pro Val Ile Ala Gly Val Ile Gly Ala Arg Lys Pro Gln
        995                 1000                1005

Tyr Asp Ile Trp Gly Asn Thr Val Asn Val Ala Ser Arg Met Glu Ser
    1010                1015                1020

Thr Gly Glu Leu Gly Lys Ile Gln Val Thr Glu Glu Thr Cys Thr Ile
1025                1030                1035                1040

Leu Gln Gly Leu Gly Tyr Ser Cys Glu Cys Arg Gly Leu Ile Asn Val
                1045                1050                1055

Lys Gly Lys Gly Glu Leu Arg Thr Tyr Phe Val Cys Thr Asp Thr Ala
                1060                1065                1070

Lys Phe Gln Gly Leu Gly Leu Asn
        1075                1080
```